US012697331B2

(12) United States Patent
Reddy et al.

(10) Patent No.: US 12,697,331 B2
(45) Date of Patent: Aug. 4, 2026

(54) METHODS OF USE OF T-TYPE CALCIUM CHANNEL MODULATORS

(71) Applicant: PRAXIS PRECISION MEDICINES, INC., Boston, MA (US)

(72) Inventors: Kiran Reddy, Boston, MA (US); Gabriel Maurice Belfort, Cambridge, MA (US); Bernard Ravina, Newton, MA (US); Marion Wittmann, Medford, MA (US)

(73) Assignee: Praxis Precision Medicines, Inc., Boston, MA (US)

(*) Notice: Subject to any disclaimer, the term of this patent is extended or adjusted under 35 U.S.C. 154(b) by 891 days.

(21) Appl. No.: 17/975,457

(22) Filed: Oct. 27, 2022

(65) Prior Publication Data

US 2023/0165847 A1 Jun. 1, 2023

Related U.S. Application Data

(63) Continuation of application No. PCT/US2021/029539, filed on Apr. 28, 2021.

(60) Provisional application No. 63/082,946, filed on Sep. 24, 2020, provisional application No. 63/050,410, filed on Jul. 10, 2020, provisional application No. 63/017,140, filed on Apr. 29, 2020.

(51) Int. Cl.

*A61K 31/445* (2006.01)
*A61K 9/20* (2006.01)
*A61P 25/08* (2006.01)
*A61P 25/14* (2006.01)

(52) U.S. Cl.

CPC .......... *A61K 31/445* (2013.01); *A61K 9/2054* (2013.01); *A61P 25/08* (2018.01); *A61P 25/14* (2018.01)

(58) Field of Classification Search

CPC .... A61K 31/445; A61K 9/2054; A61K 47/38; A61P 25/08; A61P 25/14; A61P 3/00; A61P 3/04; A61P 25/00
USPC .......................................................... 514/331
See application file for complete search history.

(56) References Cited

U.S. PATENT DOCUMENTS 10,562,857 B2 2/2020 Xie et al.
2009/0298883 A1 12/2009 Pajouhesh et al.
2018/0280357 A1 10/2018 Maricich
2018/0312471 A1 11/2018 Xie et al.
2025/0295646 A1* 9/2025 Reddy .................... A61P 25/14

FOREIGN PATENT DOCUMENTS

WO 2018/109152 A1 6/2018
WO WO-2018118101 A1 * 6/2018 ............. A61P 25/24
WO 2019/094724 A1 5/2019
WO 2020/072773 A1 4/2020
WO 2021/007487 A1 1/2021

OTHER PUBLICATIONS

Majumder et al.Journal of Pharmacy and pharmacology, 2016, 4, 381-385 (Year: 2016).*
International Search Report and Written Opinion for Application No. PCT/US2021/029539, dated Sep. 2, 2021, 10 pages.
Casillas-Espinosa et al., Z944, a Novel Selective T-Type Calcium Channel Antagonist Delays the Progression of Seizures in the Amygdala Kindling Model. PLoS One. Aug. 14, 2015;10(8):e0130012, 12 pages.
Namdari, Assessment of Potential Pharmacokinetic and pharmacodynamic Interactions between NBI-921352/XEN901, a Novel Nav1.6-Selective Sodium Channel Blocker, a Phenytoin (a Non-selective Nav Blocker) in Adult Healthy Subjects. Electronic Poster Presentation at the 2020 American Acacemy of Neurology (AAN) Meeting. 12 pages, (2020).
Tringham et al., T-type calcium channel blockers that attenuate thalamic burst firing and suppress absence seizures. Sci Transl Med. Feb. 15, 2012;4(121):121ra19, 14 pages.
Fishman et al., Antiepileptic Drug Titration and Related Health Care Resource Use and Costs. J Manag Care Spec Pharm. 2018;24(9):929-938.
Lu et al., Research Progress on the Role of T-type Channels in Epilepsy. Chin J Nerv Dis. Jul. 2013;39(7):447-449.
Makary et al., Principles of Salt Formation. UK Journal of Pharmaceutical and Bioscience. 2014;2(4):1-4.
Roy et al., Formulation and design of sustained release matrix tablets of metformin hydrochloride: Influence of hypromellose and polyacrylate polymers. Int J Appl Basic Med Res. Jan. 2013;3(1):55-63.

* cited by examiner

*Primary Examiner* — Yevgeny Valenrod
(74) *Attorney, Agent, or Firm* — McCarter & English, LLP; Jonathan Sparks; Yelena Margolin

(57) ABSTRACT

Described herein, in part, are methods useful for preventing and/or treating a disease or condition relating to aberrant function or activity of a T-type calcium channel, such as psychiatric disorders (e.g., mood disorder (e.g., major depressive disorder)), pain, tremor (e.g., essential tremor), seizures (e.g., absence seizures), epilepsy, or an epilepsy syndrome (e.g., juvenile myoclonic epilepsy). The present invention further comprises methods for modulating the function of a T-type calcium channel and methods of administering a titrated dosage of a T-type calcium channel antagonist.

30 Claims, 19 Drawing Sheets

METHODS OF USE OF T-TYPE CALCIUM CHANNEL MODULATORS

CROSS-REFERENCE TO RELATED APPLICATIONS

This application is a continuation of International Application No. PCT/US2021/029539, filed on Apr. 28, 2021; which claims the benefit of, and relies on the filing date of, U.S. Provisional Patent Application No. 63/017,140, filed on Apr. 29, 2020; U.S. Provisional Patent Application No. 63/050,410, filed on Jul. 10, 2020; and U.S. Provisional Patent Application No. 63/082,946, filed on Sep. 24, 2020. The entire contents of each of the foregoing applications are hereby incorporated herein by reference.

BACKGROUND

T-type calcium channels are low-voltage activated ion channels that mediate the influx of calcium into cells. Aberrant function or activity of these ion channels is associated with several diseases or conditions, including psychiatric disorders (e.g., mood disorder (e.g., major depressive disorder)), pain, tremor (e.g., essential tremor), epilepsy, or an epilepsy syndrome (e.g., absence seizures and juvenile myoclonic epilepsy).

In treating diseases or conditions related to aberrant function or activity of T-type calcium channels, the tolerability of potential pharmaceutical therapeutics is a factor to be considered. When investigating new therapeutics, tolerability is a clinically-defined term that refers to both patient (or study participant) and clinician (or investigator) input. The patient input is their willingness to continue taking the therapeutic, and the clinician input is based on their assessment of the severity and/or number of adverse effects and whether the patient should continue to be dosed with the therapeutic.

Either party may decide that the drug is intolerable and thereby discontinue dosing. Assessment of tolerability may also be based on the relationship between the adverse effects informing tolerability and the expected or perceived benefit. Accordingly, life-threatening diseases or conditions, for example, may allow for more severe or an increased number of adverse events before designating a particular therapeutic or therapeutic dose intolerable, while less severe or fewer adverse events may be indicated for considering a therapeutic dose intolerable for a less serious disease or condition.

One disorder with underlying aberrant T-type calcium channel function or activity, essential tremor, may affect an individual's ability to function in daily life, but is typically not life-threatening. Therefore, it is desirable that any adverse events experienced by the patient not worsen patient function, or the drug may be deemed intolerable by the patient and/or the clinician. Certain therapeutics can cause relatively minor adverse events, such as sedation or fatigue, that may be considered tolerable for serious neurological diseases such as, for example, amyotrophic lateral sclerosis, or for potentially fatal conditions such as refractory epilepsy. Those same adverse events, however, may be considered intolerable in other conditions, including, for example, certain cases of essential tremor.

The tolerability or intolerability of a therapeutic for a given disease or condition may be supported by clinical experience with standard of care, market research, and/or clinical trials. For instance, investigators have reported an intolerability of more than 30% during relatively short trials (i.e., an average of less than 11 weeks) for certain essential tremor therapeutics, such as primidone and topiramate. Ferreira, J J, et al., *MDS Evidence Based Review of Treatments for Essential Tremor*, Movement Disorders 2019:1-9; see also PCT Published Application No. WO 2020/072773 at Example 25, Table 34, reporting a 23% discontinuation rate in a 28-day essential tremor study of CX-8998, of which 17% was due to intolerability of adverse events. Likewise, the discontinuation rate over time has been shown to steadily increase for various essential tremor therapeutics, including, for example, gabapentin, propranolol, primidone, and topiramate.

In addition, while clinical trials for two non-selective T-type calcium channel inhibititors, zonisamide and topiramate, have shown those two compounds to be effective for treating essential tremors, adverse effects that resulted in patient discontinuance have limited development of these non-selective T-type calcium channel inhibititors for treating essential tremor. Haubenberger et al., *Essential Tremor*, N Engl J Med., 2018, 378:1802-10; Handforth et al., *Zonisamide for essential tremor: an evaluator blinded study*, Mov. Disord., 2009, 24:437-40; Chang et al., *Efficacy and safety of topiramate for essential tremor: a meta-analysis of randomized controlled trials*, Medicine 2015, 94:1-7.

Adverse events are believed to be correlated to the pharmacokinetic parameters of a drug substance, including, for example, the maximum plasma concentration of the drug after administration ($C_{max}$) and the area under the plasma concentration-time curve from time of administration (AUC). In general, as the $C_{max}$ and/or AUC increases, adverse events are reported to increase. Malangu, N., *Linkages between Pharmacokinetics and Adverse Effects of Drugs*, Pharmacokinetics and Adverse Effects of Drugs—Mechanisms and Risk Factors 2018.

Accordingly, regulating pharmacokinetic parameters and developing effective therapeutic doses and/or effective therapeutic dosage schedules, particularly those that permit an increase of the therapeutically-effective dose and/or pharmacokinetic parameters, such as $C_{max}$ and $AUC_{24}$, without increasing the number or severity of adverse events, may serve to increase patient compliance and, thus, benefit patients with diseases or conditions involving T-type calcium channels, including, for example, essential tremor.

SUMMARY

Described herein are methods of preventing and/or treating a disease or condition relating to aberrant function or activity of T-type calcium channels, such as psychiatric disorders (e.g., mood disorder (e.g., major depressive disorder)), pain, tremor (e.g., essential tremor), seizures (e.g., absence seizures), epilepsy, or an epilepsy syndrome (e.g., juvenile myoclonic epilepsy). Also disclosed herein are methods for modulating the function of a T-type calcium channel and methods of administering a titrated dosage of a T-type calcium channel antagonist, such as the compound of formula (I) or a pharmaceutically acceptable salt thereof.

In one aspect, the methods of treating a disease or condition relating to aberrant function or activity of a T-type calcium channel in a subject in need thereof comprise (a) administering a first dose of a compound of formula (I) or a pharmaceutically acceptable salt thereof to the subject for a first period of time, wherein following administration of the first dose of the compound for the first period of time the subject has a maximum plasma drug concentration ($C_{max}$) ranging from about 30 ng/mL to about 130 ng/mL and/or an area under the plasma concentration-time curve from time of administration to 24 hours after administration ($AUC_{24}$)

ranging from about 490 ng*h/mL to about 2030 ng*h/mL; (b) increasing the amount of the compound in the first dose and administering one or more increased doses of the compound to the subject to arrive at a maximum titrated dose; and (c) administering the maximum titrated dose of the compound to the subject to maintain in the subject a $C_{max}$ ranging from about 280 ng/mL to about 470 ng/mL and/or an $AUC_{24}$ ranging from about 3480 ng*h/mL to about 5800 ng*h/mL. Typically, each dose is administered once daily; however, the frequency of administration may be altered as long as the desired $C_{max}$ and/or $AUC_{24}$ values are achieved, as discussed in other sections of this application.

In certain aspects, step (b) comprises increasing the first dose to a second dose and administering the second dose of the compound to the subject for a second period of time, wherein following administration of the second dose of the compound for the second period of time, the subject has a $C_{max}$ ranging from about 80 ng/mL to about 300 ng/mL and/or an $AUC_{24}$ ranging from about 1220 ng*h/mL to about 4070 ng*h/mL. In certain aspects, step (b) comprises increasing the first dose to a second dose and administering the second dose of the compound to the subject for a second period of time, wherein following administration of the second dose of the compound for the second period of time, the subject has a $C_{max}$ ranging from about 80 ng/mL to about 220 ng/mL and/or an $AUC_{24}$ ranging from about 1220 ng*h/mL to about 3330 ng*h/mL; and increasing the second dose to a third dose and administering the third dose of the compound to the subject for a third period of time, wherein following administration of the third dose of the compound for the third period of time, the subject has a $C_{max}$ ranging from about 180 ng/mL to about 380 ng/mL and/or an $AUC_{24}$ ranging from about 2440 ng*h/mL to about 4700 ng*h/mL.

In various other aspects disclosed herein, step (b) comprises: (i) increasing the first dose to a second dose and administering the second dose of the compound to the subject for a second period of time, wherein following administration of the second dose of the compound for the second period of time, the subject has a $C_{max}$ ranging from about 80 ng/mL to about 130 ng/mL and/or an $AUC_{24}$ ranging from about 1220 ng*h/mL to about 2030 ng*h/mL; (ii) increasing the second dose to a third dose and administering the third dose of the compound to the subject for a third period of time, wherein following administration of the third dose of the compound for the third period of time, the subject has a $C_{max}$ ranging from about 130 ng/mL to about 220 ng/mL and/or an $AUC_{24}$ ranging from about 2000 ng*h/mL to about 3330 ng*h/mL; (iii) increasing the third dose to a fourth dose and administering the fourth dose of the compound to the subject for a fourth period of time, wherein following administration of the fourth dose of the compound for the fourth period of time, the subject has a $C_{max}$ ranging from about 180 ng/mL to about 300 ng/mL and/or an $AUC_{24}$ ranging from about 2440 ng*h/mL to about 4070 ng*h/mL; and (iv) increasing the fourth dose to a fifth dose and administering the fifth dose of the compound to the subject for a fifth period of time, wherein following administration of the fifth dose of the compound for the fifth period of time, the subject has a $C_{max}$ ranging from about 230 ng/mL to about 380 ng/mL and/or an $AUC_{24}$ ranging from about 2820 ng*h/mL to about 4700 ng*h/mL.

Further disclosed herein are methods of treating a disease or condition relating to aberrant function or activity of a T-type calcium channel in a subject in need thereof, the method comprising (a) administrating a first dose of a compound of formula (I) or a pharmaceutically acceptable salt thereof to the subject for a first period of time in an amount ranging from about 5 mg to about 40 mg per day; (b) increasing the amount of the compound in the first dose and administering one or more increased doses of the compound to the subject to arrive at a maximum titrated dose; and (c) administrating the maximum titrated dose of the compound to the subject in an amount ranging from about 20 mg to about 120 mg per day.

In certain aspects disclosed herein, step (b) comprises increasing the first dose to a second dose and administering the second dose of the compound to the subject for a second period of time in an amount ranging from about 40 mg per day to about 80 mg per day, and in various other aspects, step (b) comprises increasing the first dose to a second dose and administering the second dose of the compound to the subject for a second period of time in an amount ranging from about 40 mg per day to about 60 mg per day; and increasing the second dose to a third dose and administering the third dose of the compound to the subject for a third period of time in an amount ranging from about 80 mg per day to about 100 mg per day.

In one aspect of all methods, each of the first period, second period, and third period ranges from about 3 to about 9 days, such as about 3 to about 7 days, and in one aspect, each of the first period, second period, and third period is 3 days. In a further aspect disclosed herein, each of the first period and second period is 3 days and the third period is 7 days.

In one aspect of the disclosure, in the first period, the compound is administered in an amount ranging from about 20 mg to about 40 mg per day, such as about 20 mg per day or about 40 mg per day. In certain embodiments, in the second period, the compound is administered in an amount ranging from about 40 mg to about 80 mg per day, such as about 40 mg per day, about 60 mg per day, or about 80 mg per day. In further embodiments, in the third period, the compound is administered in an amount ranging from about 60 mg to about 120 mg per day, such as about 60 mg per day, about 80 mg per day, about 100 mg per day, or about 120 mg per day. In certain embodiments, a second dose is increased no more than 40 mg per day relative to the first dose and/or a third dose is increased no more than 40 mg per day relative to the second dose.

In certain aspects, the methods disclosed herein further comprise increasing the third dose to a fourth dose and administering the fourth dose of the compound to the subject for a fourth period of time in an amount of about 120 mg per day. In certain aspects, the methods comprise increasing a first dose of about 20 mg per day administered for a first time period of about 3 days to a second dose and administering the second dose of the compound to the subject for a second period of time in an amount of about 40 mg per day.

In certain aspects, in the methods disclosed herein wherein the second period is 3 days and the compound is administered in an amount of about 40 mg per day, the methods further comprise in step (b) increasing the second dose to a third dose and administering the third dose of the compound to the subject for a third period of time in an amount of about 60 mg per day; increasing the third dose to a fourth dose and administering the fourth dose of the compound to the subject for a fourth period of time in an amount of about 80 mg per day; and increasing the fourth dose to a fifth dose and administering the fifth dose of the compound to the subject for a fifth period of time in an amount of about 100 mg per day, wherein the maximum titrated dose of the compound is about 120 mg per day.

In certain aspects of the methods disclosed herein, the first period is 3 days and the compound is administered in an amount of about 20 mg per day, and the second period is about 3 days and the compound is administered in an amount of about 40 mg per day. In certain embodiments, the third period is 3 days and the compound is administered in an amount of about 80 mg per day, and the method further comprises administering to the subject for a fourth period about 120 mg of the compound per day.

In certain aspects of the methods disclosed herein, the first period is 3 days and the compound is administered in an amount of about 20 mg per day, the second period is 3 days and the compound is administered in an amount of about 40 mg per day, the third period is 7 days and the compound is administered in an amount of about 60 mg per day, and the method further comprises (d) administering to the subject for a fourth period ranging from about 3 to about 9 days about 80 mg of the compound of formula (I) or a pharmaceutically acceptable salt thereof per day, (e) administering to the subject for a fifth period ranging from about 3 to about 9 days about 100 mg of the compound of formula (I) or a pharmaceutically acceptable salt thereof per day; and (f) administering to the subject for a sixth period about 120 mg of the compound of formula (I) or a pharmaceutically acceptable salt thereof per day.

In various aspects of the disclosure, the pharmaceutically acceptable salt is a hydrochloride salt of formula (II). In certain aspects, the subject is a human aged 18 to 55 years old, and in certain aspects the subject is a human aged 55 to 75 years.

In certain aspects, the disease or condition relating to aberrant function or activity of T-type calcium channels is a psychiatric disorder, pain, tremor, seizures, epilepsy, or epilepsy syndrome. In certain aspects, the disorder is tremor, such as essential tremor. In certain embodiments, the compound of formula (I) or a pharmaceutically acceptable salt thereof is in a modified release dosage formulation comprising at least one modified release polymer, such as a modified release polymer chosen from hydroxypropyl methylcellulose, ethylcellulose, and polyacrylate polymers. In certain aspects of all embodiments disclosed herein, the pharmaceutically acceptable salt of formula (II) is crystalline Form C, and in certain aspects, the pharmaceutically acceptable salt of formula (II) is crystalline Form B.

In certain aspects of the methods disclosed herein, the method results in an EEG sigma frequency band reduction during non-rapid eye movement (NREM) sleep and/or an EEG gamma frequency band reduction during the awake state in an eyes open (EO) condition or an eyes closed (EC) condition in the subject. In certain embodiments, a ratio of the NREM sigma frequency band after administration of a dosage to a NREM sigma frequency band baseline ranges from about 0.4 to about 0.7, such as a ratio of from about 0.5 to about 0.6. In certain embodiments, the methods disclosed herein result in a NREM sigma frequency reduction in the subject when the subject is administered a dosage of the compound of formula (I) or a pharmaceutically acceptable salt thereof resulting in a $C_{max}$ of about 5 ng/mL to about 470 ng/mL, such as a $C_{max}$ of about 180 to about 300 ng/mL. In certain embodiments, the methods disclosed herein result in a NREM sigma frequency reduction in the subject when the subject is administered a dosage of the compound of formula (I) or a pharmaceutically acceptable salt thereof resulting in a $C_{ave}$ during the EEG recording of about 10 ng/mL to about 200 ng/mL, such as a $C_{ave}$ of about 12 to about 150 ng/mL. In certain embodiments, the methods disclosed herein result in an EO or EC gamma frequency band reduction in the subject when the subject is administered a dosage of the compound of formula (I) or a pharmaceutically acceptable salt thereof resulting in a $C_{max}$ of the compound of about 30 ng/mL to about 470 ng/mL, such as a $C_{max}$ of about 280 to about 470 ng/mL. In certain embodiments, the methods disclosed herein result in an EO or EC gamma frequency band reduction in the subject when the subject is administered a dosage of the compound of formula (I) or a pharmaceutically acceptable salt thereof resulting in a plasma concentration of about 75 ng/ml to about 310 ng/mL, such as a plasma concentration of about 90 to about 190 ng/mL.

Other objects and advantages will become apparent to those skilled in the art from a consideration of the ensuing Brief Description of the Figures, Detailed Description, Examples, and Claims.

DETAILED DESCRIPTION

Figure 1:
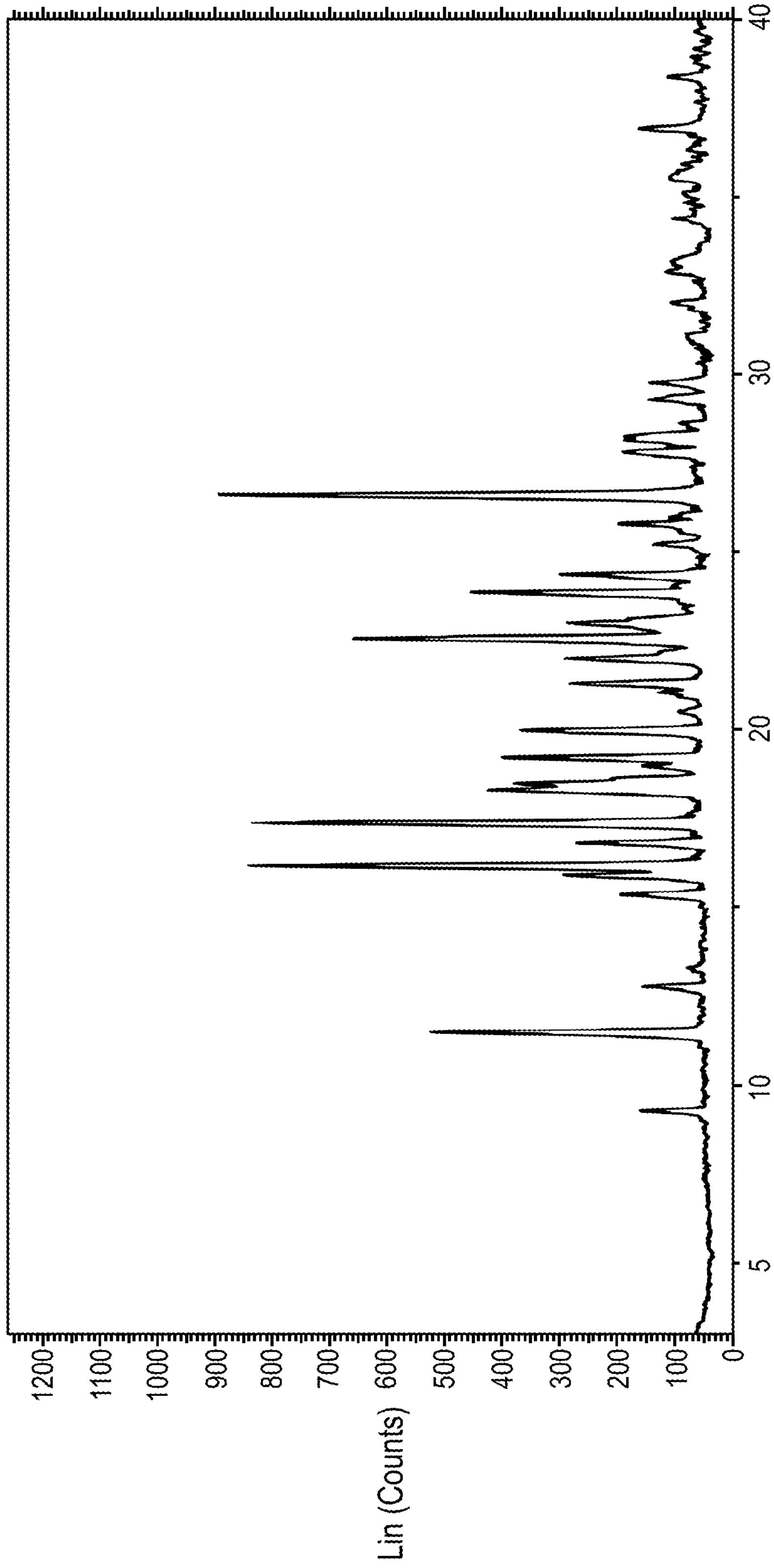
FIG. 1 is a X-ray Powder Diffraction (XRPD) pattern of Form C of the compound of formula (II).

This application discloses methods of preventing and/or treating a disease or condition relating to aberrant function or activity of a T-type calcium channel, such as psychiatric disorders (e.g., mood disorder (e.g., major depressive disorder)), pain, tremor (e.g., essential tremor), seizures (e.g., absence seizures), epilepsy, or an epilepsy syndrome (e.g., juvenile myoclonic epilepsy).

Also disclosed are the use of titrated dosage schedules for a compound of formula (I) or a pharmaceutically acceptable salt thereof to improve such methods of preventing and/or treating a disease or condition relating to aberrant function or activity of a T-type calcium channel. By using titrated dosage schedules, it was unexpectedly discovered that a titrated dose significantly larger than the maximum tolerated dose achieved without titration could be safely administered to a subject in need thereof. Similarly, by using a titrated dosage schedule, pharmacokinetic parameters, such as $C_{max}$ and $AUC_{24}$, could be increased significantly beyond the $C_{max}$ and/or $AUC_{24}$ values obtained when lower doses were administered without titration.

For example, as shown in the examples, a modified release dosage form (60 mg) that achieved a $C_{max}$ of about 130 ng/mL and/or an $AUC_{24}$ of about 1910 ng*h/mL following administration, was not tolerated in subjects. See Example 4. However, by using a titrated dosage schedule, the maximum dose tested (120 mg) unexpectedly resulted in a $C_{max}$ of at least about 390 ng/ml and an $AUC_{24}$ of at least about 4650 and was safely tolerated in patients. See Example 11. Furthermore, a maximum tolerated dose was not determined in the titrated scheme, indicating that the dose and pharmcokinetic parameters for formula (I) or a pharmaceutically acceptable salt thereof can be increased even further.

This finding was particularly surprising for the T-type calcium channel antagonist of formula (I) or a pharmaceutically acceptable salt thereof because this particular T-type calcium antagonist, while exhibiting state dependence, is much less state dependent than other T-type calcium antagonists, such as CX-8998, NBI-827104, and ABT-639, and has a significantly wider pharmacodynamic range. See, e.g., Tringham, E. et al., *T-type Calcium Channel Blockers That Attenuate Thalamic Burst Firing and Suppress Absence Seizures*, Sci. Transl. Med. 2012; 4(121):1-19 at 3, indicating that the compound of formula (I) "was 2.5- to 4-fold lower for the inactivated state of T-type channels than for the closed state." See also Siegrist, R. et al., *Structure—Activity Relationship, Drug Metabolism and Pharmacokinetics Properties Optimization*, and in Vivo *Studies of New Brain Penetrant Triple T-Type Calcium Channel Blockers*, J. Med. Chem. 2016; 59:10661-10675; PCT Published Application No. WO 2020/072773 at pages 27-28 (stating that CX-8998 "can have from about 29-fold to about 45-fold greater selectivity for Cav3 under hyperpolarizing conditions as compared to depolarizing conditions"); Lee, M. S. & Papapetropoulos, S., *CX-8998, a Potent, Selective T-type Calcium Channel Antagonist Dose—dependently Suppresses Seizures in the WAG/Rij Genetic Model of Absence Epilepsy*, Am. Acad. Neurol. 2018; Session P5, Abstract 281; Bezençon, O. et al., *Discovery of a Potent, Selective T-type Calcium Channel Blocker as a Drug Candidate for the Treatment of Generalized Epilepsy*, J. Med. Chem. 2017; 60:9769-9789; and Jarvis, M. F. et al., *A peripherally acting, selective T-type calcium channel blocker, ABT-639, effectively reduces nociceptive and neuropathic pain in rats*, Biochem. Pharmacol. 2014; 89(4):536-44.

Furthermore, other highly state-dependent T-type calcium channel inhibitors, such as CX-8998, achieved little to no benefit from titrated doses, resulting in a titrated daily dose of only 20 mg (see, e.g., Papapetropoulos et al., Frontiers in Neurology, 2019 and Papapetropoulos et al., Movement Disorders 2021), which dose is not notably greater than the highest non-titrated dose (16 mg) of the compound that was safely administered to patients. See, e.g., PCT Published Application No. WO 2020/072773 at page 220 ("Singles doses up to 16 mg were generally well tolerated . . . . Doses of 20 and 24 mg were less well tolerated because of poor concentration, headache, mood changes, anxiety, restlessness, and vivid dreams after evening dosing."). Thus, the fact that the dose of the formula (I) compound or a pharmaceutically acceptable salt thereof could be increased to at least twice the non-titrated, maximum tolerated dose of compound of formula (I) or a pharmaceutically acceptable salt thereof, was particularly surprising given that CX-8998 is substantially more state dependent than the compound of formula (I).

Thus, in one aspect of the present disclosure, for the compound of formula (I) or a pharmaceutically acceptable salt thereof, the maximum tolerated $C_{max}$ without titration is less than 130 ng/mL, such as between 30 and 130 ng/mL, and/or the maximum tolerated $AUC_{24}$ without titration is less than 2000 ng*h/mL, such as between 490 and 2000 ng*h/mL. Accordingly, in certain embodiments, by using the titrated dosage schedules disclosed herein, a $C_{max}$ is achieved that is greater than 130 ng/mL, such as ranging from about 180 to 300 ng/mL, from about 230 to 380 ng/mL, or from about 280 to 470 ng/mL and/or an $AUC_{24}$ is achieved that is greater than 2000 ng*h/mL, such as from about 2440 to 4070 ng*h/mL, from about 2820 to 4700 ng*h/mL, or from about 3480 to 5800 ng*h/mL. In certain embodiments of the disclosure, there are provided methods of titrating an initial dosee to at least about 1.5 times the maximum tolerated $C_{max}$ and/or the maximum tolerated $AUC_{24}$ achieved without titration, such as at least about 2 times, at least about 2.5 times, or at least about 3 times the maximum tolerated $C_{max}$ and/or $AUC_{24}$ achieved without titration.

In other aspects of the disclosure, the maximum tolerated dose achieved without titration is less than 60 mg, such as about 55 mg, about 50 mg, about 45 mg, or about 40 mg. Accordingly, in certain embodiments, the maximum titrated dosage is at least about 60 mg, such as, for example, at least about 70 mg, at least about 80 mg, at least about 90 mg, at least about 100 mg, at least at least about 110 mg, about 120 mg, at least about 130 mg, at least about 140 mg, at least about 150 mg, at least about 160 mg, at least about 170 mg, at least about 180 mg, at least about 190 mg, at least about 200 mg, at least about 210 mg, or at least about 220 mg. Accordingly, in certain embodiments of the disclosure, there are provided methods of titrating an initial dosage to at least about 2 times the maximum tolerated dose achieved without titration (e.g., about 2 times 40 mg, or a maximum titrated dosage of about 80 mg). In certain embodiments of the disclosure, there are provided methods of titrating an initial dosage to at least about 2.5 times the maximum tolerated dose achieved without titration, such as, for example, at least about 3 times, at least about 3.5 times, at least about 4 times, at least about 4.5 times, at least about 5 times, or at least about 5.5 times of a maximum tolerated dosage achieved without titration.

Methods are also presented for treating tremor (e.g., essential tremor, Parkinson's tremor, or cerebellar tremor) or epilepsy or epilepsy syndromes (e.g., absence seizures, juvenile myoclonic epilepsy, or a genetic epilepsy). Methods are also presented for treating mood disorders (e.g., depression, major depressive disorder, dysthymic disorder (e.g., mild depression), bipolar disorder (e.g., I and/or II), anxiety disorders (e.g., generalized anxiety disorder (GAD), social anxiety disorder), stress, post-traumatic stress disorder (PTSD), and/or compulsive disorders (e.g., obsessive compulsive disorder (OCD)). Methods are also presented that are useful for modulating the function and blocking a T-type calcium channel. Methods are also presented for treating pain (e.g., acute pain, chronic pain, neuropathic pain, inflammatory pain, nociceptive pain, central pain; e.g., thalamic pain; or migraine). Methods are also presented for treating ataxia (e.g., spinocerebellar ataxia, or spinocerebellar ataxia with CACNA1G mutations). Methods are also presented for treating tinnitus. Methods are also presented for treating a disorder of wakefulness.

Definitions

In general, the "effective amount" of a compound refers to an amount sufficient to elicit the desired biological response. As will be appreciated by those of ordinary skill in this art, the effective amount of a compound may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, the term "refractory" refers to a disease, disorder, or condition that does not readily yield or respond to therapy or treatment, or is not controlled by a therapy or treatment. In some embodiments, a disease, disorder, or condition described herein is refractory (e.g., refractory epilepsy or refractory absence seizures) and does not respond to standard therapy or treatment.

As used herein, a "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

The terms "disease", "disorder", and "condition" are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, stereoisomers thereof (e.g., enantiomers, diastereomers) and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate. In certain embodiments, a compound of formula (I) is a hydrochloric acid salt.

The term "modified-release polymer" refers to a polymer that is used in a formulation (e.g., tablets and capsules) to modify the release rate of the drug upon the administration to a subject. For example, a modified-release polymer is used to dissolve a drug over time in order to be released slower and steadier into the bloodstream. For example, a modified-release polymer is a controlled-release polymer. For example, a modified-release polymer or a controlled-release polymer is an HPMC polymer. In some embodiments, a modified-release polymer may include hydrophilic matrix polymers (e.g., hypromellose, HPMC (hydroxylpropyl methylcellulose)), hydrophobic matrix polymers (e.g., ethyl cellulose, ethocel), or polyacrylate polymers (e.g., Eudragit RL100, Eudragit RS100).

The term "diluent" as used herein refers to an excipient used to increase weight and improve content uniformity. For example, diluents include cellulose derivatives (e.g., microcrystalline cellulose), starches (e.g., hydrolyzed starches, and partially pregelatinized starches), anhydrous lactose, lactose monohydrate, di-calcium phosphate (DCP), sugar alcohols (e.g., sorbitol, xylitol and mannitol)).

The term "glidant" as used herein refers to an excipient used to promote powder flow by reducing interparticle friction and cohesion. For example, glidants include fumed silica (e.g., colloidal silicon dioxide), talc, and magnesium carbonate.

The term "lubricant" as used herein refers to an excipient used to prevent ingredients from clumping together and from sticking to the tablet punches or capsule filling machine. Lubricants are also used to ensure that tablet formation and ejection can occur with low friction between the solid and die wall. For example, lubricants include magnesium stearate, calcium stearate, stearic acid, talc, silica, and fats (e.g., vegetable stearin).

The term "coating" as used herein refers to an excipient to protect tablet ingredients from deterioration by moisture in the air and make large or unpleasant-tasting tablets easier to swallow. These and other exemplary substituents are described in more detail in the Detailed Description, Examples, and Claims. The disclosure is not intended to be limited in any manner by the above exemplary listing of substituents.

Methods of Treating a Disease or Condition Relating to Aberrant Function or Activity of a T-Type Calcium Channel In one aspect, the present disclosure provides a method of treating a disease or condition relating to aberrant function or activity of a T-type calcium channel in a subject in need thereof, the method comprising administering (e.g., once, twice, three times) daily to the subject a therapeutically effective amount of the compound of formula (I):

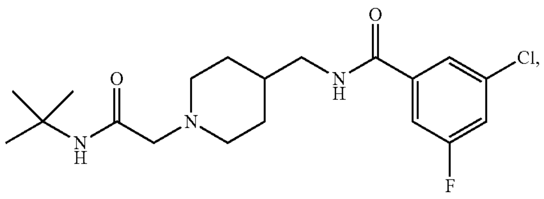 [SMILES: CC(C)(C)NC(=O)CN1CCC(CNC(=O)c2cc(F)cc(Cl)c2)CC1]

or a pharmaceutically acceptable salt (e.g., co-crystal) or solvate thereof, for example, a compound of formula (II):

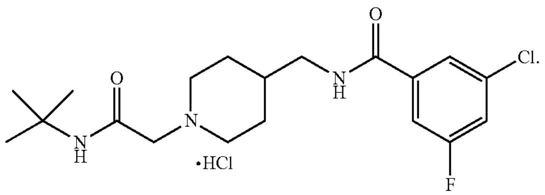

Formula (I) may also be referred to as N-((1-(2-(tert-butylamino)-2-oxoethyl)piperidin-4-yl)methyl)-3-chloro-5-fluorobenzamide, while formula (II) may be referred to as N-((1-(2-(tert-butylamino)-2-oxoethyl)piperidin-4-yl)methyl)-3-chloro-5-fluorobenzamide hydrochloride.

Disclosed herein are methods of treating a disease or condition relating to aberrant function or activity of a T-type calcium channel, comprising administering a titrated dose such that the end or maintenance dosage exceeds an initial dosage or a dosage at which adverse events are likely to be experienced absent titration (a maximum tolerated dosage achieved without titration). As used herein, administering a tritrated dose refers to the practice of beginning with a low dosage and escalating to one or more higher dosages. For example, in certain embodiments, disclosed herein is a method of treating a disease or condition relating to aberrant function or activity of a T-type calcium channel in a subject in need thereof comprising (a) administering a first dose, such as a dose of about 20 mg or about 40 mg, of a compound of formula (I) or a pharmaceutically acceptable salt thereof to the subject for a first period of time, wherein following administration of the first dose of the compound for the first period of time the subject has a maximum plasma drug concentration ($C_{max}$) ranging from about 30 ng/mL to about 130 ng/mL and/or an area under the plasma concentration-time curve from time of administration to 24 hours after administration ($AUC_{24}$) ranging from about 490 ng*h/mL to about 2030 ng*h/mL; (b) increasing the amount of the compound in the first dose and administering one or more increased doses of the compound to the subject to arrive at a maximum titrated dose; and (c) administering the maximum titrated dose of the compound to the subject to maintain in the subject a $C_{max}$ ranging from about 280 ng/mL to about 470 ng/mL and/or an $AUC_{24}$ ranging from about 3480 ng*h/mL to about 5800 ng*h/mL. Typically, each dose is administered daily, preferably once a day, however, the frequency of administration may be altered as long as the desired $C_{max}$ and/or $AUC_{24}$ values are achieved, as discussed in other sections of this application.

For instance, in certain embodiments, step (b) comprises increasing the first dose to a second dose, such as for example, a dose of about 40 to about 80 mg, and administering the second dose of the compound to the subject for a second period of time, wherein following administration of the second dose of the compound for the second period of time, the subject has a $C_{max}$ ranging from about 80 ng/mL to about 300 ng/mL, such as from about 80 ng/mL to about 220 ng/mL, from about 80 ng/mL to about 130 ng/mL, or about 130 ng/mL to about 300 ng/mL, and/or an $AUC_{24}$ ranging from about 1220 ng*h/mL to about 4070 ng*h/mL, such as an $AUC_{24}$ ranging from about 1220 ng*h/mL to about 3330 ng*h/mL or from about 1220 ng*h/mL to about 2030 ng*h/mL. In certain embodiments, step (b) may further comprise increasing the second dose to a third dose, such as a dose ranging from about 60 mg to about 100 mg, and administering the third dose of the compound to the subject for a third period of time, wherein following administration of the third dose, the subject has a $C_{max}$ ranging from about 130 ng/mL to about 380 ng/mL, such as from 130 ng/mL to about 220 ng/mL, from about 180 ng/mL to about 300 ng/mL, or from 230 ng/mL to about 380 ng/mL and/or an $AUC_{24}$ ranging from about 2000 ng*h/mL to about 4700 ng*h/mL, such as from about 2000 ng*h/mL to about 3330 ng*h/mL, from about 2440 ng*h/mL to about 4070 ng*h/mL, or from about 2820 ng*h/mL to about 4700 ng*h/mL.

Also disclosed herein are embodiments further comprising increasing the third dose to a fourth dose, such as a dose of about 80 mg to about 100 mg, and administering the fourth dose of the compound to the subject for a fourth period of time, wherein following administration of the fourth dose of the compound for the fourth period of time, the subject has a $C_{max}$ ranging from about 180 ng/mL to about 380 ng/mL, such as about 180 ng/mL to about 300 ng/mL or about 230 to about 380 ng/mL and/or an $AUC_{24}$ ranging from about 2440 ng*h/mL to about 4700 ng*h/mL, such as from about 2440 ng*mL/mL to about 4070 ng*h/mL or about 2820 ng*mL to about 4700 ng*h/mL. In certain aspects, the methods disclosed herein may further comprise increasing the fourth dose to a fifth dose, such as a dose of about 100 mg, and administering the fifth dose of the compound to the subject for a fifth period of time, wherein following administration of the fifth dose of the compound for the fifth period of time, the subject has a $C_{max}$ ranging from about 230 ng/mL to about 380 ng/mL and an $AUC_{24}$ ranging from about 2820 ng*h/mL to about 4700 ng*h/mL.

In certain embodiments of the titrated dosing schedules disclosed herein, it is possible to increase the maximum titrated dose to maintain in the subject a $C_{max}$ greater than 470 ng/mL and/or an $AUC_{24}$ greater than 5800 ng*h/mL, provided the subject is able to safely tolerate the higher dose. For example, in certain embodiments, the method comprises one or more additional titration steps, to achieve a maximum titrated dose that is administered to the subject to maintain a $C_{max}$ ranging from about 450 ng/mL to about 750 ng/mL, including, for example, about 450 ng/mL to about 650 ng/mL, about 450 ng/mL to about 550 ng/mL, or about 450 ng/mL to about 500 ng/mL, and/or an $AUC_{24}$ ranging from about 5500 ng*h/mL to about 9500 ng*h/mL, including, for example, about 5500 ng*h/mL to about 8500 ng*h/mL, 5500 ng*h/mL to about 7500 ng*h/mL, or about 5500 ng*h/mL to about 6500 ng*h/mL.

Also disclosed herein is a method of treating a disease or condition relating to aberrant function or activity of a T-type calcium channel in a subject in need of treatment comprising (a) administering to the subject for a first period, about 5 mg to about 40 mg per day of a compound of formula (I) or a pharmaceutically acceptable salt thereof; (b) administrating to the subject for a second period, about 10 mg to about 100 mg per day of the compound of formula (I) or a pharmaceutically acceptable salt thereof; and (c) administrating to the subject for a third period, about 20 mg to about 120 mg per day of the compound of formula (I) or a pharmaceutically acceptable salt thereof. Typically, each of the first period, second period, and third period range from about 3 to about 9 days. However, shorter or longer periods of time may be used depending on the subject.

In certain embodiments, the subject does not experience adverse events at any of the dosage levels in the titrated dosage schedule. In certain embodiments, absent administering a first dosage level for a first dosing period (e.g., about 5 mg to about 40 mg), the subject would experience adverse events at the second dosage level administered during the second dosing period (e.g., about 10 mg to about 100 mg, such as at least about 60 mg to about 100 mg). In certain embodiments, absent administering the first and second dosage level during the first and second dosing period, a subject would experience adverse events at the third dosage level administered during the third dosing period (e.g., about 20 mg to about 120 mg, such as at least about 60 mg to about 120 mg).

In certain embodiments, wherein a subject would be likely to experience adverse events at the second dosage level administered during the second dosing period absent administering the first dosage level during the first dosing period, the dosage may continue to be titrated to a dosage level that is greater than the second dosage level administered during the second dosing period, such as a dosage level that is at least about 25% greater, at least about 50% greater, at least about 75% greater, at least about 100% greater, at least about 125% greater, at least about 150% greater, at least about 175% greater, at least about 200% greater, at least about 250% greater, or at least about 300% greater than the dosage level at which adverse events are likely to occur without titration.

In certain aspects of all embodiments disclosed herein, the time period of administration, such as the first, second, third, fourth or fifth period of time, may range from about 3 to about 9 days, such as, for example, 3, 4, 5, 6, 7, 8, or 9 days.

In certain aspects, the dosage increase relative to the prior dose does not increase more than 40 mg per day. For instance, in certain embodiments, the second dose is increased no more than 40 mg per day relative to the first dose, and in certain aspects, the third dose is increased no more than 40 mg per day relative to the second dose.

In another aspect, the present disclosure provides a method of treating a disease or condition relating to aberrant function or activity of a T-type calcium channel in a subject in need thereof, the method comprising administering (e.g., once, twice, three times) daily to the subject up to about 120 mg (e.g., from about 5 mg to about 120 mg, from about 10 mg to about 120 mg, from about 15 mg to about 120 mg, from about 20 mg to about 120 mg, from about 40 mg to about 120 mg, from about 5 mg to about 100 mg, from about 10 mg to about 100 mg, from about 15 mg to about 100 mg, from about 20 mg to about 100 mg, from about 40 mg to about 100 mg, from about 5 mg to about 80 mg, from about 10 mg to about 80 mg, from about 15 mg to about 80 mg, from about 20 mg to about 80 mg, from about 40 mg to about 80 mg, from about 5 mg to about 60 mg, from about 10 mg to about 60 mg, from about 15 mg to about 60 mg, from about 20 mg to about 60 mg, or from about 40 mg to about 60 mg) of the compound of formula (I) or a pharmaceutically acceptable salt thereof (e.g., the compound of formula (II)).

In another aspect, the present disclosure provides a method of treating a disease or condition relating to aberrant function or activity of T-type calcium channels in a subject in need thereof, the method comprising:

(a) administrating to the subject once daily for a first period (e.g., 3, 4, 5, 6, 7, 8, or 9 days), 5 mg of the compound of formula (I) or a pharmaceutically acceptable salt thereof (e.g., the compound of formula (II));

(b) administrating to the subject once daily for a second period (e.g., 3, 4, 5, 6, 7, 8, or 9 days), 10 mg of the compound of formula (I) or a pharmaceutically acceptable salt thereof (e.g., the compound of formula (II)); and (c) administrating to the subject once daily for a third period (e.g., 3, 4, 5, 6, 7, 8, or 9 days), 20 mg of the compound of formula (I) or a pharmaceutically acceptable salt thereof (e.g., the compound of formula (II)).

In another aspect, the present disclosure provides a method of treating a disorder in a subject in need thereof, the method comprising:

(a) administrating to the subject for a first period (e.g., 3, 5, 6, 7, 8, or 9 days), 20-40 mg per day of the compound of formula (I) or a pharmaceutically acceptable salt thereof (e.g., the compound of formula (II));

(b) administrating to the subject for a second period (e.g., 3, 5, 6, 7, 8, or 9 days), 40-80 mg per day of the compound of formula (I) or a pharmaceutically acceptable salt thereof (e.g., the compound of formula (II)); and (c) administrating to the subject for a third period (e.g., 3, 4, 5, 6, 7, 8, or 9 days), 60-120 mg per day of the compound of formula (I) or a pharmaceutically acceptable salt thereof (e.g., the compound of formula (II)).

In some embodiments, the method further comprises (d) administering to the subject for a fourth period (e.g., 3, 4, 5, 6, 7, 8, or 9 days), 80-120 mg per day of the compound of formula (I) or a pharmaceutically acceptable salt thereof (e.g., the compound of formula (II)).

In other embodiments, the method further comprises (e) administering to the subject for a fifth period (e.g., 3, 4, 5, 6, 7, 8, or 9 days), 100-120 mg per day of the compound of formula (I) or a pharmaceutically acceptable salt thereof (e.g., the compound of formula (II)).

In certain embodiments, the method further comprises (f) administering to the subject for a sixth period (e.g., 3, 4, 5, 6, 7, 8, or 9 days), 120 mg per day of the compound of formula (I) or a pharmaceutically acceptable salt thereof (e.g., the compound of formula (II)).

For instance, in certain embodiments there is disclosed a method of treating a disease or condition relating to aberrant function or activity of a T-type calcium channel in a subject in need thereof comprising (a) administrating to the subject for a first period ranging from about 3 to about 9 days, about 5 mg to about 40 mg per day of a compound of formula (I) or a pharmaceutically acceptable salt thereof, such as 20 mg or 40 mg per day; (b) administrating to the subject for a second period ranging from about 3 to about 9 days, about 10 mg to about 100 mg per day of the compound of formula (I) or a pharmaceutically acceptable salt thereof, such as 40 mg, 60 mg, or 80 mg per day; and (c) administrating to the subject for a third period ranging from about 3 to about 9 days, about 20 mg to about 120 mg per day of the compound of formula (I) or a pharmaceutically acceptable salt thereof, such as 60 mg, 80 mg, 100 mg, or 120 mg per day.

In certain aspects, disclosed herein is a method of treating a disease or condition relating to aberrant function or activity of T-type calcium channels in a subject in need thereof comprising (a) administering a first dose of about 20 mg to about 40 mg per day of a compound of formula (I) or a pharmaceutically acceptable salt thereof to a subject once daily for a first time period; (b) increasing the amount of the compound in the first dose and administering one or more increased doses of the compound to the subject to arrive at a maximum titrated dose of about 80 mg to about 120 mg per day; and (c) administering the maximum titrated dose to the subject once daily as needed.

In various embodiments of the disclosure, the methods disclosed herein comprise (a) administering a first dose of 20 mg per day for a first period of time of 3 days, (b) administering a second dose of 40 mg per day for a second period of time of 3 days, (c) administering a third dose of 60 mg per day for a third period of time of 7 days; (d) administering a fourth dose of 80 mg per day for a fourth period of time of 7 days; (e) administering a fifth dose of 100 mg per day for a fifth period of time of 7 days; and (f) thereafter administering a sixth dose of 120 mg per day as needed. In various other embodiments, the methods disclosed herein comprise (a) administering a first dose of 20 mg per day for a first period of time of 3 days, (b) administering a second dose of 40 mg per day for a second period of time of 3 days, (c) administering a third dose of 80 mg per day for a third period of time of 3 days; and (d) administering a fourth dose of 120 mg per day as needed.

In certain embodiments there is disclosed a method of treating a disease or condition relating to aberrant function or activity of T-type calcium channels in a subject in need thereof comprising (a) administrating to the subject for a first period of 3 days about 20 mg per day of a compound of formula (I) or a pharmaceutically acceptable salt thereof; (b) administrating to the subject for a second period of about 3 days about 40 mg per day of the compound; (c) administrating to the subject for a third period of about 3 days about 60 mg per day of the compound; (d) administrating to the subject for a fourth period of about 3 days about 80 mg per day of the compound; (e) administrating to the subject for a fifth period of about 3 days about 100 mg per day of the compound; and (f) administrating to the subject for a sixth period of time about 120 mg per day of the compound. Instead of every 3 days, the doses can also be administered every 4, 5, or 6 days.

Also disclosed herein is a method of treating a disease or condition relating to aberrant function or activity of T-type calcium channels in a subject in need thereof comprising (a) administrating to the subject for a first period of 7 days about 20 mg per day of a compound of formula (I) or a pharmaceutically acceptable salt thereof; (b) administrating to the subject for a second period of about 7 days about 40 mg per day of the compound; (c) administrating to the subject for a third period of about 7 days about 60 mg per day of the compound; (d) administrating to the subject for a fourth period of about 7 days about 80 mg per day of the compound; (e) administrating to the subject for a fifth period of about 7 days about 100 mg per day of the compound; and (f) administrating to the subject for a sixth period of time about 120 mg per day of the compound.

In certain embodiments there is disclosed a method of treating a disease or condition relating to aberrant function or activity of a T-type calcium channel in a subject in need thereof comprising (a) administrating to the subject for a first period of 3 days about 40 mg per day of a compound of formula (I) or a pharmaceutically acceptable salt thereof; (b) administrating to the subject for a second period of about 3 days about 80 mg per day of the compound; and (c) administrating to the subject for a third period about 120 mg per day of the compound. Instead of every 3 days, the doses can also be administered every 4, 5, or 6 days.

Also disclosed herein is a method of treating a disease or condition relating to aberrant function or activity of a T-type calcium channel in a subject in need thereof comprising (a) administrating to the subject for a first period of 7 days about 40 mg per day of a compound of formula (I) or a pharmaceutically acceptable salt thereof; (b) administrating to the subject for a second period of about 7 days about 80 mg per day of the compound; and (c) administrating to the subject for a third period about 120 mg per day of the compound.

In some embodiments, the subject is a human of age from birth to 100 years of age, such as from 10 to 90 years, from 20 to 70 years, from 18 to 55 years, or from 55-75 years of age.

In various aspects, the methods disclosed herein result in an EEG sigma frequency band reduction during NREM sleep in the subject, such as a NREM sigma band frequency reduction from a baseline of about 0.4 to 0.7, such as about 0.5 to about 0.6, or about 0.5. In certain embodiments, the methods disclosed herein result in an EEG gamma frequency band reduction during wake in an EO condition or an EC condition the subject, such as a gamma frequency band reduction as compared to a baseline gamma frequency band of at least about 25%, such as, for example, about 50% reduction.

In certain embodiments, the methods disclosed herein result in an EEG sigma frequency reduction during NREM sleep and/or an EEG gamma frequency band reduction during an EO or an EC condition in the subject when the subject is administered a dosage of the compound of formula (I) or a pharmaceutically acceptable salt thereof resulting in a $C_{max}$ of from about 30 ng/mL to about 470 ng/mL, such as a $C_{max}$ ranging from about 30 to about 50 ng/mL, from about 80 to about 130 ng/mL, from about 130 to about 222 ng/mL, from about 180 to about 300 ng/mL, from about 230 to 380 ng/mL, or from about 280 to about 470 ng/mL. In certain embodiments, the methods disclosed herein result in an EEG sigma frequency reduction during NREM sleep and/or an EEG gamma frequency band reduction during an EO or an EC condition in the subject when the subject is administered a dosage of the compound of formula (I) or a pharmaceutically acceptable salt thereof resulting in an $AUC_{24}$ ranging from about 490 ng*h/mL to about 5800 ng*h/mL, such as an $AUC_{24}$ ranging from about 490 to 820 ng*h/mL, from about 1220 to 2030 ng*h/mL, from about 2000 to 3330 ng*h/mL, from about 2440 to 4070 ng*h/mL, from about 2820 to 4700 ng*h/mL, or from about 3480 to 5800 ng*h/mL.

In certain embodiments, the methods disclosed herein result in a NREM sigma frequency reduction in the subject when the subject is administered a dosage of the compound of formula (I) or a pharmaceutically acceptable salt thereof resulting in a $C_{max}$ of about 5 ng/mL to about 470 ng/mL, such as a $C_{max}$ of about 180 to about 300 ng/mL. In certain embodiments, the methods disclosed herein result in a NREM sigma frequency reduction in the subject when the subject is administered a dosage of the compound of formula (I) or a pharmaceutically acceptable salt thereof resulting in an average plasma concentration ($C_{ave}$) during the EEG recording (i.e., over a period of about 24 hours) of about 10 ng/mL to about 200 ng/mL, such as a $C_{ave}$ of about 12 to about 150 ng/mL. In certain embodiments, the methods disclosed herein result in an EO or EC gamma frequency band reduction in the subject when the subject is administered a dosage of the compound of formula (I) or a pharmaceutically acceptable salt thereof resulting in a $C_{max}$ of the compound of about, such as a $C_{max}$ of about 280 to about 470 ng/mL. In certain embodiments, the methods disclosed herein result in an EO or EC gamma frequency band reduction in the subject when the subject is administered a dosage of the compound of formula (I) or a pharmaceutically acceptable salt thereof resulting in a plasma concentration of about 75 ng/ml to about 310 ng/mL, such as a plasma concentration of about 90 to about 190 ng/mL.

In other embodiments, the disease or condition relating to aberrant function or activity of a T-type calcium channel is selected from the group consisting of psychiatric disorders (e.g., mood disorder (e.g., major depressive disorder)), pain, tremor (e.g., essential tremor), seizures (e.g., absence seizures), and epilepsy or an epilepsy syndrome (e.g., juvenile myoclonic epilepsy).

It certain aspects of all embodiments of titrated dosing schedules disclosed herein, it is possible to increase the maximum titrated dose, including, for example, increasing the maximum titrated dose above 120 mg in one or more additional titration steps, provided the subject is able to safely tolerate the higher dose.

In certain aspects of all of the embodiments of titrated dosing schedules disclosed herein, the maximum titrated dosage achieved is greater than 60 mg, such as about 80 mg, about 100 mg, about 120 mg, about 130 mg, about 140 mg, about 150 mg, about 160 mg, about 170 mg, about 180 mg, about 190 mg, about 200 mg, about 210 mg, or about 220 mg.

In certain aspects of all of the embodiments of titrated dosing schedules disclosed herein, the maximum titrated dosage is reached in 42 days or less, such as 31 days or less, 28 days or less, 18 days or less, 10 days or less, or 7 days or less. In certain embodiments, the maximum titrated dosage is reached in about 10 to about 42 days, such as, for example, about 36-42 days, about 22-28 days, about 16-18 days, or about 10-12 days.

Dosage Forms and Compositions

In some embodiments, the compound of formula (I) or a pharmaceutically acceptable salt thereof, e.g., the compound of formula (II) may be in a dosage form or in a pharmaceutical composition.

In some embodiments, a composition that can be used in a method described herein may be a pharmaceutical composition comprising the compound of formula (I) or a pharmaceutically acceptable salt thereof, and an excipient that functions to modify the release rate of the compound of formula (I) or a pharmaceutically acceptable salt thereof. In some embodiments, the pharmaceutical composition may be a swellable core technology formulations.

In certain embodiments, a dosage form that can be used in a method described herein may be an oral dosage form comprising: the compound of formula (I) or a pharmaceutically acceptable salt thereof (e.g., the compound of formula (II)); and a modified-release polymer (e.g., a controlled-release polymer, hydrophilic matrix polymers, e.g., an HPMC polymer, hydrophobic matrix polymers (e.g., ethyl cellulose, ethocel), or polyacrylate polymers (e.g., Eudragit RL100, Eudragit RS100)).

In other embodiments, a dosage form that can be used in a method described herein may be a dosage form or composition comprising the compound of formula (I) or a pharmaceutically acceptable salt thereof (e.g., the compound of formula (II)) and a modified-release polymer (e.g., a controlled-release polymer, hydrophilic matrix polymers, e.g., an HPMC polymer, hydrophobic matrix polymers (e.g., ethyl cellulose, ethocel), or polyacrylate polymers (e.g., Eudragit RL100, Eudragit RS100)), for example, in an amount sufficient to modify the release rate of the compound of formula (I) or a pharmaceutically acceptable salt thereof (e.g., the compound of formula (II)) upon an administration to the subject.

In some embodiments, the dosage form may comprises from about 0.9% by weight to about 40% by weight (e.g., from about 0.9% by weight to about 30%, from about 1% by weight to about 25% by weight, from about 2% by weight to about 25% by weight, from about 3% by weight to about 20% by weight, from about 4% by weight to about 20% by weight, from about 5% by weight to about 20% by weight, from about 5% by weight to about 15% by weight, from about 5% by weight to about 10% by weight, or about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 40% by weight) of the compound of formula (I) or a pharmaceutically acceptable salt thereof (e.g., the compound of formula (II)). In some embodiments, the dosage form comprises about 30% by weight to about 40% by weight of the compound of formula (I) or a pharmaceutically acceptable salt thereof (e.g., the compound of formula (II)).

In some embodiments, the dosage form may comprises from about 14% by weight to about 25% by weight of the compound of formula (I) or a pharmaceutically acceptable salt thereof (e.g., the compound of formula (II)). In some embodiments, the dosage form comprises from about 19% by weight to about 20% by weight of the compound of formula (I) or a pharmaceutically acceptable salt thereof (e.g., the compound of formula (II)). In some embodiments, the dosage form comprises from about 21% by weight to about 22% by weight of the compound of formula (I) or a pharmaceutically acceptable salt thereof (e.g., the compound of formula (II)). In some embodiments, the dosage form comprises from about 4% by weight to about 15% by weight of the compound of formula (I) or a pharmaceutically acceptable salt thereof (e.g., the compound of formula (II)). In some embodiments, the dosage form comprises from about 4% by weight to about 10% by weight of the compound of formula (I) or a pharmaceutically acceptable salt thereof (e.g., the compound of formula (II)). In some embodiments, the dosage form comprises form about 4% by weight to about 5% by weight of the compound of formula (I) or a pharmaceutically acceptable salt thereof (e.g., the compound of formula (II)). In some embodiments, the dosage form comprises from about 5% by weight to about 6% by weight of the compound of formula (I) or a pharmaceutically acceptable salt thereof (e.g., the compound of formula (II)). In some embodiments, the dosage form comprises from about 9% by weight to about 10% by weight of the compound of formula (I) or a pharmaceutically acceptable salt thereof (e.g., the compound of formula (II)).

In other embodiments, a dosage form that can be used in a method described herein may be a dosage form or composition comprising from about 1 mg to about 60 mg (e.g., about 5 mg, about 10 mg, about 15 mg, about 20 mg, about 25 mg, about 30 mg, about 35 mg, about 40 mg, about 45 mg, about 50 mg, about 55 mg, or about 60 mg) of the compound of formula (I) or a pharmaceutically acceptable salt thereof (e.g., the compound of formula (II)) and a modified-release polymer (e.g., a controlled-release polymer, hydrophilic matrix polymers, e.g., an HPMC polymer, hydrophobic matrix polymers (e.g., ethyl cellulose, ethocel), or polyacrylate polymers (e.g., Eudragit RL100, Eudragit RS100)), for example, in an amount sufficient to modify the release rate of the compound of formula (I) or a pharmaceutically acceptable salt thereof (e.g., the compound of formula (II)) upon an administration to the subject.

In other embodiments, the dosage form comprises from about 4 mg to about 6 mg (e.g., about 5 mg) of the compound of formula (I) or a pharmaceutically acceptable salt thereof (e.g., the compound of formula (II)). In certain embodiments, the dosage form comprises from about 15 mg to about 25 mg (e.g., about 20 mg) of the compound of formula (I) or a pharmaceutically acceptable salt thereof (e.g., the compound of formula (II)). In some embodiments, the dosage form comprises from about 5 mg to about 15 mg (e.g., about 10 mg) of the compound of formula (I) or a pharmaceutically acceptable salt thereof (e.g., the compound of formula (II)). In other embodiments, the dosage form comprises from about 25 mg to about 35 mg (e.g., about 30 mg) of the compound of formula (I) or a pharmaceutically acceptable salt thereof (e.g., the compound of formula (II)). In certain embodiments, the dosage form comprises from about 35 mg to about 45 mg (e.g., about 40 mg) of the compound of formula (I) or a pharmaceutically acceptable salt thereof (e.g., the compound of formula (II)).

In some embodiments, the dosage form comprises from about 55 mg to 65 mg of a modified-release polymer (e.g., an HPMC polymer). In some embodiments, the dosage form comprises from about 10% by weight to about 70% by weight of the modified-release polymer (e.g., an HPMC polymer). In some embodiments, the dosage form comprises from about 50% by weight to about 60% by weight of the modified-release polymer (e.g., an HPMC polymer).

In some embodiments, the dosage form further comprises a diluent. In some embodiments, the diluent comprises microcrystalline cellulose. In some embodiments, the dosage form comprises from about 15 mg to 40 mg (e.g., from about 15 mg to about 25 mg, from about 20 mg to about 25 mg, from about 25 mg to about 30 mg, from about 30 mg to about 40 mg) microcrystalline cellulose. In some embodiments, the dosage form comprises from about 15 mg to about 25 mg microcrystalline cellulose. In some embodiments, the dosage form comprises from about 30 mg to about 40 mg microcrystalline cellulose. In some embodiments, the dosage form comprises from about 15% to about 35% by weight (e.g., from about 15% to about 20%, from about 20% to about 25%, from 25% to about 30%, from 30% to about 35% by weight) microcrystalline cellulose.

In some embodiments, the dosage form further comprises a glidant. In some embodiments, the glidant comprises colloidal silicon dioxide. In some embodiments, the dosage form further comprises a lubricant. In some embodiments, the lubricant comprises magnesium stearate. In some embodiments, the dosage form further comprises a coating.

In some embodiments, about 80% of the compound of formula (I) or a pharmaceutically acceptable salt is released within 7 hours upon administration to a subject. In certain embodiments, about 80% of the compound of formula (I) or a pharmaceutically acceptable salt thereof is released in 7 hours using USP apparatus type-I, media containing 900 mL 0.1 M HCl, and a paddle speed of 100 rpm.

In some embodiments, the dosage form, upon administration to a subject, has a reduced $C_{max}$ value than a reference oral dosage form (e.g., a dosage form with any intended release rate profile e.g., modified release rate profile, a dosage form that does not have a modified release rate profile, a dosage form that does not have a modified-release polymer, e.g., an HPMC polymer). In some embodiments, the dosage form, upon administration to a subject, has a greater $t_{max}$ value than a reference oral dosage form (e.g., a dosage form with any intended release rate profile e.g., modified release rate profile, a dosage form that does not have a modified release rate profile, a dosage form that does not have a modified-release polymer, e.g., an HPMC polymer).

In other embodiments, the dosage form is administered to a patient once daily. In certain embodiments, the dosage form is administered to a patient twice daily. In some embodiments, the dosage form is a tablet. In other embodiments, the dosage form is a capsule. In certain embodiments, the dosage form is a suspension.

In some embodiments, a dosage form that can be used in a method described herein may be an oral dosage form (e.g., particulate) comprising: from about 15 mg to 25 mg of the compound of formula (I) or a pharmaceutically acceptable salt thereof (e.g., the compound of formula (II)); and from about 55 mg to 65 mg of an HPMC polymer.

In other embodiments, a dosage form that can be used in a method described herein may be an oral dosage form (e.g., particulate) comprising from about 14% by weight to about 25% by weight of the compound of formula (I) or a pharmaceutically acceptable salt thereof (e.g., the compound of formula (II)); and from about 53% to about 64% by weight of an HPMC polymer.

In certain embodiments, a dosage form that can be used in a method described herein may be an oral dosage form (e.g., particulate) comprising from about 3 mg to 8 mg of the compound of formula (I) or a pharmaceutically acceptable salt thereof (e.g., the compound of formula (II)); and from about 55 mg to 65 mg of an HPMC polymer.

In some embodiments, a dosage form that can be used in a method described herein may be an oral dosage form (e.g., particulate) comprising from about 3% by weight to about 8% by weight of the compound of formula (I) or a pharmaceutically acceptable salt thereof (e.g., the compound of formula (II)); and from about 53% to about 64% by weight of an HPMC polymer.

In other embodiments, a dosage form that can be used in a method described herein may be an oral (e.g., particulate) composition comprising the compound of formula (I) or a pharmaceutically acceptable salt thereof (e.g., the compound of formula (II)); and a modified-release polymer (e.g., a controlled-release polymer, e.g., an HPMC polymer as a hydrophilic matrix polymer).

In some embodiments, the composition comprises from about 0.9% by weight to about 40% by weight of the compound of formula (I) or a pharmaceutically acceptable salt thereof (e.g., the compound of formula (II)). In some embodiments, the composition comprises from about 14% by weight to about 25% by weight of the compound of formula (I) or a pharmaceutically acceptable salt thereof (e.g., the compound of formula (II)). In some embodiments, the composition comprises about 19% by weight to about 20% by weight of the compound of formula (I) or a pharmaceutically acceptable salt thereof (e.g., the compound of formula (II)). In some embodiments, the composition comprises about 21% by weight to about 22% by weight of the compound of formula (I) or a pharmaceutically acceptable salt thereof (e.g., the compound of formula (II)). In some embodiments, the composition comprises from about 4% by weight to about 15% by weight of the compound of formula (I) or a pharmaceutically acceptable salt thereof (e.g., the compound of formula (II)). In some embodiments, the composition comprises from about 4% by weight to about 10% by weight of the compound of formula (I) or a pharmaceutically acceptable salt thereof (e.g., the compound of formula (II)). In some embodiments, the composition comprises about 4% by weight to about 5% by weight of the compound of formula (I) or a pharmaceutically acceptable salt thereof (e.g., the compound of formula (II)). In some embodiments, the composition comprises about 5% by weight to about 6% by weight of the compound of formula (I) or a pharmaceutically acceptable salt thereof (e.g., the compound of formula (II)). In some embodiments, the composition comprises about 9% by weight to about 10% by weight of the compound of formula (I) or a pharmaceutically acceptable salt thereof (e.g., the compound of formula (II)).

In some embodiments, the composition comprises from about 1 mg to about 60 mg (e.g., about 5 mg, about 10 mg, about 15 mg, about 20 mg, about 25 mg, about 30 mg, about 35 mg, about 40 mg, about 45 mg, about 50 mg, about 55 mg, or about 60 mg) of the compound of formula (I) or a pharmaceutically acceptable salt thereof (e.g., the compound of formula (II)). In certain embodiments, the composition comprises from about 4 mg to about 6 mg (e.g., about 5 mg) of the compound of formula (I) or a pharmaceutically acceptable salt thereof (e.g., the compound of formula (II)). In other embodiments, the composition comprises from about 15 mg to about 25 mg (e.g., about 20 mg) of the compound of formula (I) or a pharmaceutically acceptable salt thereof (e.g., the compound of formula (II)).

In some embodiments, the composition comprises a diluent. In some embodiments, the diluent comprises microcrystalline cellulose. In other embodiments, the composition comprises from about 15 mg to 40 mg (e.g., from about 15 mg to about 25 mg, from about 20 mg to about 25 mg, from about 25 mg to about 30 mg, from about 30 mg to about 40 mg), microcrystalline cellulose. In some embodiments, the composition comprises from about 15% to about 35% by weight (e.g., from about 15% to about 20%, from about 20% to about 25%, from 25% to about 30%, from 30% to about 35% by weight) microcrystalline cellulose.

In some embodiments, the composition comprises from about 15 mg to about 25 mg microcrystalline cellulose. In some embodiments, the composition comprises from about 30 mg to about 40 mg microcrystalline cellulose. In some embodiments, the composition further comprises a glidant. In some embodiments, the glidant comprises colloidal silicon dioxide. In some embodiments, the composition further comprises a lubricant. In some embodiments, the lubricant comprises magnesium stearate. In some embodiments, the composition further comprises a coating. In some embodiments, the compound of formula (I) or (II), including, for example, the compound of Form C or Form B, is stable within the formulation at about 25° C. at 60% relative humidity for at least 24 months. In some embodiments, the compound is stable at about 25° C. at 60% relative humidity for at least 36 months. In some embodiments, the compound is stable at about 25° C. at 60% relative humidity for at least 48 months. In other embodiments, the compound is stable at about 25° C. at 60% relative humidity for at least 60 months. In some embodiments, the compound is stable at about 40° C. at 75% relative humidity for at least 6 months.

In other embodiments of the oral dosage forms or compositions described herein, the compound of formula (I) or a pharmaceutically acceptable salt thereof (e.g., the compound of formula (II)) is a crystalline form. In certain embodiments, the crystalline form is a crystalline form as described herein, such as crystalline Form C or crystalline Form B.

Crystalline Form of the Compound of Formula (II)

A crystalline form of the compound of formula (II) used in the method as described herein may exhibit an X-ray powder diffraction (XRPD) pattern comprising at least one peak selected from peaks at the following diffraction angles (2θ): 26.6±0.2, 16.2±0.2, 17.4±0.2, 22.6±0.2, 11.5±0.2, 23.9±0.2, 18.3±0.2, 19.2±0.2, 18.5±0.2 or 20.0±0.2. In certain embodiments, a crystalline form of the compound of formula (II) disclosed herein may exhibit an XRPD pattern comprising peaks at the following diffraction angles (2θ): 16.2±0.2, 17.4±0.2, and 26.6±0.2.

Figure 2:
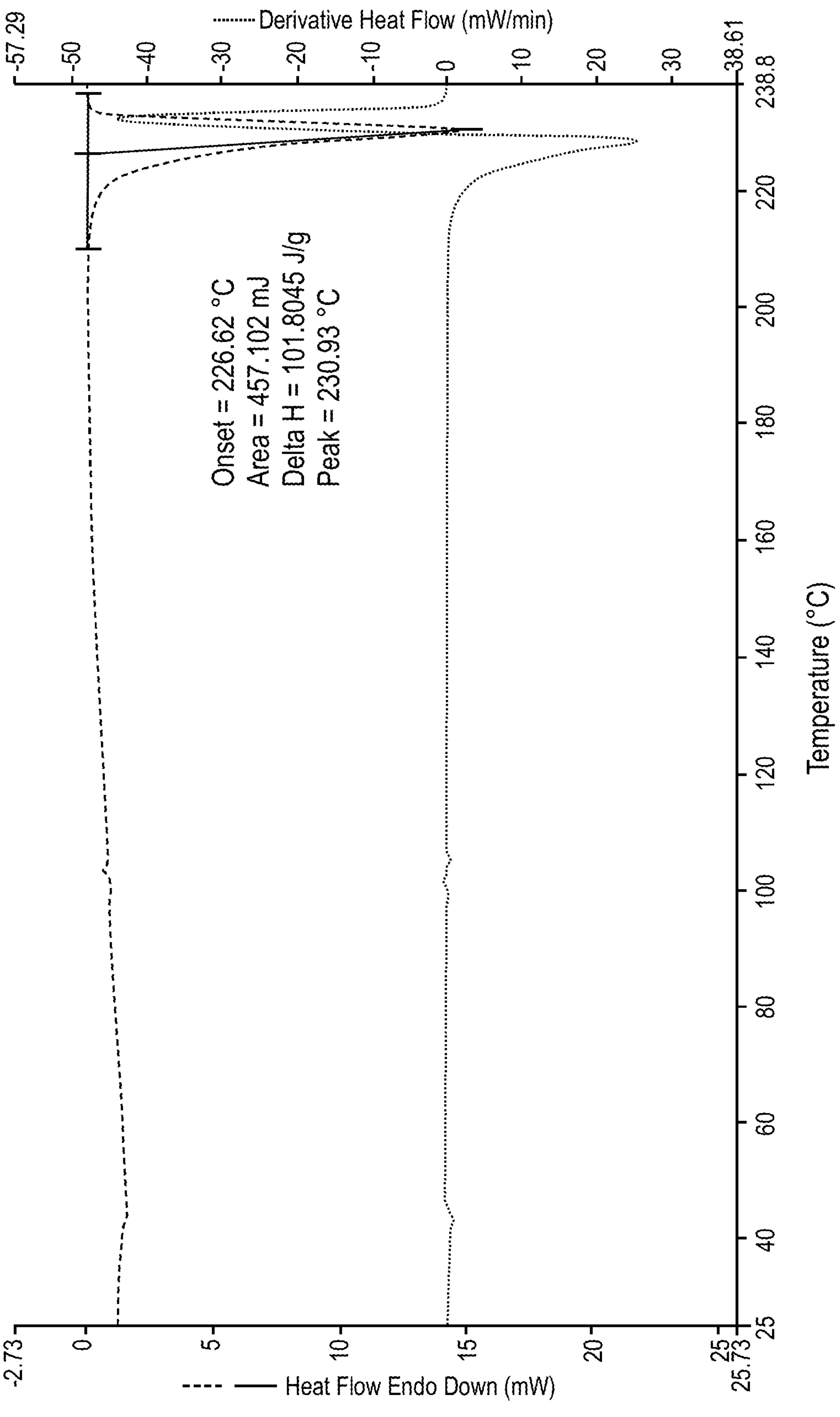
FIG. 2 is a differential scanning calorimetry (DSC) thermogram of Form C of the compound of formula (II).

In some embodiments, the crystalline form exhibits an XRPD pattern comprising peaks at the following diffraction angles (2θ): 11.5±0.2, 16.2±0.2, 17.4±0.2, 22.6±0.2, and 26.6±0.2. In other embodiments, the crystalline form exhibits an XRPD pattern comprising peaks at the following diffraction angles (2θ): 11.5±0.2, 16.2±0.2, 17.4±0.2, 18.3±0.2, 18.5±0.2, 19.2±0.2, 20.0±0.2, 22.6±0.2, 23.9±0.2, and 26.6±0.2. In certain embodiments, the crystalline form has a XRPD pattern substantially the same as depicted in FIG. 1. In some embodiments, the XRPD pattern was obtained using Cu Kα radiation. In certain embodiments, the crystalline form has a melting point onset as determined by differential scanning calorimetry at about 226.6° C. In some embodiments, the crystalline form has a differential scanning calorimetry curve substantially the same as shown in FIG. 2.

A crystalline form of the compound of formula (II) used in the method as described herein may exhibit an XRPD pattern comprising at least one peak selected from peaks at the following diffraction angles (2θ): 21.9±0.2, 18.5±0.2, 17.8±0.2, 10.2±0.2, 20.5±0.2, 25.2±0.2, 16.9±0.2, 24.2±0.2, 28.6±0.2 or 21.2±0.2. In certain embodiments, a crystalline form of the compound of formula (II) disclosed herein may exhibit an XRPD pattern comprising peaks at the following diffraction angles (2θ): 21.9±0.2, 18.5±0.2, and 17.8±0.2.

Figure 7:
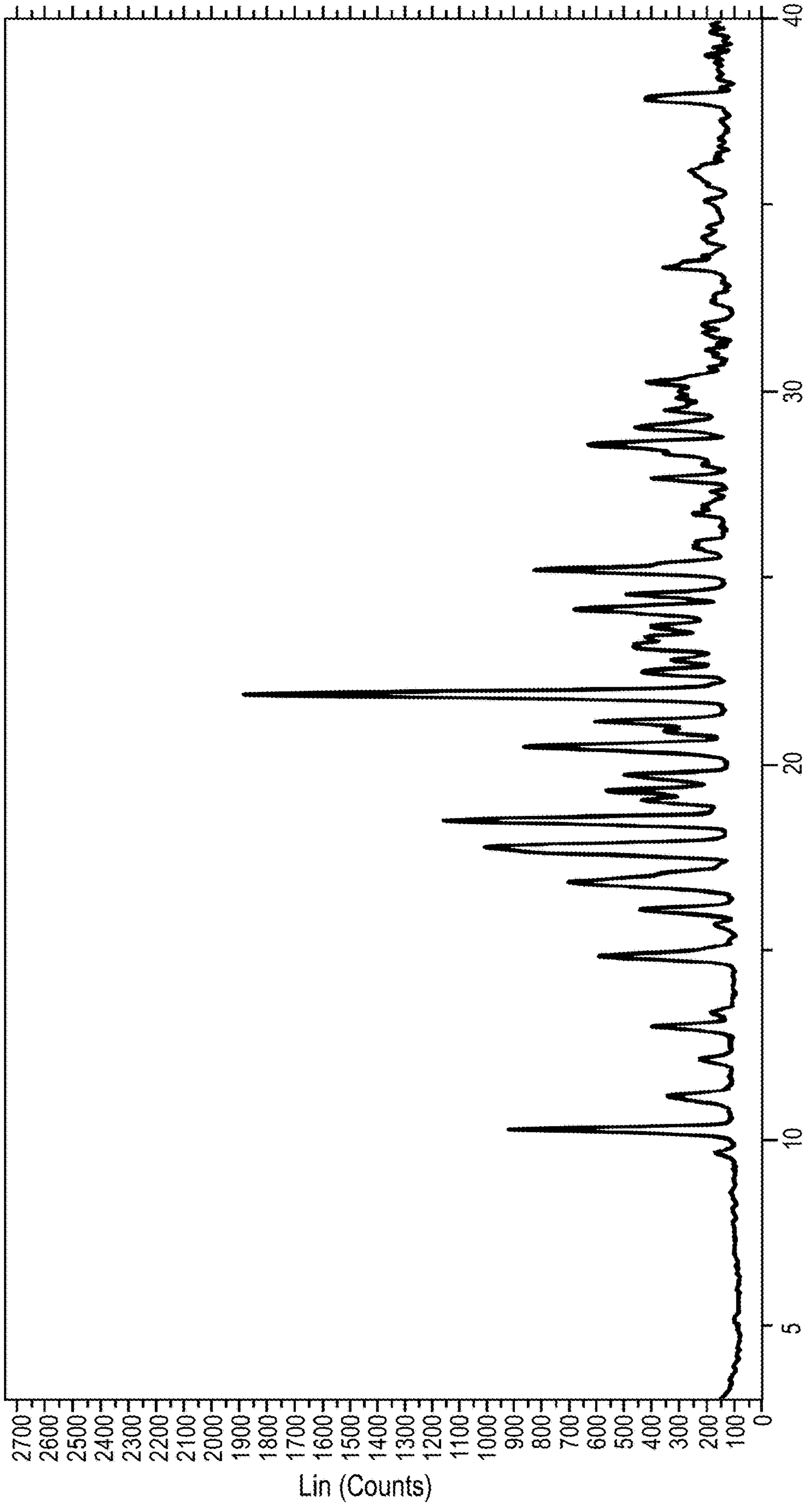
FIG. 7 is an XRPD of Form B of the compound of formula (II).

In some embodiments, the crystalline form exhibits an XRPD pattern comprising peaks at the following diffraction angles (2θ): 21.9±0.2, 18.5±0.2, 17.8±0.2, 10.2±0.2, and 20.5±0.2. In other embodiments, the crystalline form exhibits an XRPD pattern comprising peaks at the following diffraction angles (2θ): 21.9±0.2, 18.5±0.2, 17.8±0.2, 10.2±0.2, 20.5±0.2, 25.2±0.2, 16.9±0.2, 24.2±0.2, 28.6±0.2, and 21.2±0.2. In certain embodiments, the crystalline form has a XRPD pattern substantially the same as depicted in FIG. 7. In some embodiments, the powder XRPD was obtained using Cu Kα radiation. In certain embodiments, the crystalline form has a melting point onset as determined by differential scanning calorimetry at about 97.9° C., 131.6° C., 223.7° C., 83.8° C., 128.9° C., 168.9° C., or 224.4° C. In some embodiments, the crystalline form has a differential scanning calorimetry curve substantially the same as shown in FIG. 8.

Immediate-Release Formulations

In some embodiments, a dosage form or composition that can be used in a method described herein may be a dosage form or composition comprising the compound of formula (I) or a pharmaceutically acceptable salt thereof (e.g., the compound of formula (II)), where the compound of formula (I) or a pharmaceutically acceptable salt thereof (e.g., the compound of formula (II)) is released immediately upon an administration to the subject.

In other embodiments, a dosage form that can be used in a method described herein may be an oral capsule for immediate release comprising from about 15 mg to about 20 mg of the compound of formula (I) or a pharmaceutically acceptable salt thereof (e.g., the compound of formula (II)); and from about 75 mg to 85 mg diluent; from about 2 mg to 10 mg binder; from about 1% to about 5 disintegrant; and from about 0.1 mg to 5 mg lubricant.

Administrations

In some embodiments, the dosage form is administered to the subject more than once a day (e.g., twice a day, three times a day, or four times a day).

In some embodiments, the dosage form is administered to the subject once a day (e.g., one 20 mg tablet once a day, two 20 mg tablets once a day, or three 20 mg tablets once a day). In some embodiments, the dosage form is administered to the subject twice a day (e.g., one 10 mg tablet twice a day, one 20 mg tablet twice a day, two 20 mg tablets twice a day, three 20 mg tablets twice a day). In some embodiments, the dosage form is administered to the subject every other day. In certain embodiments, about 1 mg to 60 mg, such as 20 mg to 40 mg, of the compound of formula (I) or a pharmaceutically acceptable salt thereof (e.g., the compound of formula (II)) is administered to the subject daily. In other embodiments, about 15 mg to 25 mg of the compound of formula (I) or a pharmaceutically acceptable salt thereof (e.g., the compound of formula (II)) is administered to the subject daily. In certain embodiments, about 30 mg to 40 mg of the compound of formula (I) or a pharmaceutically acceptable salt thereof (e.g., the compound of formula (II)) is administered to the subject daily.

In some embodiments, the dosage form, upon administration to the subject, has a reduced $C_{max}$ value than a reference oral dosage form (e.g., a dosage form with any intended release rate profile e.g., modified release rate profile, a dosage form that does not have a modified release rate profile, a dosage form that does not have a modified-release polymer, e.g., an HPMC polymer). In some embodiments, the dosage form, upon administration to the subject, has a greater $t_{max}$ value than a reference oral dosage form (e.g., a dosage form with any intended release rate profile e.g., modified release rate profile, a dosage form that does not have a modified release rate profile, a dosage form that does not have a modified-release polymer, e.g., an HPMC polymer).

Epilepsy and Epilepsy Syndromes

The compositions described herein are useful in the treatment of epilepsy and epilepsy syndromes. Epilepsy is a central nervous system disorder in which nerve cell activity in the brain becomes disrupted, causing recurrent seizures which can manifest as abnormal movements, periods of unusual behavior, sensations and sometimes loss of consciousness. Seizure symptoms will vary widely, from a simple blank stare for a few seconds to repeated twitching of their arms or legs during a seizure.

Epilepsy may involve a generalized seizure, involving multiple areas of the brain, or a partial or focal seizure. All areas of the brain are involved in a generalized seizure. A person experiencing a generalized seizure may cry out or make some sound, stiffen for several seconds to a minute and then have rhythmic movements of the arms and legs. The eyes may be open, and/or the person may appear not to be breathing and turn blue. The return to consciousness may be gradual, and the person may be confused from minutes to hours. The following are the main types of generalized seizures: tonic-clonic, tonic, clonic, myoclonic, myoclonic-tonic-clonic, myoclonic-atonic, atonic, and absence (typical, atypical, myoclonic, eyelid myoclonia) seizures, and epileptic spasms. In a partial or focal seizure, only part of the brain is involved, so only part of the body is affected. Depending on the part of the brain having abnormal electrical activity, symptoms may vary.

Epilepsy, as described herein, includes a generalized, partial, complex partial (e.g., seizures involving only part of the brain, but where consciousness is compromised), tonic clonic, clonic, tonic, refractory seizures, status epilepticus, absence seizures, febrile seizures, or temporal lobe epilepsy.

The compositions described herein may also be useful in the treatment of epilepsy syndromes. Severe syndromes with diffuse brain dysfunction caused, at least partly, by some aspect of epilepsy, are also referred to as epileptic encephalopathies. These are associated with frequent seizures that are resistant to treatment and severe cognitive dysfunction, for instance West syndrome.

In some embodiments, the epilepsy syndrome comprises epileptic encephalopathy, Dravet syndrome, Angelman syndrome, CDKL5 disorder, frontal lobe epilepsy, infantile spasms, West's syndrome, Juvenile Myoclonic Epilepsy, Landau-Kleffner syndrome, Lennox-Gastaut syndrome, Ohtahara syndrome, PCDH19 epilepsy, or Glut1 deficiency. In some embodiments, the epilepsy syndrome is childhood absence epilepsy (CAE). In some embodiments, the epilepsy syndrome is juvenile absence epilepsy (JAE). In some embodiments, the epilepsy syndrome is Lennox-Gastaut syndrome. In some embodiments, the epilepsy syndrome is SLC6A1 epileptic encephalopathy. In some embodiments, the epilepsy syndrome is associated with mutations in the genes that code for T-type calcium channels (e.g., CACNA1G, EEF1A2, and GABRG2 for genetic generalized epilepsy (GGE) and LGI1, TRIM3, and GABRG2 for non-acquired focal epilepsy (NAFE)), as discussed, for example, in Feng, Y C A, et al., "Ultra-Rare Genetic Variation in the Epilepsies: A Whole-Exome Sequencing Study of 17,606 Individuals," *Am. J. Human Gen.* 2019; 105(2):267-282. In some embodiments, the epilepsy syndrome is Doose syndrome or myoclonic astatic epilepsy. In some embodiments, the epilepsy syndrome is epileptic encephalopathy with continuous spike and wave during sleep (CSWS). In some embodiments, the epilepsy syndrome is Landau Kleffner Syndrome (LKS). In some embodiments, the epilepsy syndrome is Jeavons syndrome.

Absence Seizures

Absence seizures are one of the most common seizure types in patients with idiopathic generalised epilepsy (IGE) (Berg et al., Epilepsia 2000). Absence seizures are relatively brief, non-convulsive seizures characterised by abrupt onset of loss of awareness and responsiveness, usually lasting between 10-30 seconds in duration, with a rapid return to normal consciousness without post-ictal confusion. The seizures are characterised on an accompanying EEG recording by the abrupt onset and offset of generalised 1-6 Hz (e.g., 3 Hz) spike and wave discharges. Absence seizure often occur multiple times per day, interrupt learning and psychosocial functioning, and present a risk of injury because of the frequent episodes of loss of awareness. Typically, absence seizures begin in early childhood and remit by teenage years. However, in a minority of patients they persist into adulthood where they are often drug resistant, and may be accompanied by other seizure types such as generalised tonic-clonic seizures. In these adult patients, the absence seizures are usually highly disabling, in particular by disqualifying the sufferer from obtaining a motor vehicle licence or pursuing occupations and hobbies in which the seizures-associated periods of loss of awareness pose a safety risk, and are associated with significant psychosocial disabilities (Wirrell et al., 1997).

While there is a common perception that absence seizures are relatively "easy" to treat, a randomised control trial in patients with childhood absence epilepsy showed that even the most effective anti-epileptic drugs, ethosuximide and valproate, only completely controlled the seizures in 53% and 58% of patients respectively at 16 weeks as assessed by video-EEG recordings (Glauser et al., 2010), and 45% and 44% respectively at 12 months (Glauser et al., 2013). Lamotrigine, the other AED commonly used to treat absence seizures, only controlled the seizures in 29% of patients at 16 weeks, and 21% of patients at 12 months. Furthermore, both ethosuximide and valproate are commonly associated with intolerable side effects (occurring in 24% of patients treated with either of these drugs) (Glauser et al., 2010), and the latter is now generally considered to be contraindicated in girls and women of childbearing potential. Other treatment options for absence seizures are limited, with only benzodiazepines having established efficacy, and these are commonly poorly tolerated due to sedative and cognitive side effects. Absence seizures persisting into adult life are particularly difficult to treat, with patients often being treated with multiple drugs resulting in significant side-effects without attaining seizure control.

There is abundant evidence that low threshold (T-type) calcium channels play a role in the generation and maintenance of absence seizures, being a key component of the oscillatory burst firing that occurs in thalamocortical neurones during absence seizures (Pinault and O'Brien, 1997). In some embodiments, the present disclosure is directed towards a method for treating absence seizures with a composition described herein. In some embodiments, the absence seizures are refractory absence seizures. In some embodiments, the absence seizures are refractory to an anti-epileptic drug (e.g., ethosuximide, valproic acid, or lamotrigine).

In some embodiments, the subject has epilepsy. In some embodiments, the absence seizures are atypical absence seizures. In some embodiments, the absence seizures comprise adult absence seizures, juvenile absence seizures, or childhood absence seizures.

In some embodiments, the methods described herein further comprise identifying a subject having absence seizures.

Genetic Epilepsies

In some embodiments, the epilepsy or epilepsy syndrome is a genetic epilepsy or a genetic epilepsy syndrome. In some embodiments, the epilepsy or epilepsy syndrome is genetic generalized epilepsy. In some embodiments, epilepsy or an epilepsy syndrome comprises epileptic encephalopathy, epileptic encephalopathy with SCN1A, SCN2A, SCN8A mutations, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, and KCNT1 epileptic encephalopathy.

In some embodiments, the methods described herein further comprise identifying a subject having epilepsy or an epilepsy syndrome (e.g., epileptic encephalopathy, epileptic encephalopathy with SCN1A, SCN2A, SCN8A mutations, early infantile epileptic encephalopathy, Dravet syndrome, Dravet syndrome with SCN1A mutation, generalized Epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, and KCNT1 epileptic encephalopathy) prior to administration of a composition described herein.

In one aspect, the present invention features a method of treating epilepsy or an epilepsy syndrome (e.g., epileptic encephalopathy, epileptic encephalopathy with SCN1A, SCN2A, SCN8A mutations, early infantile epileptic encephalopathy, Dravet syndrome, Dravet syndrome with SCN1A mutation, generalized Epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, and KCNT1 epileptic encephalopathy) comprising administering to a subject in need thereof a composition described herein.

A composition of the present invention may also be used to treat an epileptic encephalopathy, wherein the subject has a mutation in one or more of ALDH7A1, ALG13, ARHGEF9, ARX, ASAH1, CDKL5, CHD2, CHRNA2, CHRNA4, CHRNB2, CLN8, CNTNAP2, CPA6, CSTB, DEPDC5, DNM1, EEF1A2, EPM2A, EPM2B, GABRA1, GABRB3, GABRG2, GNAO1, GOSR2, GRIN1, GRIN2A, GRIN2B, HCN1, IER3IP1, KCNA2, KCNB1, KCNC1, KCNMA1, KCNQ2, KCNQ3, KCNT1, KCTD7, LGI1, MEF2C, NHLRC1, PCDH19, PLCB1, PNKP, PNPO, PRICKLE1, PRICKLE2, PRRT2, RELN, SCARB2, SCN1A, SCN1B, SCN2A, SCN8A, SCN9A, SIAT9, SIK1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, and WWOX.

In some embodiments, the methods described herein further comprise identifying a subject having a mutation in one or more of ALDH7A1, ALG13, ARHGEF9, ARX, ASAH1, CDKL5, CHD2, CHRNA2, CHRNA4, CHRNB2, CLN8, CNTNAP2, CPA6, CSTB, DEPDC5, DNM1, EEF1A2, EPM2A, EPM2B, GABRA1, GABRB3, GABRG2, GNAO1, GOSR2, GRIN1, GRIN2A, GRIN2B, HCN1, IER3IP1, KCNA2, KCNB1, KCNC1, KCNMA1, KCNQ2, KCNQ3, KCNT1, KCTD7, LGI1, MEF2C, NHLRC1, PCDH19, PLCB1, PNKP, PNPO, PRICKLE1, PRICKLE2, PRRT2, RELN, SCARB2, SCN1A, SCN1B, SCN2A, SCN8A, SCN9A, SIAT9, SIK1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, WWOX, CACNA1G, CACNA1H, and CACNA1I prior to administration of a composition described herein.

A composition of the present invention may also be used to treat an epileptic encephalopathy, wherein the subject has a mutation in one or more of ADSL, ALDH5A1, ALDH7A1, ALG13, ARG1, ARHGEF9, ARX, ATP1A2, ATP1A3, ATRX, BRAT1, C12orf57, CACNA1A, CACNA2D2, CARS2, CASK, CDKL5, CHD2, CHRNA2, CHRNA4, CHRNB2, CLCN4, CLN2 (TPP1), CLN3, CLN5, CLN6, CLN8, CNTNAP2, CSTB, CTSD, DDC, DEPDC5, DNAJC5, DNM1, DOCK7, DYRK1A, EEF1A2, EFHC1, EHMT1, EPM2A, FARS2, FOLR1, FOXG1, FRRS1L, GABBR2, GABRA1, GABRB2, GABRB3, GABRG2, GAMT, GATM, GLRA1, GNAO1, GOSR2, GRIN1, GRIN2A, GRIN2B, HCN1, HNRNPU, IER3IP1, IQSEC2, ITPA, JMJD1C, KANSL1, KCNA2, KCNB1, KCNC1, KCNH2, KCNJ10, KCNMA1, KCNQ2, KCNQ3, KCNT1, KCTD7, LGI1, LIAS, MBD5, MECP2, MEF2C, MFSD8, MOCS1, MOCS2, MTOR, NEDD4L, NEXMIF, NGLY1, NHLRC1, NPRL3, NRXN1, PACS1, PCDH19, PIGA, PIGN, PIGO, PLCB1, PNKD, PNKP, PNPO, POLG, PPT1, PRICKLE1, PRIMA1, PRRT2, PURA, QARS, RELN, ROGDI, SATB2, SCARB2, SCN1A, SCN1B, SCN2A, SCN3A, SCN8A, SCN9A, SERPINI1, SGCE, SIK1, SLC12A5, SLC13A5, SLC19A3, SLC25A12, SLC25A22, SLC2A1, SLC35A2, SLC6A1, SLC6A8, SLC9A6, SMC1A, SNX27, SPATA5, SPTAN1, ST3GAL5, STRADA, STX1B, STXBP1, SUOX, SYN1, SYNGAP1, SYNJ1, SZT2, TBC1D24, TCF4, TPK1, TSC1, TSC2, UBE3A, WDR45, WWOX, ZDHHC9, ZEB2, ABAT, ARHGEF15, ATP6AP2, CACNA1H, CACNB4, CASR, CERS1, CNTN2, CPA6, DIAPH1, FASN, GABRD, GAL, GPHN, KCNA1, KCND2, KCNH5, KPNA7, LMNB2, NECAP1, PIGG, PIGQ, PIK3AP1, PRDM8, PRICKLE2, RBFOX1, RBFOX3, RYR3, SCN5A, SETD2, SLC35A3, SNAP25, SRPX2, ST3GAL3, TBL1XR1, AMT, GCSH, GLDC, FLNA, PTEN, and RANBP2.

In some embodiments, the methods described herein further comprise identifying a subject having a mutation in one or more of ADSL, ALDH5A1, ALDH7A1, ALG13, ARG1, ARHGEF9, ARX, ATP1A2, ATP1A3, ATRX, BRAT1, C12orf57, CACNA1A, CACNA2D2, CARS2, CASK, CDKL5, CHD2, CHRNA2, CHRNA4, CHRNB2, CLCN4, CLN2 (TPP1), CLN3, CLN5, CLN6, CLN8, CNTNAP2, CSTB, CTSD, DDC, DEPDC5, DNAJC5, DNM1, DOCK7, DYRK1A, EEF1A2, EFHC1, EHMT1, EPM2A, FARS2, FOLR1, FOXG1, FRRS1L, GABBR2, GABRA1, GABRB2, GABRB3, GABRG2, GAMT, GATM, GLRA1, GNAO1, GOSR2, GRIN1, GRIN2A, GRIN2B, HCN1, HNRNPU, IER3IP1, IQSEC2, ITPA, JMJD1C, KANSL1, KCNA2, KCNB1, KCNC1, KCNH2, KCNJ10, KCNMA1, KCNQ2, KCNQ3, KCNT1, KCTD7, LGI1, LIAS, MBD5, MECP2, MEF2C, MFSD8, MOCS1, MOCS2, MTOR, NEDD4L, NEXMIF, NGLY1, NHLRC1, NPRL3, NRXN1, PACS1, PCDH19, PIGA, PIGN, PIGO, PLCB1, PNKD, PNKP, PNPO, POLG, PPT1, PRICKLE1, PRIMA1, PRRT2, PURA, QARS, RELN, ROGDI, SATB2, SCARB2, SCN1A, SCN1B, SCN2A, SCN3A, SCN8A, SCN9A, SERPINI1, SGCE, SIK1, SLC12A5, SLC13A5, SLC19A3, SLC25A12, SLC25A22, SLC2A1, SLC35A2, SLC6A1, SLC6A8, SLC9A6, SMC1A, SNX27, SPATA5, SPTAN1, ST3GAL5, STRADA, STX1B, STXBP1, SUOX, SYN1, SYNGAP1, SYNJ1, SZT2, TBC1D24, TCF4, TPK1, TSC1, TSC2, UBE3A, WDR45, WWOX, ZDHHC9, ZEB2, ABAT, ARHGEF15, ATP6AP2, CACNA1H, CACNB4, CASR, CERS1, CNTN2, CPA6, DIAPH1, FASN, GABRD, GAL, GPHN, KCNA1, KCND2, KCNH5, KPNA7, LMNB2, NECAP1, PIGG, PIGQ, PIK3AP1, PRDM8, PRICKLE2, RBFOX1, RBFOX3, RYR3, SCN5A, SETD2, SLC35A3, SNAP25, SRPX2, ST3GAL3, TBL1XR1, AMT, GCSH, GLDC, FLNA, PTEN, and RANBP2.

A composition of the present invention may also be used to treat an epileptic encephalopathy, wherein the subject has a mutation in one or more of ADSL, ALDH5A1, ALDH7A1, ALG13, ARHGEF9, ARX, ASNS, ATP1A2, ATP1A3, ATP6AP2, ATRX, BRAT1, CACNA1A, CASK, CDKL5, CHD2, CHRNA2, CHRNA4, CHRNA7, CHRNB2, CLCN4, CLN3, CLN5, CLN6, CLN8, CNTNAP2, CSTB, CTNNB1, CTSD (CLN10), CTSF, DDX3X, DEPDC5, DNAJC5 (CLN4B), DNM1, DYRK1A, EEF1A2, EHMT1, EPM2A, FLNA, FOLR1, FOXG1, FRRS1L, GABBR2, GABRA1, GABRB2, GABRB3, GABRG2, GAMT, GATM, GLDC, GNAO1, GOSR2, GRIN1, GRIN2A, GRIN2B, HNRNPU, IQSEC2, KANSL1, KCNA2, KCNB1, KCNC1, KCNH1, KCNJ10, KCNMA1, KCNQ2, KCNQ3, KCNT1, KCTD7 (CLN14), KDM6A, KIAA2022, LGI1, MAGI2, MBD5, MECP2, MEF2C, MFSD8 (CLN7), NALCN, NGLY1, NHLRC1 (EPM2B), NPRL3. NR2F1, NRXN1, PACS1, PCDH19, PIGA PIGO, PIGV, PLCB1, PNKP, PNPO, POLG, PPP2R5D, PPT1 (CLN1), PRRT2, PURA, QARS, SATB2, SCARB2, SCN1A, SCN1B, SCN2A, SCN8A, SLC13A5, SLC19A3, SLC25A22, SLC2A1, SLC6A1, SLC6A8, SLC9A6, SMC1A, SPATA5, SPTAN1, STX1B, STXBP1, SYNGAP1, SZT2, TBC1D24, TBL1XR1, TCF4, TPP1 (CLN2), TSC1, TSC2, UBE3A, WDR45, WWOX, and ZEB2.

In some embodiments, the methods described herein further comprise identifying a subject having a mutation in one or more of ADSL, ALDH5A1, ALDH7A1, ALG13, ARHGEF9, ARX, ASNS, ATP1A2, ATP1A3, ATP6AP2, ATRX, BRAT1, CACNA1A, CASK, CDKL5, CHD2, CHRNA2, CHRNA4, CHRNA7, CHRNB2, CLCN4, CLN3, CLN5, CLN6, CLN8, CNTNAP2, CSTB, CTNNB1, CTSD (CLN10), CTSF, DDX3X, DEPDC5, DNAJC5 (CLN4B), DNM1, DYRK1A, EEF1A2, EHMT1, EPM2A, FLNA, FOLR1, FOXG1, FRRS1L, GABBR2, GABRA1, GABRB2, GABRB3, GABRG2, GAMT, GATM, GLDC, GNAO1, GOSR2, GRIN1, GRIN2A, GRIN2B, HNRNPU, IQSEC2, KANSL1, KCNA2, KCNB1, KCNC1, KCNH1, KCNJ10, KCNMA1, KCNQ2, KCNQ3, KCNT1, KCTD7 (CLN14), KDM6A, KIAA2022, LGI1, MAGI2, MBD5, MECP2, MEF2C, MFSD8 (CLN7), NALCN, NGLY1, NHLRC1 (EPM2B), NPRL3. NR2F1, NRXN1, PACS1, PCDH19, PIGA PIGO, PIGV, PLCB1, PNKP, PNPO, POLG, PPP2R5D, PPT1 (CLN1), PRRT2, PURA, QARS, SATB2, SCARB2, SCN1A, SCN1B, SCN2A, SCN8A, SLC13A5, SLC19A3, SLC25A22, SLC2A1, SLC6A1, SLC6A8, SLC9A6, SMC1A, SPATA5, SPTAN1, STX1B, STXBP1, SYNGAP1, SZT2, TBC1D24, TBL1XR1, TCF4, TPP1 (CLN2), TSC1, TSC2, UBE3A, WDR45, WWOX, and ZEB2.

A composition of the present invention may also be used to treat an epileptic encephalopathy, wherein the subject has a mutation in one or more of ALDH7A1, ARHGEF9, ARX, ATP13A2, ATP1A2, CACNA1A, CASK, CDKL5, CHD2, CHRNA2, CHRNA4, CHRNB2, CLN3, CLN5, CLN6, CLN8, CNTNAP2, CRH, CSTB, CTSD, CTSF, DCX, DEPDC5, DNAJC5, DNM1, DYNC1H1, DYRK1A, EEF1A2, EPM2A, FLNA, FOLR1, FOXG1, GABRA1, GABRB3, GABRG2, GAMT, GATM, GNAO1, GOSR2, GRIN1, GRIN2A, GRIN2B, GRN, HCN1, HNRNPU, IQSEC2, KCNA2, KCNC1, KCNJ10, KCNQ2, KCNQ3, KCNT1, KCTD7, KIAA2022, LGI1, MECP2, MEF2C, MFSD8, NHLRC1, NRXN1, PCDH19, PIGA, PLCB1, PNKP, PNPO, POLG, PPT1, PRICKLE1, PRRT2, PURA, SCARB2, SCN1A, SCN1B, SCN2A, SCN8A, SIK1, SLC13A5, SLC25A22, SLC2A1, SLC35A2, SLC6A1, SLC9A6, SMC1A, SNAP25, SPTAN1, ST3GAL3, STX1B, STXBP1, SYN1, SYNGAP1, SZT2, TBC1D24, TBL1XR1, TCF4, TPP1, TSC1, TSC2, UBE3A, WDR45, and ZEB2.

In some embodiments, the methods described herein further comprise identifying a subject having a mutation in one or more of ALDH7A1, ARHGEF9, ARX, ATP13A2, ATP1A2, CACNA1A, CASK, CDKL5, CHD2, CHRNA2, CHRNA4, CHRNB2, CLN3, CLN5, CLN6, CLN8, CNTNAP2, CRH, CSTB, CTSD, CTSF, DCX, DEPDC5, DNAJC5, DNM1, DYNC1H1, DYRK1A, EEF1A2, EPM2A, FLNA, FOLR1, FOXG1, GABRA1, GABRB3, GABRG2, GAMT, GATM, GNAO1, GOSR2, GRIN1, GRIN2A, GRIN2B, GRN, HCN1, HNRNPU, IQSEC2, KCNA2, KCNC1, KCNJ10, KCNQ2, KCNQ3, KCNT1, KCTD7, KIAA2022, LGI1, MECP2, MEF2C, MFSD8, NHLRC1, NRXN1, PCDH19, PIGA, PLCB1, PNKP, PNPO, POLG, PPT1, PRICKLE1, PRRT2, PURA, SCARB2, SCN1A, SCN1B, SCN2A, SCN8A, SIK1, SLC13A5, SLC25A22, SLC2A1, SLC35A2, SLC6A1, SLC9A6, SMC1A, SNAP25, SPTAN1, ST3GAL3, STX1B, STXBP1, SYN1, SYNGAP1, SZT2, TBC1D24, TBL1XR1, TCF4, TPP1, TSC1, TSC2, UBE3A, WDR45, and ZEB2.

Mood Disorders

Also provided herein are methods for treating a psychiatric disorder such as a mood disorder, for example clinical depression, postnatal depression or postpartum depression, perinatal depression, atypical depression, melancholic depression, psychotic major depression, catatonic depression, seasonal affective disorder, dysthymia, double depression, depressive personality disorder, recurrent brief depression, minor depressive disorder, bipolar disorder or manic depressive disorder, depression caused by chronic medical conditions, treatment-resistant depression, refractory depression, suicidality, suicidal ideation, or suicidal behavior. In some embodiments, the method described herein provides therapeutic effect to a subject suffering from depression (e.g., moderate or severe depression). In some embodiments, the mood disorder is associated with a disease or disorder described herein (e.g., neuroendocrine diseases and disorders, neurodegenerative diseases and disorders (e.g., epilepsy), movement disorders, tremor (e.g., Parkinson's Disease), women's health disorders or conditions).

Clinical depression is also known as major depression, major depressive disorder (MDD), severe depression, unipolar depression, unipolar disorder, and recurrent depression, and refers to a mental disorder characterized by pervasive and persistent low mood that is accompanied by low self-esteem and loss of interest or pleasure in normally enjoyable activities. Some people with clinical depression have trouble sleeping, lose weight, and generally feel agitated and irritable. Clinical depression affects how an individual feels, thinks, and behaves and may lead to a variety of emotional and physical problems. Individuals with clinical depression may have trouble doing day-to-day activities and make an individual feel as if life is not worth living.

Peripartum depression refers to depression in pregnancy. Symptoms include irritability, crying, feeling restless, trouble sleeping, extreme exhaustion (emotional and/or physical), changes in appetite, difficulty focusing, increased anxiety and/or worry, disconnected feeling from baby and/or fetus, and losing interest in formerly pleasurable activities.

Postnatal depression (PND) is also referred to as postpartum depression (PPD) and refers to a type of clinical depression that affects women after childbirth. Symptoms can include sadness, fatigue, changes in sleeping and eating habits, reduced sexual desire, crying episodes, anxiety, and irritability. In some embodiments, the PND is a treatment-resistant depression (e.g., a treatment-resistant depression as described herein). In some embodiments, the PND is refractory depression (e.g., a refractory depression as described herein).

In some embodiments, a subject having PND also experienced depression, or a symptom of depression during pregnancy. This depression is referred to herein as perinatal depression. In an embodiment, a subject experiencing perinatal depression is at increased risk of experiencing PND.

Atypical depression (AD) is characterized by mood reactivity (e.g., paradoxical anhedonia) and positivity, significant weight gain or increased appetite. Patients suffering from AD also may have excessive sleep or somnolence (hypersomnia), a sensation of limb heaviness, and significant social impairment as a consequence of hypersensitivity to perceived interpersonal rejection.

Melancholic depression is characterized by loss of pleasure (anhedonia) in most or all activities, failures to react to pleasurable stimuli, depressed mood more pronounced than that of grief or loss, excessive weight loss, or excessive guilt.

Psychotic major depression (PMD) or psychotic depression refers to a major depressive episode, in particular of melancholic nature, where the individual experiences psychotic symptoms such as delusions and hallucinations.

Catatonic depression refers to major depression involving disturbances of motor behavior and other symptoms. An individual may become mute and stuporose, and either is immobile or exhibits purposeless or bizarre movements.

Seasonal affective disorder (SAD) refers to a type of seasonal depression wherein an individual has seasonal patterns of depressive episodes coming on in the fall or winter.

Dysthymia refers to a condition related to unipolar depression, where the same physical and cognitive problems are evident. They are not as severe and tend to last longer (e.g., at least 2 years).

Double depression refers to fairly depressed mood (dysthymia) that lasts for at least 2 years and is punctuated by periods of major depression.

Depressive Personality Disorder (DPD) refers to a personality disorder with depressive features.

Recurrent Brief Depression (RBD) refers to a condition in which individuals have depressive episodes about once per month, each episode lasting 2 weeks or less and typically less than 2-3 days.

Minor depressive disorder or minor depression refers to a depression in which at least 2 symptoms are present for 2 weeks.

Bipolar disorder or manic depressive disorder causes extreme mood swings that include emotional highs (mania or hypomania) and lows (depression). During periods of mania the individual may feel or act abnormally happy, energetic, or irritable. They often make poorly thought out decisions with little regard to the consequences. The need for sleep is usually reduced. During periods of depression there may be crying, poor eye contact with others, and a negative outlook on life. The risk of suicide among those with the disorder is high at greater than 6% over 20 years, while self-harm occurs in 30-40%. Other mental health issues such as anxiety disorder and substance use disorder are commonly associated with bipolar disorder.

Depression caused by chronic medical conditions refers to depression caused by chronic medical conditions such as cancer or chronic pain, chemotherapy, chronic stress.

Treatment-resistant depression refers to a condition where the individuals have been treated for depression, but the symptoms do not improve. For example, antidepressants or psychological counseling (psychotherapy) do not ease depression symptoms for individuals with treatment-resistant depression. In some cases, individuals with treatment-resistant depression improve symptoms, but come back. Refractory depression occurs in patients suffering from depression who are resistant to standard pharmacological treatments, including tricyclic antidepressants, MAOIs, SSRIs, and double and triple uptake inhibitors and/or anxiolytic drugs, as well as non-pharmacological treatments (e.g., psychotherapy, electroconvulsive therapy, vagus nerve stimulation and/or transcranial magnetic stimulation).

Post-surgical depression refers to feelings of depression that follow a surgical procedure (e.g., as a result of having to confront one's mortality). For example, individuals may feel sadness or empty mood persistently, a loss of pleasure or interest in hobbies and activities normally enjoyed, or a persistent feeling of worthlessness or hopelessness.

Mood disorder associated with conditions or disorders of women's health refers to mood disorders (e.g., depression) associated with (e.g., resulting from) a condition or disorder of women's health (e.g., as described herein).

Suicidality, suicidal ideation, and suicidal behavior refer to the tendency of an individual to commit suicide. Suicidal ideation concerns thoughts about or an unusual preoccupation with suicide. The range of suicidal ideation varies greatly, from e.g., fleeting thoughts to extensive thoughts, detailed planning, role playing, and/or incomplete attempts. Symptoms include talking about suicide, getting the means to commit suicide, withdrawing from social contact, being preoccupied with death, feeling trapped or hopeless about a situation, increasing use of alcohol or drugs, doing risky or self-destructive things, and saying goodbye to people as if they won't be seen again.

Symptoms of depression include persistent anxious or sad feelings, feelings of helplessness, hopelessness, pessimism, worthlessness, low energy, restlessness, difficulty sleeping, sleeplessness, irritability, fatigue, motor challenges, loss of interest in pleasurable activities or hobbies, loss of concentration, loss of energy, poor self-esteem, absence of positive thoughts or plans, excessive sleeping, overeating, appetite loss, insomnia, self-harm, thoughts of suicide, and suicide attempts. The presence, severity, frequency, and duration of symptoms may vary on a case to case basis. Symptoms of depression, and relief of the same, may be ascertained by a physician or psychologist (e.g., by a mental state examination).

In some embodiments, the mood disorder is selected from depression, major depressive disorder, bipolar disorder, dysthymic disorder, anxiety disorders, stress, post-traumatic stress disorder, bipolar disorder, and compulsive disorders. In some embodiments, the mood disorder is major depressive disorder.

In some embodiments, the method comprises monitoring a subject with a known depression scale, e.g., the Hamilton Depression (HAM-D) scale, the Clinical Global Impression-Improvement Scale (CGI), and the Montgomery-Asberg Depression Rating Scale (MADRS). In some embodiments, a therapeutic effect can be determined by reduction in Hamilton Depression (HAM-D) total score exhibited by the subject. The therapeutic effect can be assessed across a specified treatment period. For example, the therapeutic effect can be determined by a decrease from baseline in HAM-D total score after administering a composition described herein (e.g., 12, 24, or 48 hours after administration; or 24, 48, 72, or 96 hours or more; or 1 day, 2 days, 14 days, 21 days, or 28 days; or 1 week, 2 weeks, 3 weeks, or 4 weeks; or 1 month, 2 months, 6 months, or 10 months; or 1 year, 2 years, or for life).

In some embodiments, the subject has a mild depressive disorder, e.g., mild major depressive disorder. In some embodiments, the subject has a moderate depressive disorder, e.g., moderate major depressive disorder. In some embodiments, the subject has a severe depressive disorder, e.g., severe major depressive disorder. In some embodiments, the subject has a very severe depressive disorder, e.g., very severe major depressive disorder. In some embodiments, the baseline HAM-D total score of the subject (i.e., prior to treatment with a composition described herein), is at least 24. In some embodiments, the baseline HAM-D total score of the subject is at least 18. In some embodiments, the baseline HAM-D total score of the subject is between and including 14 and 18. In some embodiments, the baseline HAM-D total score of the subject is between and including 19 and 22. In some embodiments, the HAM-D total score of the subject before treatment with a composition described herein is greater than or equal to 23. In some embodiments, the baseline score is at least 10, 15, or 20. In some embodiments, the HAM-D total score of the subject after treatment with a composition described herein is about 0 to 10 (e.g., less than 10; 0 to 10, 0 to 6, 0 to 4, 0 to 3, 0 to 2, or 1.8). In some embodiments, the HAM-D total score after treatment with a composition described herein is less than 10, 7, 5, or 3. In some embodiments, the decrease in HAM-D total score is from a baseline score of about 20 to 30 (e.g., 22 to 28, 23 to 27, 24 to 27, 25 to 27, 26 to 27) to a HAM-D total score at about 0 to 10 (e.g., less than 10; 0 to 10, 0 to 6, 0 to 4, 0 to 3, 0 to 2, or 1.8) after treatment with a composition described herein. In some embodiments, the decrease in the baseline HAM-D total score to HAM-D total score after treatment with a composition described herein is at least 1, 2, 3, 4, 5, 7, 10, 25, 40, or 50). In some embodiments, the percentage decrease in the baseline HAM-D total score to HAM-D total score after treatment with a composition described herein is at least 50% (e.g., 60%, 70%, 80%, or 90%). In some embodiments, the therapeutic effect is measured as a decrease in the HAM-D total score after treatment with a composition described herein relative to the baseline HAM-D total score.

In some embodiments, the method of treating a depressive disorder, e.g., major depressive disorder, provides a therapeutic effect (e.g., as measured by reduction in the HAM-D score within 14, 10, 4, 3, 2, or 1 days, or 24, 20, 16, 12, 10, or 8 hours or less. In some embodiments, the method of treating the depressive disorder, e.g., major depressive disorder, provides a therapeutic effect (e.g., as determined by a statistically significant reduction in HAM-D total score) within the first or second day of the treatment with a composition described herein. In some embodiments, the method of treating the depressive disorder, e.g., major depressive disorder, provides a therapeutic effect (e.g., as determined by a statistically significant reduction in HAM-D total score) within less than or equal to 14 days since the beginning of the treatment with a composition described herein. In some embodiments, the method of treating the depressive disorder, e.g., major depressive disorder, provides a therapeutic effect (e.g., as determined by a statistically significant reduction in HAM-D total score) within less than or equal to 21 days since the beginning of the treatment with a composition described herein. In some embodiments, the method of treating the depressive disorder, e.g., major depressive disorder, provides a therapeutic effect (e.g., as determined by a statistically significant reduction in HAM-D total score) within less than or equal to 28 days since the beginning of the treatment with a composition described herein. In some embodiments, the therapeutic effect is a decrease from baseline in HAM-D total score after treatment with a composition described herein. In some embodiments, the HAM-D total score of the subject before treatment with a composition described herein is at least 24. In some embodiments, the HAM-D total score of the subject before treatment with a composition described herein is at least 18. In some embodiments, the HAM-D total score of the subject before treatment with a composition described herein is between and including 14 and 18. In some embodiments, the decrease in HAM-D total score after treating the subject with a composition described herein relative to the baseline HAM-D total score is at least 10. In some embodiments, the decrease in HAM-D total score after treating the subject with a composition described herein relative to the baseline HAM-D total score is at least 15. In some embodiments, the HAM-D total score associated with treating the subject with a composition described herein is no more than a number ranging from 6 to 8. In some embodiments, the HAM-D total score associated with treating the subject with a composition described herein is no more than 7.

In some embodiments, the method provides therapeutic effect (e.g., as measured by reduction in Clinical Global Impression-Improvement Scale (CGI)) within 14, 10, 4, 3, 2, or 1 days, or 24, 20, 16, 12, 10, or 8 hours or less. In some embodiments, the CNS-disorder is a depressive disorder, e.g., major depressive disorder. In some embodiments, the method of treating the depressive disorder, e.g., major depressive disorder provides a therapeutic effect within the second day of the treatment period. In some embodiments, the therapeutic effect is a decrease from baseline in CGI score at the end of a treatment period (e.g., 14 days after administration).

A therapeutic effect for major depressive disorder can be determined by a reduction in Montgomery-Asberg Depression Rating Scale (MADRS) score exhibited by the subject. For example, the MADRS score can be reduced within 4, 3, 2, or 1 days; or 96, 84, 72, 60, 48, 24, 20, 16, 12, 10, 8 hours or less. The MADRS is a ten-item diagnostic questionnaire (regarding apparent sadness, reported sadness, inner tension, reduced sleep, reduced appetite, concentration difficulties, lassitude, inability to feel, pessimistic thoughts, and suicidal thoughts) which psychiatrists use to measure the severity of depressive episodes in patients with mood disorders. In some embodiments, the therapeutic effect is a decrease from baseline in MADRS score at the end of a treatment period (e.g., 14 days after administration).

Pain

The dosage forms and compositions described herein may be useful in the treatment of pain. In some embodiments, the pain comprises acute pain, chronic pain, neuropathic pain, inflammatory pain, nociceptive pain, central pain (e.g., thalamic pain), or migraine. In some embodiments, the pain comprises acute pain or chronic pain. In some embodiments, the pain comprises neuropathic pain, inflammatory pain, or nociceptive pain. In some embodiments, the pain comprises central pain (e.g., thalamic pain). In some embodiments, the pain comprises migraine.

In some embodiments, the methods described herein further comprise identifying a subject having pain (e.g., acute pain, chronic pain, neuropathic pain, inflammatory pain, nociceptive pain, central pain (e.g., thalamic pain), or migraine) prior to administration of a dosage form or composition described herein (e.g., a dosage form or composition including a compound of Formula (I) or a pharmaceutically acceptable salt thereof (e.g., the compound of formula (II))).

Tremor

The methods described herein can be used to treat tremor, for example a dosage or composition disclosed herein can be used to treat cerebellar tremor or intention tremor, dystonic tremor, essential tremor, orthostatic tremor, parkinsonian tremor, physiological tremor, or rubral tremor. Tremor includes hereditary, degenerative, and idiopathic disorders such as Wilson's disease (hereditary), Parkinson's disease (degenerative), and essential tremor (idiopathic); metabolic diseases; peripheral neuropathies (associated with Charcot-Marie-Tooth, Roussy-Levy, diabetes mellitus, complex regional pain syndrome); toxins (nicotine, mercury, lead, carbon monoxide, manganese, arsenic, toluene); drug-induced (neuroleptics tricyclics, lithium, cocaine, alcohol, adrenaline, bronchodilators, theophylline, caffeine, steroids, valproate, amiodarone, thyroid hormones, vincristine); and psychogenic disorders. Clinical tremor can be a neuropathic tremor, and can be classified into physiologic tremor, enhanced physiologic tremor, essential tremor syndromes (including classical essential tremor), primary orthostatic tremor, task- and position-specific tremor, dystonic tremor, parkinsonian tremor, cerebellar tremor, Holmes' tremor (i.e., rubral tremor), palatal tremor, toxic or drug-induced tremor, and psychogenic tremor. The tremor may be familial tremor.

Tremor is an involuntary, rhythmic, oscillation of one or more body parts (e.g., hands, arms, eyes, face, head, vocal folds, trunk, and/or legs).

Cerebellar tremor or intention tremor is a slow, broad tremor of the extremities that occurs after a purposeful movement. Cerebellar tremor is caused by lesions in or damage to the cerebellum or pathways resulting from, e.g., tumor, stroke or other focal lesion disease (e.g., multiple sclerosis) or a neurodegenerative disease.

Dystonic tremor occurs in individuals affected by dystonia, a movement disorder in which sustained involuntary muscle contractions cause twisting and repetitive motions and/or painful and abnormal postures or positions. Dystonic tremor may affect any muscle in the body. Dystonic tremors occur irregularly and often can be relieved by complete rest or certain sensory maneuvers.

Essential tremor or benign essential tremor is the most common type of tremor. Essential tremor may be mild and nonprogressive in some, and may be slowly progressive, starting on one side of the body but typically affecting both sides. The hands are most often affected, but the head, voice, tongue, legs, and trunk may also be involved. Tremor frequency may decrease as the person ages, but severity may increase. Heightened emotion, stress, fever, physical exhaustion, or low blood sugar may trigger tremors and/or increase their severity. Symptoms generally evolve over time and can be both visible and persistent following onset.

Orthostatic tremor is characterized by fast (e.g., greater than 12 Hz) rhythmic muscle contractions that occurs in the legs and trunk immediately after standing. Cramps are felt in the thighs and legs and the patient may shake uncontrollably when asked to stand in one spot. Orthostatic tremor may occur in patients with essential tremor.

Parkinsonian tremor is caused by damage to structures within the brain that control movement. Parkinsonian tremor is typically seen as a "pill-rolling" action of the hands that may also affect the chin, lips, legs, and trunk. Onset of parkinsonian tremor typically begins after age 60. Movement starts in one limb or on one side of the body and can progress to include the other side.

Rubral tremor is characterized by coarse slow tremor which can be present at rest, at posture, and with intention. The tremor is associated with conditions that affect the red nucleus in the midbrain, such as a stroke.

In some embodiments, the tremor is selected from essential tremor, Parkinson's tremor, or Cerebellar tremor.

The efficacy of the compound or composition described herein for treating essential tremor can be measured by methods known in the art, such as the methods described in the following references: Ferreira, J. J. et al., "MDS Evidence-Based Review of Treatments for Essential Tremor," *Mov. Disord.* 2019 July; 34(7):950-958; Elble, R. et al., "Task Force Report: Scales for Screening and Evaluating Tremor,"*Mov. Disord.* 2013 November; 28(13):1793-800; Deuschl G. et al., "Treatment of patients with essential tremor," *Lancet Neurol.* 2011; 10:148-61; and Reich S. G. et al., "Essential Tremor," *Med. Clin. N. Am.* 2019; 103:351-356. The disclosures of the references are herein incorporated in their entirety.

In some embodiments, the methods described herein result in at least 25% reduction in the upper limb tremor score, wherein the tremor score may be converted to amplitude, as compared to a baseline. For example, in certain embodiments, the methods described herein result in about 40% mean reduction in tremor amplitude as measured by The Essential Tremor Rating Assessment Scale (TETRAS) upper limb score, described, for example, in Elble, R. J., "The Essential Tremor Rating Assessment Scale," *J. Neurol. Neuromed.* 2016; 1(4):34-38. In some embodiments, the methods described herein result in at least 25% reduction in TETRAS performance score as compared to the baseline. In some embodiments, the methods described herein result in at least 35% average reduction in symptom severity as compared to the baseline, as measured by TETRAS performance score.

Ataxia

Ataxia, including both cerebellar ataxia and spinal ataxia (e.g., posterior spinal ataxia), generally involves the loss or failure of coordination. Patients exhibiting ataxia may have difficulty regulating the force, range, direction, velocity, and rhythm involved in posture, balance, and limb movement. Ataxia of the trunk, for example, can result in increased postural sway, and an inability to maintain the center of gravity over the base of support. Ataxia and primary or secondary symptoms of ataxic gait and tremor of the limbs may be accompanied by speech disturbance, dysphagia, abnormal ventilation and speech, and involuntary eye movements, dystonia, pyramidal or extrapyramidal symptoms, thereby substantially interfering with the activities of daily life.

As noted above, ataxia may result from a wide range of underlying diseases and conditions in a patient, including cerebellar and neurodegenerative disorders and diseases resulting from chronic or long-term exposure to toxins. Symptoms of ataxia may result from a wide range of diseases, disorders, and environmental factors, including infectious diseases, metabolic diseases, neurodegenerative diseases, genetic diseases, vascular diseases, neoplastic diseases, demyelinating diseases, neuromuscular diseases, and diseases resulting from long-term or chronic exposure to toxins (including drugs and alcohol), among a variety of others; in one embodiment, for example, the ataxia is the result of a metabolic disease, a neurodegenerative disease, a vascular disease, a neuromuscular disease, or a disease resulting from long-term or chronic exposure to toxins. Diseases, disorders, syndromes, and conditions that may result in ataxic symptoms that may be treated according to the methods described herein include, but are not limited to, amyotrophic lateral sclerosis, benign paroxysmal positional vertigo, cerebellar ataxia type 1 (autosomal recessive), cerebellar ataxias (autosomal recessive), cerebellar ataxias (dominant pure), cerebellar cortical atrophy, cerebellar degeneration (subacute), cerebellar dysfunction, cerebellar hypoplasia, cerebellar hypoplasia (endosteal sclerosis), cerebellar hypoplasia (tapetoretinal degeneration), cerebelloparenchymal autosomal recessive disorder 3, cerebelloparenchymal disorder V, cerebellum agenesis (hydrocephaly), cerebral amyloid angiopathy (familial), cerebral palsy, demyelinating disorder, dorsal column conditions, dysautonomia, dysequilibrium syndrome, dysethesis, endocrine diseases, diseases caused by chronic exposure to toxins (e.g., alcohol, drugs, antiepileptics, neuroleptics), Fragile X/Tremor ataxia syndrome, Friedreich's ataxia, frontal lobe dysfunction, genetic diseases, granulomatous angiitis of the central nervous system, Hallervorden-Spatz disease, hereditary motor and sensory neuropathy, hydrocephalus (e.g., low or normal pressure), hypotonia, congenital nystagmus, ataxia and abnormal auditory brainstem response, infantile onset spinocerebellar ataxia, Machado-Joseph disease, Meniere's disease, metabolic disorders, Miller Fisher Syndrome, Minamata disease, multiple sclerosis, muscular dystrophy, Myoclonus-ataxia, neurodegenerative diseases, olivopontocerebellar atrophy, paraneoplastic disorders, parkinsonism (atypical), peroneal muscular atrophy, phenyloin toxicity, posterior column ataxia with retinitis pigmentosa, post-polio syndrome, severe damage to the brain (caused by, e.g., head injury, brain surgery, multiple sclerosis or cerebral palsy, chronic alcohol/drug abuse, chronic exposure to toxins, viral infections, or brain tumor), spastic hemiparesis, spastic paraplegia 23, spastic paraplegia glaucoma precocious puberty, SPG, spinocerebellar ataxia, spinocerebellar ataxia (amyotrophy—deafness), spinocerebellar ataxia (dysmorphism), spinocerebellar ataxia 11, spinocerebellar ataxia 17, spinocerebellar ataxia 20, spinocerebellar ataxia 25, spinocerebellar ataxia 29, spinocerebellar ataxia 42, spinocerebellar ataxia 3, spinocerebellar ataxia (autosomal recessive 1), spinocerebellar ataxia (autosomal recessive 3), spinocerebellar ataxia (autosomal recessive 4), spinocerebellar ataxia (autosomal recessive 5), spinocerebellar ataxia (autosomal recessive, with axonal neuropathy), spinocerebellar ataxia (Machado-Joseph type II), spinocerebellar ataxia (X-linked, 2), spinocerebellar ataxia (X-linked, 3), spinocerebellar ataxia (X-linked, 4), spinocerebellar degenerescence (book type), stroke (e.g., acute or hemorrhagic), vertebral artery dissection, vertebral-basilar insufficiency, and diseases caused by vitamin deficiencies, among a variety of others. In one embodiment, the ataxia is the result of a disease selected from Spinocerebellar ataxia, Friedriech's ataxia, and fragile X/tremor ataxia syndrome. In another particular embodiment, the ataxia is the result of Spinocerebellar ataxia or fragile X/tremor ataxia syndrome.

Tinnitus

Methods of treating tinnitus in a subject in need thereof are provided herein and comprise administering a dosage form or composition as disclosed herein. Tinnitus is a condition in which those affected perceive sound in one or both ears or in the head when no external sound is present. Often referred to as "ringing" in the ears, tinnitus can occur intermittently or consistently with a perceived volume ranging from low to painfully high. However, the perceived volume of tinnitus can vary from patient to patient where an objective measure of tinnitus volume in one patient may be perceived as painful but, in another patient, the same volume may be perceived as subtle.

Sleep Disorders

Methods of treating or preventing sleep disorder (e.g., narcolepsy) comprising administering a dosage or composition disclosed herein are provided herein. For example, a sleep disorder may be a central disorder of hypersomnolence, narcolepsy type I, narcolepsy type II, idiopathic hypersomnia, Kleine-Levin syndrome, hypersomnia due to a medical disorder, hypersomnia due to a medication or substance, hypersomnia associated with a psychiatric disorder, insufficient sleep syndrome, circadian rhythm sleep-wake disorders, delayed sleep-wake phase disorder, advanced sleep-wake phase disorder, irregular sleep-wake rhythm, non-24-hour sleep-wake rhythm disorder, shift work disorder, jet lag disorder, or circadian rhythm sleep-wake disorder not otherwise specified (NOS).

Combination Therapy

A dosage form or composition described herein (e.g., for use in modulating a T-type calcium ion channel) may be administered in combination with at least one other agent or therapy. A subject to be administered a compound disclosed herein may have a disease, disorder, or condition, or a symptom thereof, that would benefit from treatment with another agent or therapy. In certain embodiments, these diseases or conditions can relate to epilepsy or an epilepsy syndrome (e.g., absence seizures, juvenile myoclonic epilepsy, or a genetic epilepsy) or tremor (e.g., essential tremor).

Antiepilepsy Agents

Anti-epilepsy agents include brivaracetam, carbamazepine, clobazam, clonazepam, diazepam, divalproex, eslicarbazepine, ethosuximide, ezogabine, felbamate, gabapentin, lacosamide, lamotrigine, levetiracetam, lorazepam, oxcarbezepine, permpanel, phenobarbital, phenytoin, pregabalin, primidone, rufinamide, tigabine, topiramate, valproic acid, vigabatrin, and zonisamide.

Analgesics

Analgesics are therapeutic agents that are used to relieve pain. Examples of analgesics include opiates and morphinomimetics, such as fentanyl and morphine; paracetamol; NSAIDs, and COX-2 inhibitors. Given the ability of the compounds disclosed herein to treat pain via inhibition of T-type calcium channels (e.g., Cav3.1, Cav3.2, and Cav3.3), combination with analgesics are particularly envisioned.

Tremor Medications

Tremor medications include propranolol, primidone, clonazepam, diazepam, lorazepam, alprazolam, gabapentin, topiramate, topamax, neurontin, atenolol, klonopin, alprazolam, nebivolol, carbidopa/levodopa, clonazepam, hydrochlorothiazide/metoprolol, gabapentin enacarbil, labetalol, lactulose, lamotrigine, metoprolol, nadolol, hydrochlorothiazide, and zonisamide.

EXAMPLES

In order that the embodiments described herein may be more fully understood, the following examples are set forth. The synthetic and biological examples described in this application are offered to illustrate the compounds, pharmaceutical compositions, and methods provided herein and are not to be construed in any way as limiting their scope.

Example 1: Analysis of Crystallinity of the Compound of Formula (II) by X-Ray Power Diffraction Polymorph screening of the compound of formula (II) was carried out, and a stable solid state form (referred to as Form C) was identified. Crystallinity of Form C was analyzed by XRPD.

The XRPD analysis was performed using Bruker D8 ADVANCE and the following conditions.

Bragg Brentano geometry.

2θ range: 3° to 40°.

Step size: 0.02°.

Step time: 0.25 sec.

Slits: 0.3.

Sample rotation on: 15 rpm.

Copper $K_\alpha$ radiation.

Zero background silicon filled sample holder was used.

The XRPD of Form C of the compound of formula (II) is shown in FIG. 1. The positions and relative intensities of the highest intensity 10 peaks of the XRPD pattern of Form C are shown in Table 1. The sample is highly crystalline and shows no evidence of any baseline offset indicative of significant amorphicity.

TABLE 1

| XRPD peak list (10 strongest reflections) for form C | | | |
|---|---|---|---|
| Peak | d spacing (Å) | °2θ | % Relative intensity |
| 1 | 3.3 | 26.6 | 100 |
| 2 | 5.5 | 16.2 | 94.2 |
| 3 | 5.1 | 17.4 | 93.5 |
| 4 | 3.9 | 22.6 | 73.8 |
| 5 | 7.7 | 11.5 | 58.6 |
| 6 | 3.7 | 23.9 | 50.8 |
| 7 | 4.8 | 18.3 | 47.5 |
| 8 | 4.6 | 19.2 | 44.7 |
| 9 | 4.8 | 18.5 | 42.4 |
| 10 | 4.4 | 20.0 | 41.1 |

Preparation of Form C

A solution of the free base of the compound of formula (I) was cooled to 0° C. to 10° C. over 1 hour. Ethyl acetate/HCl (10-12%, 53.5 L, prepared in house from ethyl acetate and anhydrous HCl gas) was slowly added to the batch over 30 minutes while maintaining the temperature between 0° C. and 10° C. The batch was warmed to 25° C. to 30° C. over 1.25 hours and was held at this temperature for 4 hours. Vacuum (600-700 mmHg) was applied, and the batch was distilled below 33° C. for 6.25 hours at which point the volume of the distillate was 115 L. The batch was cooled to 25° C. to 30° C. and diisopropyl ether (53.5 L, 5 vol) was added. The batch was held at 25° C. to 30° C. with stirring for 2 hours, then filtered through a Nutsche filter NF202 under nitrogen atmosphere and sucked dry for 30 minutes. The cake was slurry/washed twice with diisopropyl ether (10.7 L, 1 vol) and suck dried for 30 minutes to 1 hour. This material was dried in a vacuum drier VD201 at 65° C. to 70° C. under vacuum (600-650 mmHg) for 12 hours, until the water content of the cake was not more than 2.0 wt %, to give Form C of the compound of formula (II) (10.01 kg, 90% yield, 0.45% water by KF).

The polymorph screening identified another stable solid state form (referred to as Form B). Crystallinity of Form B was analyzed by XRPD.

The XRPD analysis was performed using Bruker D8 ADVANCE and the same conditions as described above for Form C.

The XRPD for Form B of the compound of formula (II) is shown in FIG. 7. The positions and relative intensities of the highest intensity 10 peaks of the XRPD pattern of Form B are shown in Table 2. The sample is highly crystalline and shows no evidence of any baseline offset indicative of significant amorphicity.

TABLE 2

| XRPD peak list (10 strongest reflections) for form B | | | |
|---|---|---|---|
| Peak | d spacing (Å) | °2θ | % Relative intensity |
| 1 | 4.1 | 21.9 | 100 |
| 2 | 4.8 | 18.5 | 61.5 |
| 3 | 5.0 | 17.8 | 53.5 |
| 4 | 8.6 | 10.2 | 49 |
| 5 | 4.3 | 20.5 | 46.1 |
| 6 | 3.5 | 25.2 | 44.1 |
| 7 | 5.3 | 16.9 | 37.7 |
| 8 | 3.7 | 24.2 | 36.5 |
| 9 | 3.1 | 28.6 | 33.9 |
| 10 | 4.2 | 21.2 | 32.4 |

Preparation of Form B

A material showing the XRPD pattern of Form B was prepared from ethyl acetate by controlled solvent evaporation. Approximately 200 mg of a compound of formula (II) was placed in a 30 to 50 mL glass vial/beaker. 20 mL of ethyl acetate was added and the sample was vortex mixed/sonicated for approximately one minute until a clear solution was obtained. The solution was filtered through a syringe filter (Durapore PVDF 0.22 μm centrifuge filter from Millipore) to remove potential seeds of the input solid state form. The solution was then stirred open to the environment at ambient conditions for 48 hours.

Example 2: Thermal Properties of Form C and Form B of the Compound of Formula (II)

Form C of the compound of formula (II) was further analyzed by DSC, TGA, and HSM. The compound of Form C has a high melting point and does not undergo any physical or chemical changes below 180° C.

DSC

The DSC of Form C of the compound of formula (II) was analyzed using Perkin Elmer Diamond DSC and the following conditions:

Aluminum pans under nitrogen purge gas.

Sample size: 1 to 5 mg.

Temperature range: 25° C. to 250° C.

Heating rate: 2° C./min, 5° C./min, 10° C./min.

The DSC thermogram for Form C of the compound of formula (II) is shown in FIG. 2. A summary of the data obtained is shown in Table 3. The obtained thermogram shows a single sharp endotherm with an onset temperature of 226.6° C. due to melting of Form C.

TABLE 3

| DSC data obtained for form C of the compound of formula (II) | |
|---|---|
| Parameter | Event 1 (endothermic) |
| onset temp (° C.) | 226.6 |
| peak temp (° C.) | 230.9 |
| ΔH (J/g) | 101.8 |

TGA

The TGA analysis of Form C was conducted using perkin elmer Pyris 1 and the following conditions:

Platinum pan under nitrogen purge gas.

Sample size: 2 to 4 mg.

Temperature range: ambient to 300° C.

Heating rate: 10° C./min.

Figure 3:
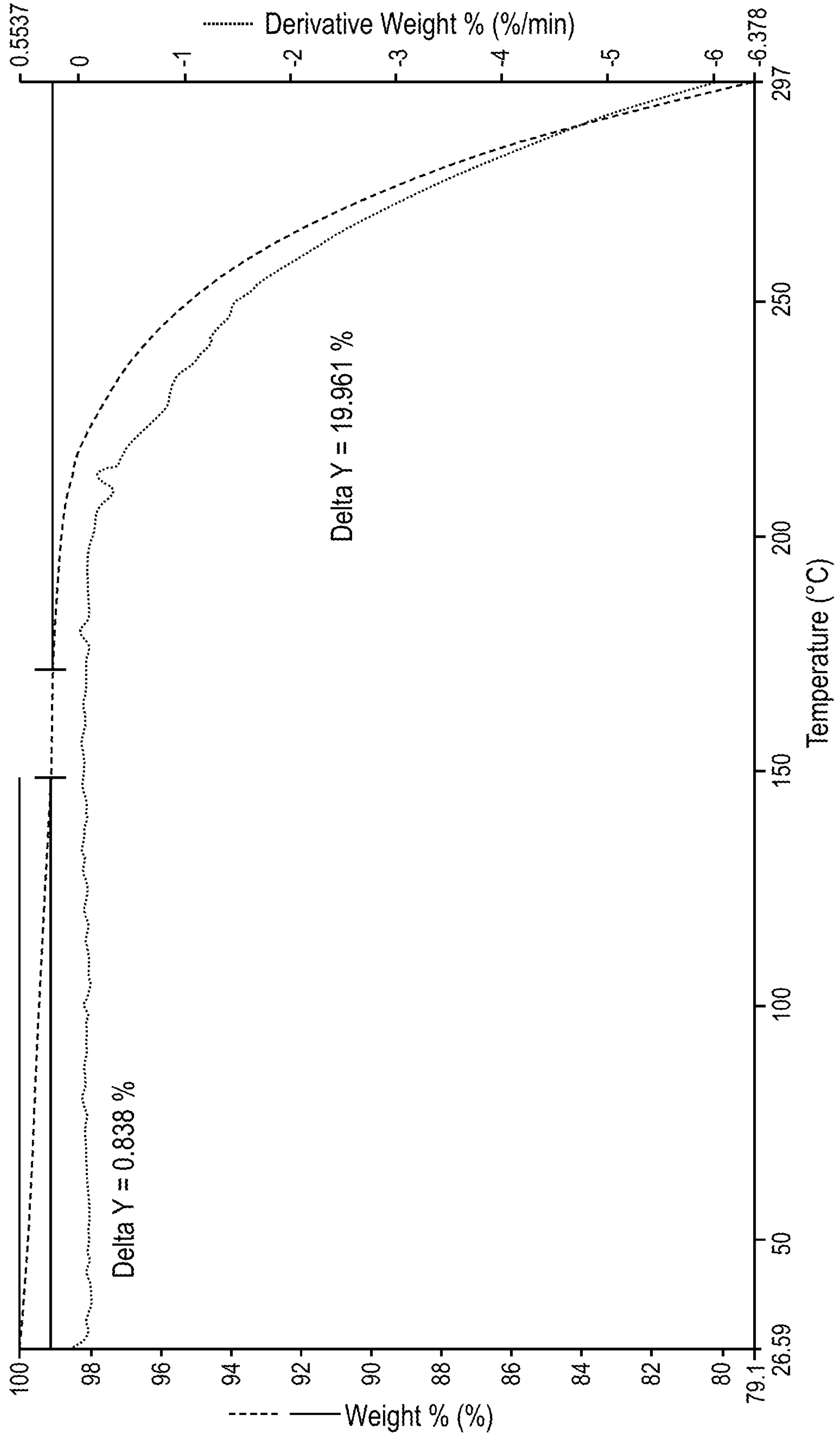
FIG. 3 is a thermogravimetric analysis (TGA) thermogram of Form C of the compound of formula (II).

The TGA thermogram (FIG. 3) shows weight loss of approximately 0.8% w/w when heating from ambient to 150° C., indicating that Form C of the compound of formula (II) is not a hydrate or solvate (the theoretical weight loss for monohydrate is 4.1% w/w).

TABLE 4

| TGA data obtained for form C of the compound of formula (II) | |
|---|---|
| Event | Weight loss |
| 1 | 0.8% w/w (ambient to 150° C.) |
| 2 | 20.0% w/w (175° C. to 300° C.) |

HSM

Figure 4:
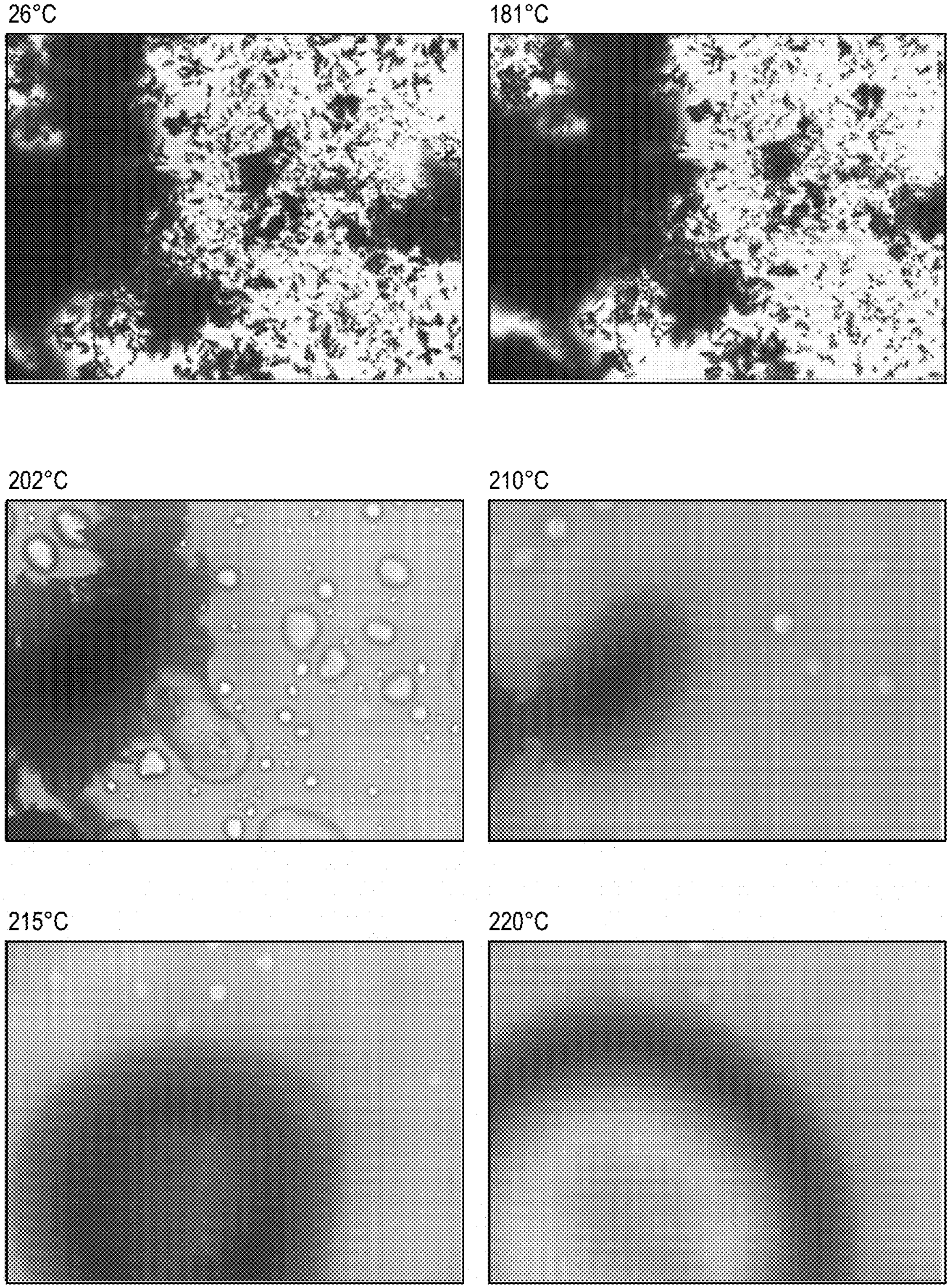
FIG. 4 are hot stage microscopy (HSM) photomicrographs of Form C of the compound of formula (II).

The HSM on Form C of the compound of formula (II) was conducted at ambient temperature to 300° C. (no sample equilibrium) with 10° C./min or 20° C./min heating rate. FIG. 4 shows the HSM photomicrographs of Form C of the compound of formula (II). The experiment confirmed that the material remained unchanged up to approximately 180° C. The material began to melt at approximately 201° C., and the melt of the final particle was complete at approximately 215° C. The endothermic event seen in the DSC thermogram of FIG. 2 with an onset temperature of 227° C. corresponded to the melt.

Figure 8A:
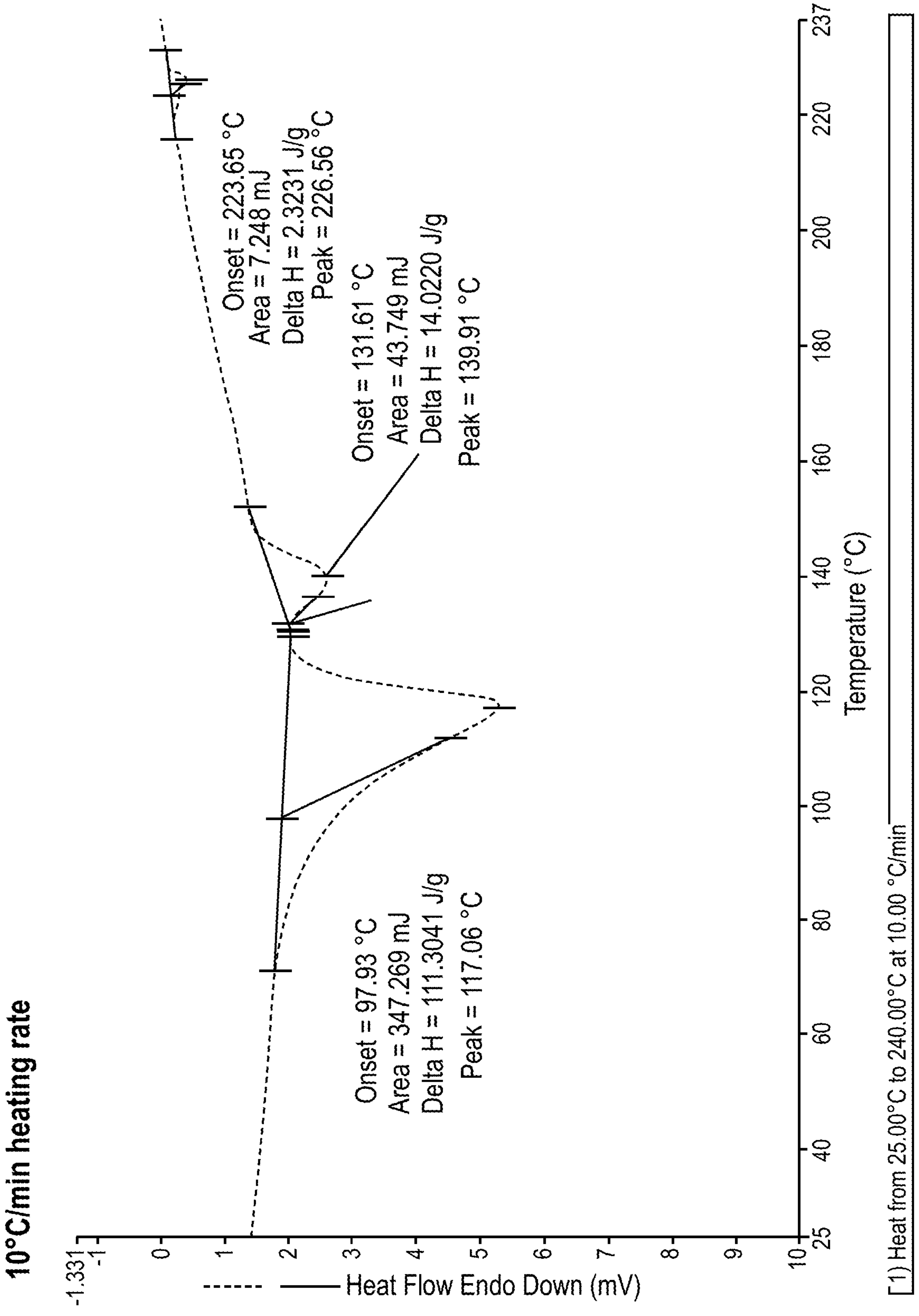
FIG. 8A is a DSC thermogram of Form B of the compound of formula (II) at a heating rate of 10° C./min.
Figure 8B:
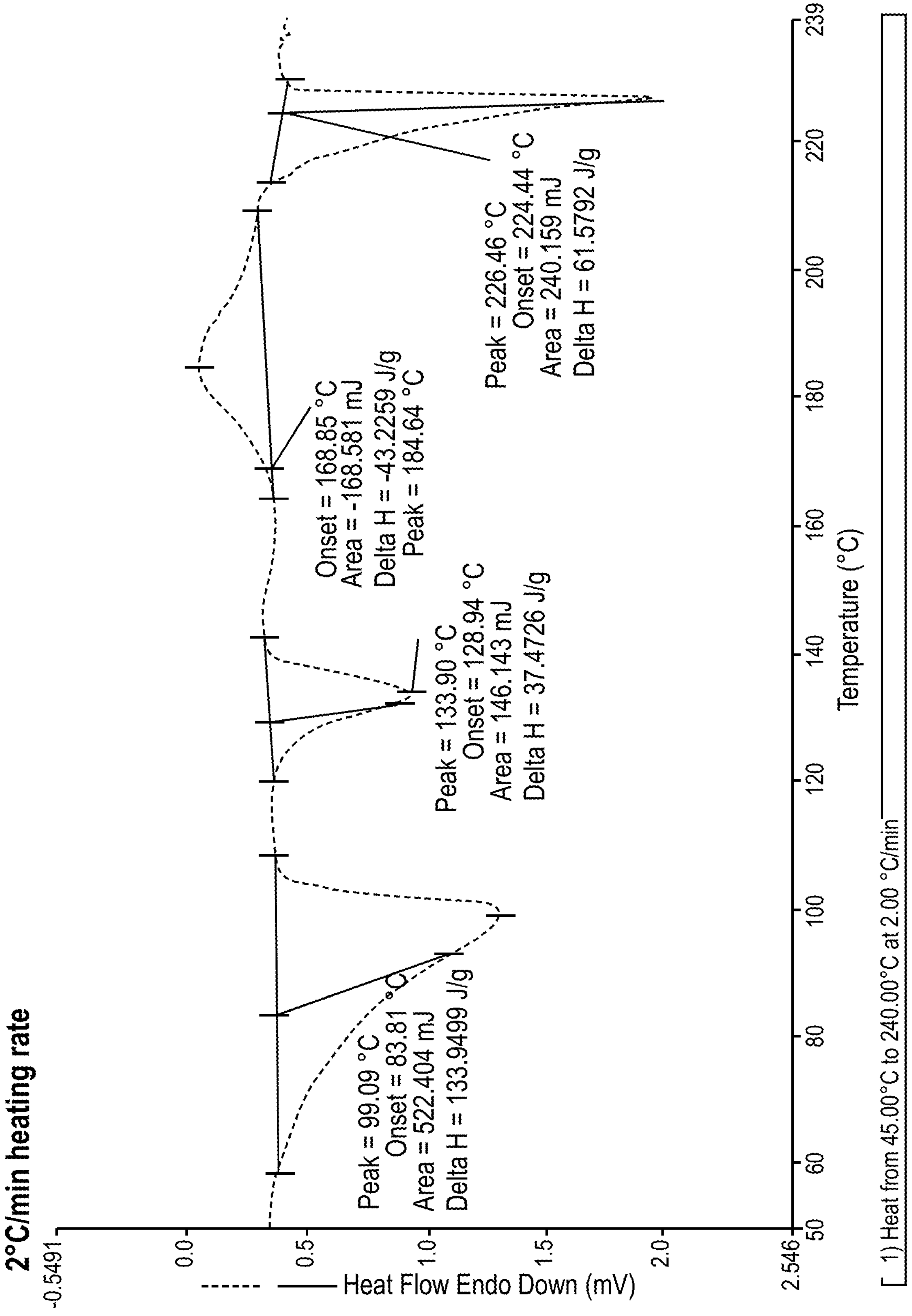
FIG. 8B is a DSC thermogram of Form B of the compound of formula (II) at a heating rate of 2° C./min.

Form B of the compound of formula (II) was further analyzed by DSC, TGA, and HSM. The DSC thermogram for Form B material at a heating rate of 10° C./min is shown in FIG. 8A, and the and the DSC thermogram for Form B at a heating rate of 2° C./min is shown in FIG. 8B. A summary of the data obtained is shown in Table 5, below. The DSC thermogram with heating rate 10° C./min showed three endothermic events. The first endotherm with an onset temperature of approximately 98° C. can be assigned to the weight loss event seen in the TGA experiment (75° C. to 125° C.), likely due to water or solvent loss. A slower heating rate of 2° C./min was used to investigate the thermal events seen at higher temperatures. The DSC thermogram recorded with heating rate 2° C./min shows four major events, three endothermic events and one exothermic event. The first endothermic event (onset temperature 84° C.) is likely due to water or solvent loss. The second event (onset temperature 129° C.) is due to melting of the dehydrated or desolvated form of the compound. An exothermic event (onset temperature 169° C.) was observed following this melt which corresponded to crystallisation seen in HSM (likely to give Form B material). The final endothermic event (onset temperature 224° C.) was shown to be a melt by HSM and corresponds to the melt of Form C material.

TABLE 5

DSC data obtained for pattern B of the compound of formula (II)

10° C./min heating rate

| Parameter | Event 1 (endothermic) | Event 2 (endothermic) | Event 3 (endothermic) |
|---|---|---|---|
| Onset temperature (° C.) | 97.9 | 131.6 | 223.7 |
| Peak temperature (° C.) | 117.1 | 139.9 | 226.6 |
| ΔH (J/g) | 111.3 | 14.0 | 2.3 |

2° C./min heating rate

| Parameter | Event 1 (endothermic) | Event 2 (endothermic) | Event 3 (exothermic) | Event 4 (endothermic) |
|---|---|---|---|---|
| Onset temperature (° C.) | 83.8 | 128.9 | 168.9 | 224.4 |
| Peak temperature (° C.) | 99.1 | 133.9 | 184.6 | 226.5 |
| ΔH (J/g) | 134.0 | 37.5 | −43.2 | 61.6 |

Figure 9:
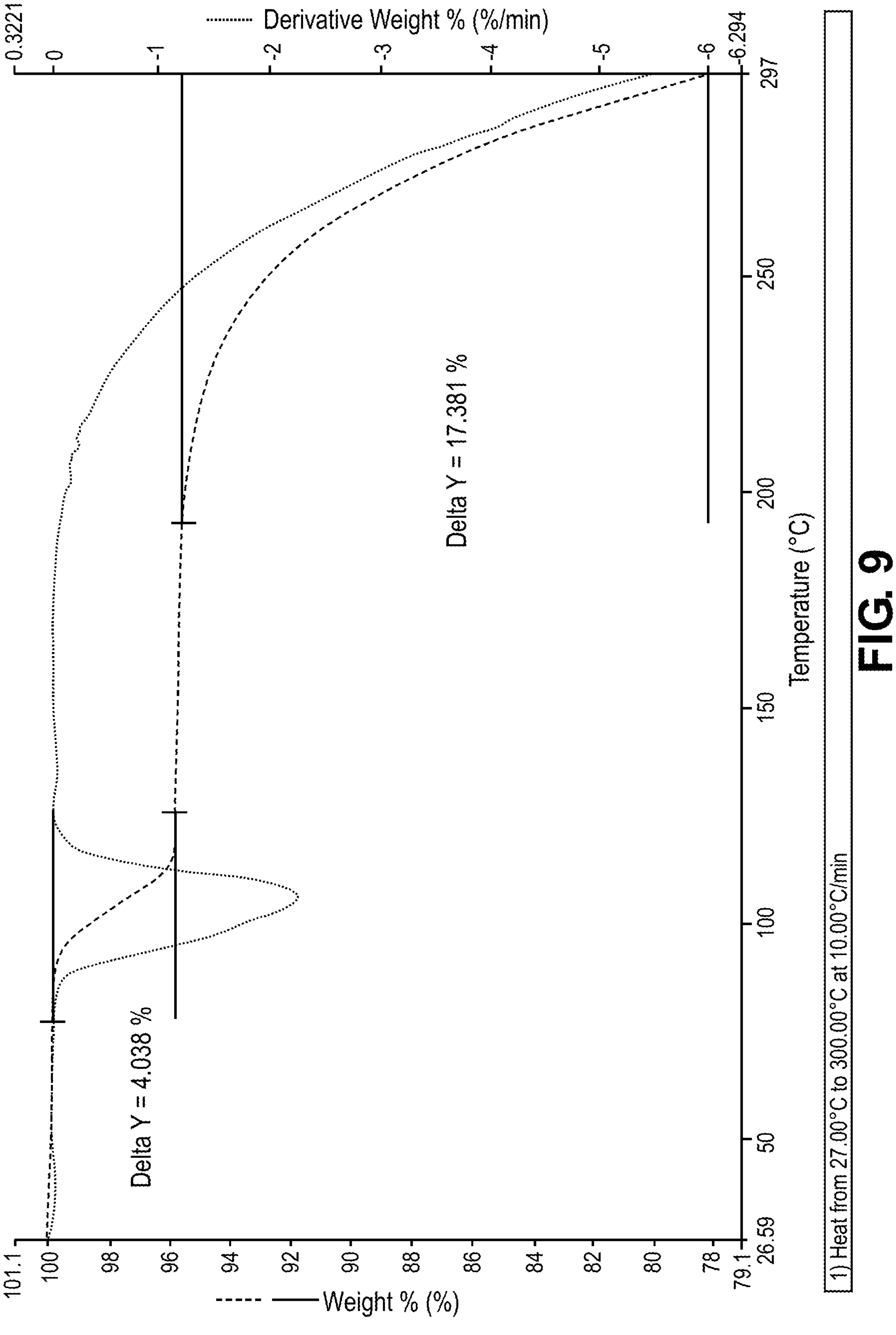
FIG. 9 is a TGA thermogram of Form B of the compound of formula (II).

The TGA thermogram for Form B material is shown in FIG. 9. A summary of the data obtained is shown in Table 6. The TGA thermogram shows a step-wise weight loss typical of hydrates of approximately 4.0% w/w over the temperature range 75° C. to 125° C. The theoretical weight for a monohydrate is 4.1%, thereby indicating that Form B is a possible hydrate. It is not likely to be a solvate, as it comes from different solvents and different solvates are unlikely to give the same diffraction pattern. This weight loss event corresponds to the first endotherm observed in the DSC thermogram for Form B. A significant weight loss of approximately 17% w/w was observed over a temperature range of 195° C. to 300° C. Examination of the residue from the experiment showed it to be a brown mass, indicating degradation had occurred. Hot stage microscopy confirmed a melt at approximately 200° C. followed by decomposition.

TABLE 6

TGA data obtained for pattern B of the compound of formula (II)

| Event | Weight loss |
|---|---|
| 1 | 4.0% w/w (75° C. to 125° C.) |
| 2 | 17.4% w/w (195° C. to 300° C.) |

Figure 10:
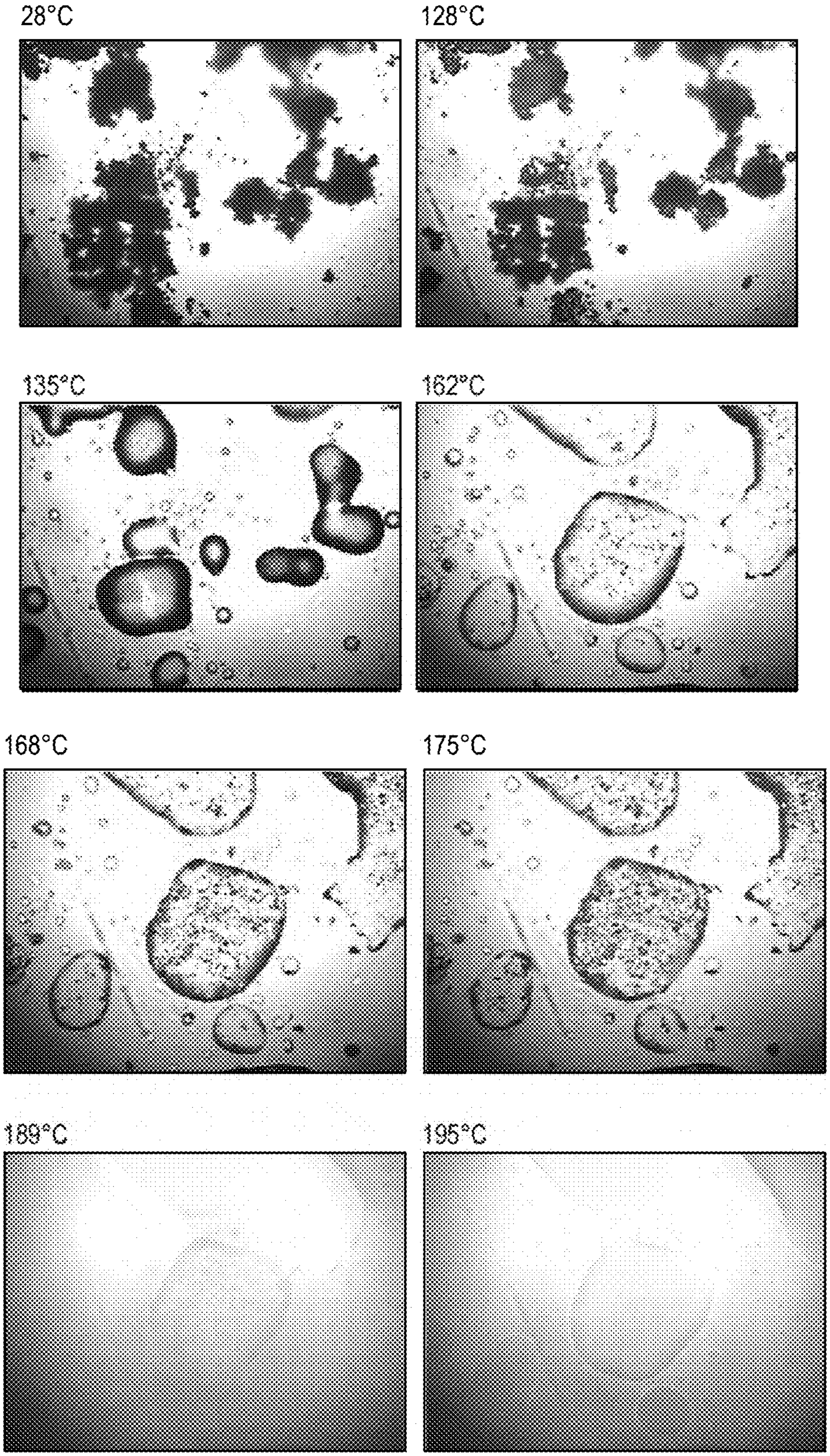
FIG. 10 are HSM photomicrographs of Form B of the compound of formula (II).

HSM on Form B material showed the appearance of the material to be unchanged up to a temperature of 128° C. The material began to melt at 128° C., and the melt of the final particle was complete at a temperature of approximately 135° C. (see FIG. 10). This confirms the event with an onset temperature of 227° C. observed in DSC was due to a melt. Recrystallization from the melt was observed between 161° C. to 175° C., while change in the colour of the melt was observed concurrently with the melting of the recrystallized solid between 189° C. to 195° C. Degradation of the compound may occur differently during HSM when compared to DSC. HSM is carried out under an atmosphere of air; DSC is carried out under an inert atmosphere of nitrogen. Therefore, oxidative processes may occur during HSM that will not occur during DSC.

Example 3: Modified Release Tablet Formulations of the Compound of Formula (II)

Formulations

In a Phase 1, single-, ascending-dose study of immediate-release ("IR") capsules, CNS-related events and psychiatric-related adverse events were the most commonly reported adverse events and typically occurred around the time of maximum plasma concentrations ($T_{max}$). In a subsequent cohort within the same study, administration of 40 mg of IR capsules as four 10-mg doses at 2-hour intervals reduced the mean $C_{max}$ value by ~50% of the value that was observed after administration of a single, oral 40-mg dose of the compound of formula (II), and mild headache and mild somnolence were the only adverse events that were reported after the split dose. Given these findings, modified-release ("MR") tablet formulations of the compound of formula (II) were developed in an attempt to reduce the $C_{max}$ of a given dose, while maintaining the overall AUC.

The composition of the immediate release capsule of the compound of formula (II) is provided in Table 7 below.

TABLE 7

| Formulation of the compound of formula (II) for immediate release capsules | |
|---|---|
| Ingredients | Formulation |
| the compound of formula (II) (HCl salt, form C) | 20.00 mg |
| Hypromellose | 5.50 mg |
| Microcrystalline cellulose | 41.35 mg |
| Mannitol | 39.30 mg |
| Croscarmellose sodium | 2.75 mg |
| Magnesium stearate | 1.10 mg |
| Opaque white size# 4 hard gelatin capsules | 1 each |
| Total weight | 110 mg |

Three initial tablet formulations of the compound of formula (II) (Form C) with different release rate profiles were prepared: (1) formulation 1 (wherein about 80% of the compound of formula (I) is released within 2 hours after an administration to a subject), (2) formulation 2 (wherein about 80% of the compound of formula (I) is released within 5 hours), and (3) formulation 3 (wherein about 80% of the compound of formula (I) is released within 7 hours). The compositions of the formulations 1-3 are shown in Table 8. Each tablet contains 20 mg of the compound of formula (II).

TABLE 8

| Formulation of the compound of formula (II) for modified release tablets | | | |
|---|---|---|---|
| Ingredients | Formulation 1 (80% release rate of 2 hours) | Formulation 2 (80% release rate of 5 hours) | Formulation 3 (80% release rate of 7 hours) |
| the compound of formula (II) (form C) | 20.00 mg | 20.00 mg | 20.00 mg |
| Microcrystalline cellulose | 28.75 mg | 18.75 mg | 19.50 mg |
| Mannitol | 28.75 mg | 18.75 mg | 0 mg |
| Hypromellose | 20.00 mg | 40.00 mg | 58.00 mg |
| Colloidal silicon dioxide | 1.50 mg | 1.50 mg | 1.50 mg |
| Magnesium stearate | 1.00 mg | 1.00 mg | 1.00 mg |
| Opadry white 03K580000 | 3.00 mg | 3.00 mg | 3.00 mg |
| Total weight | 103.00 mg | 103.00 mg | 103.00 mg |

Manufacturing Process

The process to prepare the modified release tablets comprises 6 sequential steps: 1) sifting of all ingredients (the compound of formula (I) or a pharmaceutically acceptable salt thereof (e.g., formula (II)) and excipients), 2) blending of the compound with excipients (including intra granular lubrication), 3) roller compaction (including milling), 4) extra granular lubrication, 5) tablet compression, and 6) tablet coating.

Example 4: Pharmacokinetic Studies and Reported Adverse Events for the Modified Release Tablets after Single Dose Administration Modified release tablets of the compound of formula (II) were developed in an attempt to mitigate some of the adverse effects seen with immediate release capsules of the compound of formula (II). The reduction in $C_{max}$ and the delay in $t_{max}$ of three modified release tablet formulations of the compound of formula (II), relative to the immediate release capsule formulation of the compound of formula (II), were evaluated under fasting conditions in healthy volunteers in a Phase 1 study.

The Phase 1 study was a randomized, open-label, 4-way crossover study. Eligible subjects were randomized to 1 of 4 treatment sequences and received single 20-mg doses (the compound of formula (II)) of the immediate release capsule formulation of the compound of formula (II) and single 20-mg doses of the following 3 modified release tablet formulations of the compound of formula (II) in the fasted state: formulation 1 (80% release rate within 2 hours), formulation 2 (80% release rate within 5 hours), and formulation 3 (80% release rate within 7 hours). Study treatments were administered at 4 separate study visits, each of which was separated from the previous one by a minimum 1-week washout period.

Figure 5:
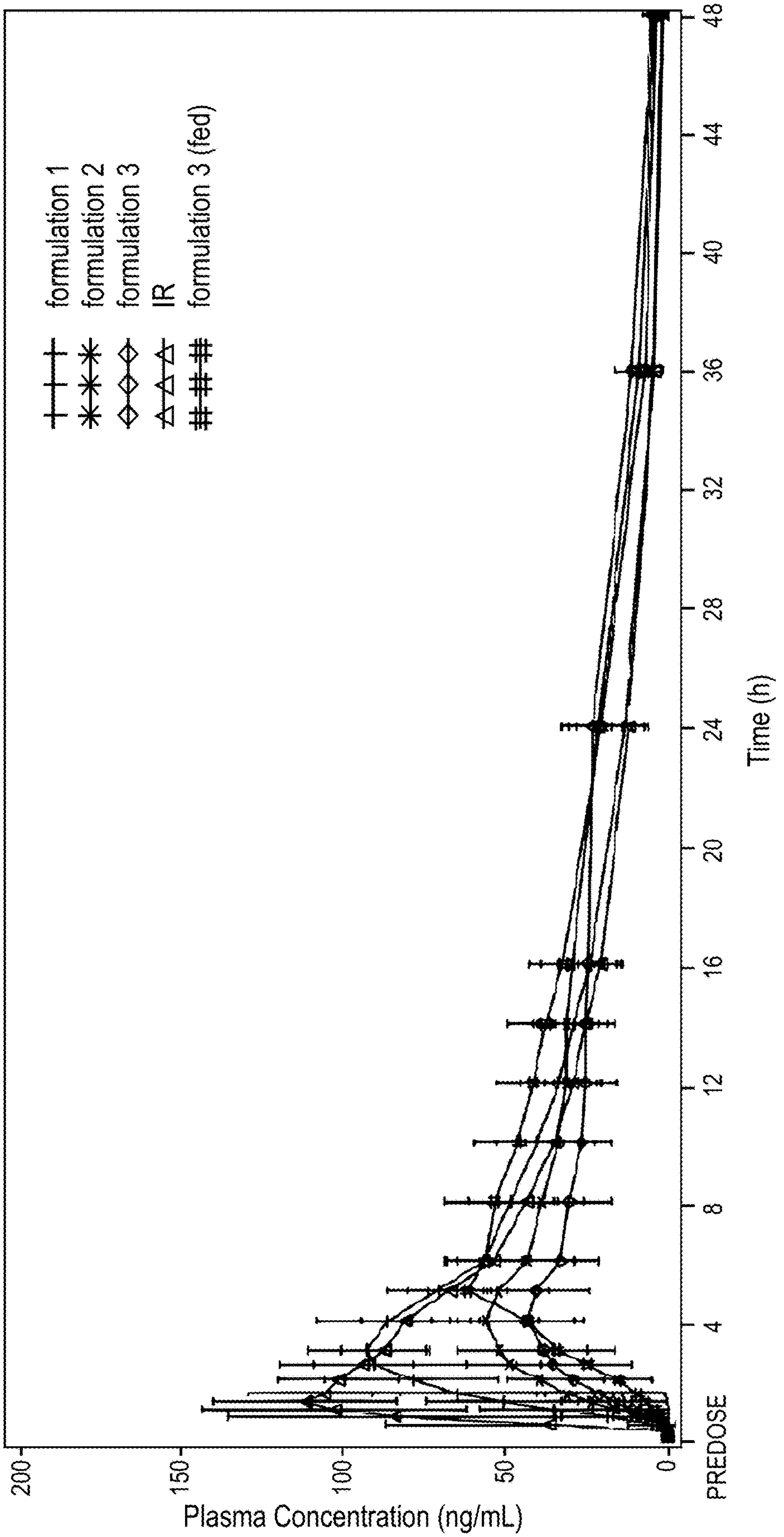
FIG. 5 is a graph showing mean concentration-time profiles of the compound of formula (II) after single 20 mg oral doses of the modified-release tablets (formulation 1, formulation 2, and formulation 3) and immediate-release (IR) capsule of the compound of formula (II).

FIG. 5 shows mean concentration-time profiles of the compound of formula (II), after single 20-mg oral doses of the modified-release tablets of formulations 1-3 and the immediate-release capsule of the compound of formula (II).

After administration of 20 mg of the compound of formula (II) in the fasted state, plasma concentrations of the compound of formula (I) were quantifiable by 0.75 hours after administration of each of the modified release tablet formulations of the compound of formula (II) and after administration of the immediate release capsule formulation in the fasted state (FIG. 5). After reaching $C_{max}$, plasma concentrations of the compound of formula (II) declined in a biphasic manner after administration of both the immediate release capsule and the formulation 1 tablet in the fasted state. Plasma concentrations plateaued after reaching $C_{max}$ and then declined in a monophasic manner after administration of formulation 2 and formulation 3 tablets in the fasted state. The compound of formula (II) remained quantifiable for a minimum of 36 hours after administration of the immediate release capsule and formulation 1 tablet and for the duration of the 48-hour sampling period after administration of the formulation 2 and formulation 3 tablets.

The formulation 3 tablet in the fed state had declining plasma concentrations in a biphasic manner after reaching $C_{max}$. The compound of formula (II) remained quantifiable for the duration of the 48-hour sampling period after administration of the formulation 3 tablet in the fed state. (FIG. 5).

Table 9 summarizes the median $t_{max}$, the observed geometric mean $C_{max}$, the observed geometric mean $AUC_{last}$, and the $AUC_{inf}$ for the immediate release capsule, formulation 1 tablet (release rate of 2 hours), formulation 2 tablet (release rate of 5 hours), and formulation 3 tablet (release rate of 7 hours). The modified release formulations with longer release rates provided delayed $t_{max}$ values and reduced $C_{max}$ concentrations relative to the immediate release capsule while maintaining overall exposure as assessed by $AUC_{last}$. The observed $t_{1/2}$ was similar for all formulations at approximately 8 to 10 hours. There was no evidence to suggest that the rate of absorption influenced $t_{1/2}$. Intra-subject variability associated with $AUC_{last}$ was similar amongst the three modified release tablet formulations.

TABLE 9

Geometric mean values (CV % geometric mean) of pharmacokinetic parameters of the compound of formula (II) after single oral 20 mg doses of modified-release tablets and immediate-release capsule (Study Phase 1)

| Parameter | Modified Release Tablet Formulation Formulation 1 [Fasted] (N = 18) | Formulation 2 [Fasted] (N = 18) | Formulation 3 [Fasted] (N = 18) | Immediate Release Capsule [Fasted] (N = 18) |
|---|---|---|---|---|
| $t_{lag}$ (h)[1] | 0.250 (0.00-0.52) | 0.250 (0.25-0.50) | 0.250 (0.25-0.50) | 0.250 (0.00-0.50) |
| $t_{max}$ (h)[1] | 3.000 (1.50-5.00) | 4.000 (1.50-5.00) | 4.000 (2.50-24.00) | 1.250 (0.50-3.15) |
| $C_{max}$ (ng/mL) | 95.1 (25.4) | 56.4 (27.6) | 44.5 (35.9) | 127 (26.5) |
| $AUC_{last}$ (ng*h/mL) | 1020 (31.4) | 1010 (29.4) | 910 (29.9) | 1040 (24.0) |
| $AUC_{inf}$ (ng*h/mL) | 1050 (32.1) | 1050 (31.2) | 961 (35.1) | 1060 (24.9) |
| $AUC_{extrap}$ (%) | 1.91 (64.1) | 4.18 (42.7) | 5.71 (57.5) | 1.81 (51.1) |
| t½ (h) | 8.146 (18.5) | 9.349 (13.2) | 10.059 (15.2) | 7.948 (17.7) |
| Cl/F (mL/h) | 319 (32.1) | 317 (31.2) | 347 (35.1) | 315 (24.9) |
| $V_z$/F (mL) | 225 (25.3) | 256 (25.8) | 302 (29.1) | 217 (16.2) |

Abbreviations: $AUC_{extrap}$, percentage of the area extrapolated beyond the last quantifiable plasma concentration; $AUC_{inf}$, area under the plasma concentration-time curve from time of dosing to infinity; $AUC_{last}$, area under the plasma concentration-time curve from time of dosing to the last measurable concentration; $C_{max}$, maximum (peak) plasma drug concentration; Cl/F, apparent plasma clearance after oral administration; CV %, coefficient of variation expressed as a percentage; t½, terminal elimination half-life; MR—modified-release, $t_{lag}$, time prior to the first measurable (non-zero) concentration; $t_{max}$, time to reach maximum (peak) plasma drug concentration; $V_z$/F, apparent volume of distribution after oral administration.

[1]Median (range).

Of the 18 subjects who received single, oral 20-mg doses of the 3 modified release tablet formulations (formulations 1-3) or the IR capsule (see Example 4) in the fasted state, 17 subjects (94.4%) experienced at least one adverse event after administration of any of the formulations (see Table 10 below). At least one drug-related adverse event was reported in 15 of the 18 subjects (83.3%). No severe or serious adverse events were reported, and none of the subjects discontinued treatment with the study drug because of adverse events.

Consistent with the expected lower $C_{max}$ exposure of the compound of formula (I) for the MR tablets relative to the IR capsule, the percentage of subjects who experienced at least one adverse event and the percentage of subjects who experienced at least one drug-related adverse event were fewer after administration of each of the MR tablets than after administration of the IR capsule (Table 10). Among the MR tablets, the percentage of subjects who experienced any adverse event and the percentage of subjects who experienced any drug-related adverse event were smallest for the formulation 3. At least one adverse event was reported in 33.3% of the subjects after administration of the formulation 3 tablet, in 44.4% of the subjects after administration of the formulation 2 tablet, in 61.1% after administration of the formulation 1 tablet, and in 72.2% of the subjects after administration of the IR capsule. At least one drug-related adverse event was reported in 16.7% of the subjects after administration of the formulation 3 tablet, in 44.4% of the subjects after administration of the formulation 2 tablet, in 44.4% after administration of the formulation 1 tablet, and in 72.2% of the subjects after administration of the IR capsule.

The increase in percentage of subjects who experienced any adverse event and any drug-related adverse event was concentration dependent and, in general, correlated with the ordering of $C_{max}$ (formulation 3<formulation 2<formulation 1<IR capsule).

TABLE 10

Overall Summary of Treatment-Emergent Adverse Events After Single Oral 20-mg Doses of Tablets (formulations 1-3) and Immediate-Release Capsule in Fasted State (Safety Population)

| Number (%) of Subjects With | MR Tablet Formulation Formulation 1 (N = 18) n (%) | Formulation 2 (N = 18) n (%) | Formulation 3 (N = 18) n (%) | IR Capsule (N = 18) n (%) | All Formulations (N = 18) n (%) |
|---|---|---|---|---|---|
| At least one TEAE | 11 (61 1) | 8 (44 4) | 6 (33 3) | 13 (72 2) | 17 (94.4) |
| At least one drug-related TEAE[1] | 8 (44 4) | 8 (44 4) | 3 (16.7) | 13 (72.2) | 15 (83.3) |
| With at least one severe TEAE | 0 | 0 | 0 | 0 | 0 |
| With at least one SAE | 0 | 0 | 0 | 0 | 0 |

TABLE 10-continued

Overall Summary of Treatment-Emergent Adverse Events After Single Oral 20-mg Doses of Tablets (formulations 1-3) and Immediate-Release Capsule in Fasted State (Safety Population)

| | MR Tablet Formulation | | | IR | All |
|---|---|---|---|---|---|
| Number (%) of Subjects With | Formulation 1 (N = 18) n (%) | Formulation 2 (N = 18) n (%) | Formulation 3 (N = 18) n (%) | Capsule (N = 18) n (%) | Formulations (N = 18) n (%) |
| With at least one TEAE leading to discontinuation of study drug | 0 | 0 | 0 | 0 | 0 |

Abbreviations:
IR = immediate release,
MR = modified release,
SAE = serious adverse event,
TEAE treatment-emergent adverse event
[1]Drug-related adverse events are those for which the investigator assessed the relationship to the study drug as possible, probable, or certain.

Figure 16:
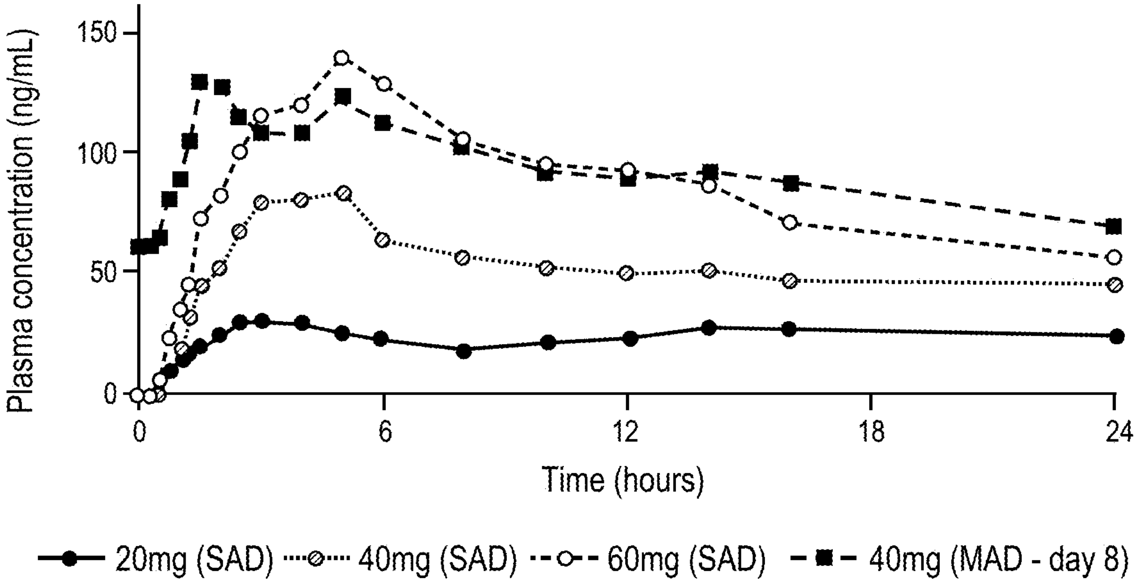
FIG. 16 shows exposure based on plasma concentration (ng/mL) for the modified release formulation 3 of the compound of formula (II), as described in Example 5, at single-ascending doses (SAD) of 20, 40, and 60 mg, and a multiple-ascending dose (MAD) of 40 mg on Day 8.

Example 5: Pharmacokinetic Studies of the Modified Release Tablets in Single and Multiple Ascending Doses This was a 2-part, Phase 1 double blind, placebo controlled trial to assess the safety, tolerability, pharmacokinetics, and pharmacodynamics (including the KSS, the KDT, the SQSQ and 24-hour EEG recordings), of single, ascending (Part A: 20, 40, and 60 mg) and multiple, ascending (Part B: 20 and 40 mg for 8 days) doses of the 20 mg tablet (formulation 3) in healthy participants. Based on the results of this trial, as shown in FIG. 16, following single oral doses of the 20 mg tablet (formulation 3), exposure to the compound of formula (I) increased with dose over the dose range from 20 mg to 60 mg. Variability in $C_{max}$ and AUC increased with increasing dose following a single oral dose of the 20 mg tablet formulation (formulation 3) (FIG. 16).

In this study, single and multiple (daily for 8 days) doses of 20 and 40 mg were well tolerated. Adverse events for the doses of 20 and 40 mg were transient and occurred at a rate similar to placebo. The following TEAEs were observed, all of which were mild to moderate:

For the 40 mg dose (n=6), the nervous system TEAEs of somnolence (33.3%), headache (33.3%) and dizziness (33.3%) were observed. The TEAEs also included fatigue (33.3%) and hot flash (33.3%). The following adverse events were also observed: ECG application site rash, EEG application site skin reaction, nausea, vision blurred, thermal burn (accidental) and euphoric mood in 16.7% of subject each.

For the 20 mg dose (n=6), the nervous system disorder TEAEs of somnolence (16.7%) and headache (33.3%), as well as nausea (33.3%), fatigue (16.7%), vomiting (16.7%) and dry throat (16.7%) were observed.

For placebo (n=4), nervous system TEAEs of headache (25%), somnolence (25%) and dizziness (25%), as well as fatigue (50%) and nausea (25%) were observed.

A single 60 mg administered to 6 healthy volunteers was not tolerated. 5 of the 6 participants were nauseated and 3 of the 6 participants vomited. In the multiple dose 20 mg and 40 mg groups, three subjects reported nausea with one subject also reporting vomiting; these events were mild in severity and resolved on Day 1 of dosing. No subjects reported nausea or vomiting after Day 1 of dosing. While a single dose of 60 mg was not well tolerated, the average peak drug levels (138 ng/mL) observed in the 40 mg group after eight days of treatment were greater than those seen with the single 60 mg dose (130 ng/mL) on Day 1 (FIG. 16). Accordingly, repeated administration of the 40 mg dosage form resulted in $C_{max}$ values that were associated with intolerable adverse effects when the 60 mg dose form was administered to patients as an initial dose. Yet repeated administration of the 40 mg dosage form was safely tolerated.

TABLE 11

Geometric Mean Values (Geometric CV %) After Single Oral Doses of 20 mg Tablet Formulation 3 (Part A)

| | Dose group | | |
|---|---|---|---|
| Parameter | 20 mg [20 mg formulation 3 Tablet × 1] (N = 6) | 40 mg [20 mg formulation 3 Tablet × 2] (N = 6) | 60 mg [20 mg formulation 3 Tablet × 3] (N = 6) |
| $t_{lag}$ (h)[1] | 0.250 (0.25-0.50) | 0.250 (0.25-0.75) | 0.250 (0.25-0.25) |
| $t_{max}$ (h)[1] | 8.50 (2.0-24.0) | 3.50 (3.0-5.0) | 5.50 (5.0-14.0) |
| $C_{max}$ (ng/mL) | 39.8 (13.0) | 85.8 (32.0) | 130 (59.3) |
| $AUC_{last}$ (ng*h/mL) | 853 (16.8) | 1730 (29.0) | 2570 (44.6) |
| $AUC_{24}$ (ng*h/mL) | 578 (14.2) | 1210 (30.5) | 1910 (42.9) |
| $AUC_{inf}$ (ng*h/mL) | 887 (19.3)[2] | 1840 (30.5) | 2470 (43.9)[2] |

TABLE 11-continued

Geometric Mean Values (Geometric CV %) After Single Oral Doses of 20 mg Tablet Formulation 3 (Part A)

| Parameter | Dose group: 20 mg [20 mg formulation 3 Tablet × 1] (N = 6) | 40 mg [20 mg formulation 3 Tablet × 2] (N = 6) | 60 mg [20 mg formulation 3 Tablet × 3] (N = 6) |
|---|---|---|---|
| $t_{1/2}$ (h) | 5.034 (104.1)[2] | 5.282 (39.7) | 3.299 (136.4)[2] |
| Cl/F (mL/min) | 9.518 (28.4)[2] | 9.334 (18.9) | 10.246 (56.9) |
| $V_z$/F (L) | 376 (19.3)[2] | 363 (30.5) | 405 (43.9)[2] |

$AUC_{24}$ = area under the plasma concentration-time curve from time of dosing to 24 hours after dosing, $AUC_{inf}$ = area under the plasma concentration-time curve from time of dosing to infinity, $AUC_{last}$ = area under the plasma concentration-time curve from time of dosing to the last measurable concentration, $C_{max}$ = maximum (peak) plasma drug concentration, CL/F = apparent total clearance of the drug from plasma after oral administration, CV % = percent coefficient of variation, % $AUC_{extrap}$ = area under the plasma concentration-time curve extrapolated from time t to infinity as a percentage of the total area under the curve, MR = modified-release, t½ = elimination half-life, $t_{lag}$= lag time, $t_{max}$ = time of maximum (peak) plasma drug concentration, $V_z$/F = apparent volume of distribution during terminal phase after oral administration.

[1]Median (range).

[2]n = 5.

Pharmacokinetic properties of multiple 20 and 40 mg doses of the 20 mg tablet (formulation 3) were determined on day 1 and 8 of dosing, as shown below in Table 12. Based on the results of this trial, following once daily dosing with the 20 mg tablet formulation for 8 days, exposure to the compound of formula (II) increased with dose over the dose range of 20 to 40 mg. Variability in $C_{max}$ and AUC increased somewhat within the dose range studied. Steady state was achieved by day 5 of repeated daily dosing over the dose range 20 to 40 mg. An approximately 2-fold increase in $C_{max}$ was observed over the 8 days of dosing.

TABLE 12

Geometric Mean Values (Geometric CV %) of Plasma Pharmacokinetic Parameters After Single and Multiple Oral Doses of 20 mg Tablet Formulation (formulation 3) (Part B)

| | Dose group: 20 mg [20 mg Tablet × 1 (formulation 3)] (N = 6) | | 40 mg [20 mg Tablet × 2 (formulation 3)] (N = 6) | |
|---|---|---|---|---|
| Parameter | Day 1 | Day 8 | Day 1 | Day 8 |
| $t_{lag}$ (h)[1] | 0.250 (0.25-0.25) | 0.00 (0.00-0.00) | 0.250 (0.25-0.50) | 0.00 (0.00-0.00) |
| $t_{max}$ (h)[1] | 14.000 (5.00-23.92) | 1.500 (1.25-3.00) | 2.750 (1.50-12.00) | 1.750 (1.50-5.00) |
| $C_{max}$ (ng/mL) | 38.5 (22.6) | 66.5 (25.2) | 70.3 (37.9) | 138 (47.1) |
| $C_{min, ss}$ (ng/mL) | NA | 34.6 (27.6) | NA | 55.3 (49.0) |
| $C_{avg, ss}$ (ng/mL) | NA | 46.8 (27.2) | NA | 86.1 (46.4) |
| $AUC_{\tau, ss}$ (ng · h/mL)[2] | 689 (27.2) | 1120 (27.2) | 1050 (44.0) | 2070 (46.4) |
| $t_{1/2, ss}$ (h) | NC | 10.545 (16.5) | NA | 9.956 (14.4) |
| Cl/$F_{,ss}$ (mL/min) | NA | 297 (27.2) | NA | 322 (46.4) |
| $V_z$/$F_{,ss}$ (L) | NA | 271 (21.3) | NA | 278 (33.2) |
| Fluctuation (%) | NA | 67.369 (15.4) | NA | 94.771 (21.1) |
| Rac AUC | NA | 1.631 (25.0) | NA | 1.961 (22.4) |
| Rac $C_{max}$ | NA | 1.729 (20.1) | NA | 1.967 (22.6) |

Abbreviations: $AUC_{24}$ = area under the plasma concentration-time curve from time of dosing to 24 hours after dosing, $AUC_\tau$ = area under the plasma concentration-time curve during a dosing interval, $C_{avg}$ = average drug concentration during multiple dose administration, $C_{max}$ = maximum (peak) plasma drug concentration, $C_{min}$ = minimum plasma drug concentration, CL/F = apparent total clearance of the drug from plasma after oral administration, CV % = percent coefficient of variation, MR = modified-release, NA = not applicable, NC = not calculated, Rac AUC = accumulation ratio calculated from $AUC_{\tau, ss}$ and $AUC_\tau$ , Rac $C_{max}$ = accumulation ratio calculated from $C_{max, ss}$, ss = steady state, t½ = elimination half-life, $t_{lag}$ = lag time, $t_{max}$ = time of maximum (peak) plasma drag concentration, $V_z$/F = apparent volume of distribution during terminal phase after oral administration.

[1]Median (range).

[2]Labeled as $AUC_{24}$ on day 1

Example 6: Modified Release Tablet Formulations 4 and 5 of the Compound of Formula (I)

Formulations 4 and 5 supplied as coated matrix modified release (MR) tablets are each designed to release approximately 80% of the drug substance within 7 hours. The compositions for the clinical batches of the product (formulations 4 and 5) are shown in Table 13. Each active tablet will contain the drug substance equivalent to 5 or 20 mg of the compound of formula (I), corresponding to about 5.475 mg or 21.90 mg of the compound of formula (II), respectively.

TABLE 13

Formulation of the compound of formula (I) for modified release tablets containing 5 mg or 20 mg of the compound of formula (I)

| Ingredients | formulation 4 | formulation 5 |
|---|---|---|
| the compound of formula (II) (HCl salt, form C)[a] | 5.5 mg | 21.9 mg |
| Hypromellose | 58.0 mg | 58.0 mg |
| Microcrystalline cellulose[b] | 34.0 mg | 17.6 mg |
| Colloidal silicon dioxide | 1.5 mg | 1.5 mg |
| Magnesium stearate | 1.0 mg | 1.0 mg |
| Opadry white 03K580000 | 3.0 mg | 3.0 mg |
| Total weight | 103 mg | 103 mg |

[a]Quantity of formula (I) is adjusted for free base

[b]Quantity of Microcrystalline Cellulose (Avicel PH101) compensated accordingly for quantity of formula (I)

The dissolution method used to assess release is a chromatographic detection method using USP apparatus type-I. The dissolution parameters and high performance liquid chromatography (HPLC) conditions for assessing the release are shown below.

TABLE 14

| Dissolution Parameters | |
|---|---|
| Dissolution media | 0.1N Hydrochloric acid |
| Media Volume | 900 mL |
| Rotation Speed | 100 RPM |
| Media Temperature | 37° C. ± 0.5° C. |
| Dissolution apparatus | USP type-I (Basket) |
| Sampling Volume | 10 mL |
| Replenishing Volume | 10 mL |

TABLE 14-continued

| Dissolution Parameters | |
|---|---|
| Sampling | Manual, with 10 μm full flow PVDF in-line filter or Auto sampler with 10 μm full flow PVDF in-line filter followed by 0.45 μm nylon filter |

TABLE 15

| Chromatographic conditions | |
|---|---|
| Column | Waters X-Bridge C18 (150 × 4.6 mm; 5 μm) |
| Mobile Phase-A | 25 mM potassium dihydrogen phosphate pH 3.0 |
| Mobile phase-B | Acetonitrile |
| Column temperature | 35° C. |
| Auto sampler temperature | Ambient |
| Injection volume | 50 μL |
| Flow rate | 1.5 mL/min |
| Detection | 230 nm |
| Diluent | Use dissolution media as diluent. |
| Run time | 8 minutes |
| Needle wash | Water:Methanol (20:80% v/v) |

TABLE 16

Gradient Program

| Time (Minutes) | Mobile Phase-A % | Mobile Phase-B % |
|---|---|---|
| 0.00 | 67 | 33 |
| 1.50 | 67 | 33 |
| 4.00 | 55 | 45 |
| 4.10 | 67 | 33 |
| 8.00 | 67 | 33 |

Manufacturing Process

The modified release tablets are manufactured by sifting and blending of the excipients, including lubricant. The blend is granulated by roller compaction and milling of the ribbon compact. The granules are lubricated and then compressed into tablets. The tablets are then film coated.

A number of quality attributes are monitored in process, during release testing and on stability. These include hardness, friability, appearance, assay, related substances, content uniformity, water content and dissolution.

Additional modified release formulations (formulations 6-9) are provided in Table 17.

TABLE 17

Formulation of the compound of formula (I) for modified release tablets containing 10, 15, 30, and 40 mg of the compound of formula (I)

| Ingredients | formulation 6 | formulation 7 | Formulation 8 | Formulation 9 |
|---|---|---|---|---|
| the compound of formula (II) (HCl salt, form C)[a] | 11.0 mg | 16.4 mg | 32.9 mg | 43.8 mg |
| Hypromellose | 58.0 mg | 58.0 mg | 87.0 mg | 116.0 mg |
| Microcrystalline cellulose[b] | 28.6 mg | 23.1 mg | 26.4 mg | 35.2 mg |
| Colloidal silicon dioxide | 1.5 mg | 1.5 mg | 2.3 mg | 3.0 mg |

TABLE 17-continued

Formulation of the compound of formula (I) for modified release tablets containing 10, 15, 30, and 40 mg of the compound of formula (I)

| Ingredients | formulation 6 | formulation 7 | Formulation 8 | Formulation 9 |
|---|---|---|---|---|
| Magnesium stearate | 1.0 mg | 1.0 mg | 1.5 mg | 2.0 mg |
| Opadry white 03K580000 | 3.0 mg | 3.0 mg | 4.5 mg | 6.0 mg |
| Total weight | 103 mg | 103 mg | 155 mg | 206 mg |

[a]Quantity of formula (I) is adjusted for free base

[b]Quantity of Microcrystalline Cellulose (Avicel PH101) compensated accordingly for quantity of formula (I)

Figure 11:
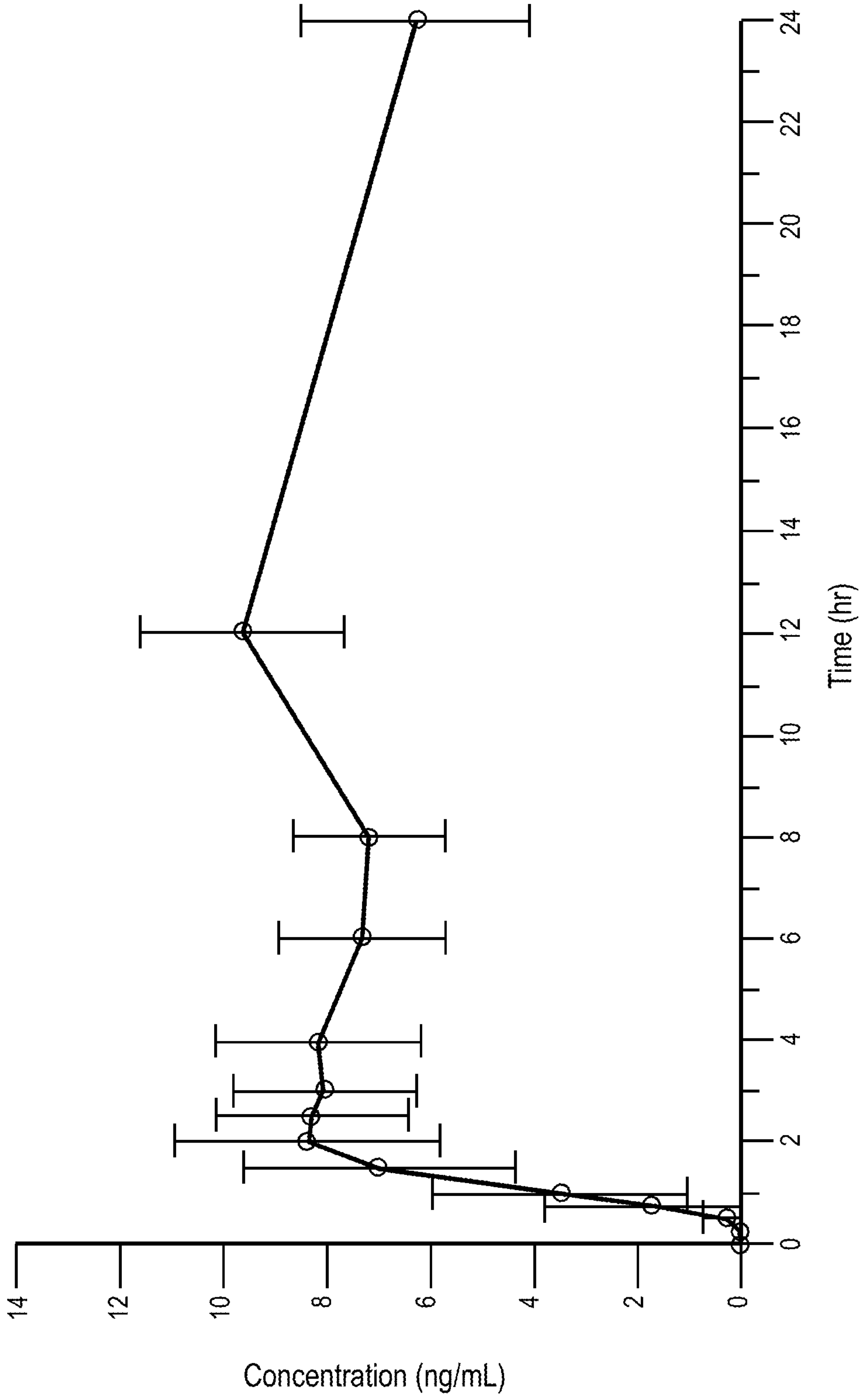
FIG. 11 shows mean (±SD) concentrations after a single oral doses of 5 mg tablet formulation 4.

After administration of a single 5 mg dose of the compound of formula (II) (formulation 4) to healthy volunteers, plasma concentrations of the free base of the compound of formula (I) (i.e., the compound of formula (II)) were quantifiable by 0.50 hours after administration of the modified release tablet formulation of the compound of formula (II). Plasma concentrations plateaued after reaching $C_{max}$ and then declined by 24 hours after administration of formulation 4. The compound of formula (I) as free base (i.e., a compound of formula (II)) remained quantifiable for the duration of the 24 hour sampling period after administration of a 5 mg dose of formulation 4. FIG. 11 shows mean (±SD) concentrations after a single oral dose of 5 mg tablet formulation 4.

TABLE 18

Geometric Mean Values (Geometric CV %) After a Single Oral Doses of 5 mg Tablet Formulation 4

| Parameter | 5 mg [5 mg formulation 4 Tablet × 1] (N = 8) |
|---|---|
| $t_{lag}$ (h)[1] | 0.500 (0.25-0.75) |
| $t_{max}$ (h)[1] | 12.00 (2.0-12.0) |
| $C_{max}$ (ng/mL) | 9.90 (23.3) |
| $AUC_{24}$ (ng*h/mL) | 179 (22.2) |

$AUC_{24}$ = area under the plasma concentration-time curve from time of dosing to 24 hours after dosing, $C_{max}$ = maximum (peak) plasma drug concentration, CV % = percent coefficient of variation, MR = modified-release, $t_{lag}$ = lag time, $t_{max}$ = time of maximum (peak) plasma drug concentration.

[1]Median (range).

Example 7: Long-Term Stability of the Compound of Formula (II) (Form C) in the Formulation The drug product is chemically and physically stable for up to 48 months at 25° C./60% RH (Table 19) or for up to 6 months under accelerated conditions (40° C./75% RH) (Table 20). Based upon the currently available stability data, a shelf-life of 60 months has been assigned for the 20 mg drug product (formulation 3) packaged in 40 cc high-density polyethylene (HDPE) bottles when stored between 20° C. and 25° C. as per United States Pharmacopeia (USP) definition of controlled room temperature. Based on the excellent stability of the 20 mg drug product for at least 48 months and the essential identical composition of the 5 mg drug product, a shelf-life of 24 months has been assigned for the 5 mg drug product (formulation 4) packaged in 40 cc high-density polyethylene (HDPE) bottles when stored between 20° C. and 25° C.

Stability studies of MR tablets comprising the compound of formula II (containing Form C) were performed at 25° C./60% RH. Batch size was 10,000 tablets. Each film coated tablet contained 20 mg of the compound of formula II. The tablets were packaged in 40 cc HDPE bottles containing 30 tablets with CRC cap (Table 19).

TABLE 19

Stability study data for MR tablets formulation 3 (containing 20 mg of the compound of formula (II)) at 25° C./60% over 48 months

| | Test | Specification | Initial | 1 M | 3 M | 6 M |
|---|---|---|---|---|---|---|
| 1 | Appearance | White to off white round shaped film coated tablets. | Complies | Complies | Complies | Complies |
| 2 | Assay by HPLC | 90.0-110.0% | 100.6% | 100.4% | 102.7% | 101.8% |
| | Related substances by HPLC (% w/w) | | | | | |
| 3 | Total impurities | NMT 1.5% | 0.38% | 0.37% | 0.40% | 0.38% |
| 4 | Water by KF | To be reported | 4.7% | 4.8% | 5.5% | 5.7% |
| | Test | Specification | 9 M | 12 M | 18 M | 24 M |
| 1 | Appearance | White to off white round shaped film coated tablets. | Complies | Complies | Complies | Complies |
| 2 | Assay by HPLC | 90.0-110.0% | 99.6% | 100.7% | 101.7% | 99.6% |

TABLE 19-continued

Stability study data for MR tablets formulation 3 (containing 20 mg of the compound of formula (II)) at 25° C./60% over 48 months

| | | | | | | |
|---|---|---|---|---|---|---|
| | Related substances by HPLC (% w/w) | | | | | |
| 3 | Total impurities | NMT 1.5% | 0.40% | 0.40% | 0.41% | 0.45% |
| 4 | Water by KF | To be reported | 4.8% | 5.0% | 4.6% | 4.7% |

| | Test | Specification | 36 M | 48 M |
|---|---|---|---|---|
| 1 | Appearance | White to off white round shaped film coated tablets. | Complies | Complies |
| 2 | Assay by HPLC | 90.0-110.0% | 99.5% | 100.4% |
| | | Related substances by HPLC (% w/w) | | |
| 3 | Total impurities | NMT 1.5% | 0.42% | 0.72% |
| 4 | Water by KF | To be reported | 4.9% | 5.0% |

NMT—not more than;
RH—relative humidity

Stability studies of MR tablets comprising the compound of formula II (containing Form C) were performed at 40° C./75% RH. Batch size was 10,000 tablets. Each film coated tablet contained 20 mg of the compound of formula II. The tablets were packaged in 40 cc HDPE bottles containing 30 tablets with CRC cap (Table 20).

TABLE 20

Stability study data for MR tablets formulation 3 (containing 20 mg of the compound of formula (II)) in accelerated conditions

| | Test | Specification | Initial | 1 M | 3 M | 6 M |
|---|---|---|---|---|---|---|
| 1 | Appearance | White to off white round shaped film coated tablets. | Complies | Complies | Complies | Complies |
| 2 | Assay by HPLC | 90.0-110.0% | 100.6% | 99.5% | 100.2% | 101.0% |
| | | Related substances by HPLC (% w/w) | | | | |
| 3 | Total impurities | NMT 1.5% | 0.38% | 0.37% | 0.41% | 0.40% |
| 4 | Water by KF | To be reported | 4.7% | 5.2% | 4.9% | 5.3% |

NMT—not more than;
RH—relative humidity

Stability studies of tablets of formulation 4 comprising 5 mg of the compound of formula (II) (containing Form C) were performed at 25° C./60% RH. Batch size was 30,000 tablets. The tablets were packaged in 40 cc HDPE bottles containing 30 tablets with CRC cap (Table 21).

TABLE 21

Stability study data for tablets (formulation 4) at 25° C./60% RH over 3 months

| | Test | Specification | Initial | 1 M | 3 M |
|---|---|---|---|---|---|
| 1 | Appearance | White to off-white, round biconcave film-coated tablets, no embossing. | White, round biconcave film-coated tablets, no embossing | White, round biconcave film-coated tablets, no embossing. | White, round biconcave film-coated tablets, no embossing. |
| 2 | Assay by HPLC | 90.0% to 110.0% of label claim | 97.9% | 98.9% | 96.1% |
| 3 | | Related substances by HPLC (% w/w) | | | |
| | Total impurities | Not more than 2.0% | 0.16% | 0.14% | 0.14% |
| 4 | Water content USP<921> | To be reported | 4.3% | 4.4% | 4.4% |

Example 8: Assessment of the Safety, Tolerability, Pharmacokinetics, and Efficacy of Escalating Multiple Oral Doses in Adults with Generalized Epileptic Syndromes with Absence Seizures This open-label, multiple ascending dose trial will principally assess the safety and tolerability of 20 mg daily and 40 mg daily (20 mg twice daily) doses of the 20 mg modified release tablet (formulation 3), adjunctive to standard of care. Secondary objectives include characterizing the pharmacokinetic, pharmacodynamic (sigma frequency power during NREM sleep), and effects on seizure frequency of the tablet (formulation 3).

Subjects

Subjects of this study are male or female between the ages of 18 and 60 years of age. Subjects have a clinical diagnosis of an epileptic syndrome (including, but not limited to, childhood absence seizures, juvenile absence seizures, juvenile myoclonic epilepsy, or Jeavons syndrome) with absence seizures consistent with the International League against Epilepsy Revised Classification of Seizures (2017), have absence seizures persisting despite documented trials with at least one standard anti-epileptic treatment, and have a history and electrographic evidence of absence epilepsy.

Methodology:

Each participant will complete 3 study periods: Screening, Treatment Period (up to 2 dose levels followed by a taper), and Safety Follow-up. All participants will undergo two weeks of dosing of the compound of formula (II), followed by a taper, as follows:

- Dose Level 1: 20 mg (formulation 3) every day for 7 days, and up to 14 days if 20 mg twice a day is not tolerated.
- Dose Level 2: 20 mg (formulation 3) twice a day for 7 days.
- Taper: If the participant tolerates the full 7 days of 20 mg twice a day, the taper will be 20 mg daily for 2 days (Day 15 and 16) followed by 20 mg every other day for 5 days (Day 17, 19, and 21). If the participant only tolerates 20 mg daily, the taper will be 20 mg every other day for 7 days (Day 15 to Day 21).

Safety and Tolerability

Safety variables include clinical laboratory evaluations, physical examination, vital signs, 12-lead ECG, the C-SSRS, and adverse event (AE) assessments, including event type, frequency, seriousness, severity, timing, and relationship to IP.

Pharmacokinetics

Pharmacokinetic parameters will include: maximum observed concentration ($C_{max}$), and at steady-state ($C_{max,SS}$), Time of $C_{max}$ ($T_{max}$) and $C_{max,SS}$ ($T_{max,SS}$), area under the concentration-time curve through the dosing interval ($AUC_{tau}$ or $AUC_{SS}$), total clearance at steady-state (CLSS). Additional parameters such as half-life, accumulation and volume of distribution at steady-state (VSS) will be calculated if feasible.

Efficacy

Efficacy is evaluated by a) Number of seizures by participant reported seizure diary including absence seizures, generalized tonic-clonic seizures, and myoclonic seizures, b) EEG measures of seizure activity and pharmacodynamic effects of the compound of formula (I) including: Seizure Density (Number of bilateral synchronous symmetrical spike waves discharges of approximately 2.5-5 Hz>3 seconds in an approximately 24 hour period inclusive of seizures induced with photic stimulation and hyperventilation), Mean Seizure Duration (Average duration of 2.5-5 Hz discharges that are greater than 3 seconds in duration in a 24 hour period), Cumulative Seizure Duration (Product of Seizure Density and Mean Seizure Duration), Total time with 2.5-4 Hz spike wave discharges after hyperventilation and photic stimulation challenges, and c) Global severity as measured by CGI-S and CGI-I scores.

Example 9: Evaluation of Efficacy, Safety, Tolerability and Pharmacokinetics of the Compound of Formula (I) or a Pharmaceutically Acceptable Salt Thereof in Essential Tremor A randomised controlled trial is conducted to study the efficacy, safety, and tolerability of the compound of formula (I) in essential tremor. Each patient completes 3 study periods: Screening, Treatment period (21 or 28 days), and Safety follow-up.

Patients are males and females between the ages of 18 and 75 years old and have been diagnosed with essential tremor for at least 3 years. Patients receive a stable dose of 1 tremor medication throughout the clinical trial. Patients who had clinical evidence of psychogenic tremor, history of other medical, neurological or psychiatric condition that may explain or cause tremor, prior magnetic resonance-guided focused ultrasound or surgical intervention for essential tremor, botulinum toxin injection for essential tremor in the 6 months prior to Screening are excluded from the studies.

Patients receive 20 mg of the compound of formula (I) (formulation 3) orally once a day for 14 days and twice a day for 7 days (Part A) or 20 mg of the compound of formula (I) (formulation 3) orally once a day for 14 days and twice a day for 14 days or placebo (Part B).

Efficacy of the compound of formula (I) on upper limb tremor is assessed by the TETRAS upper limb score at Baseline, on Day 21 (Part A) and Day 28 (Part B).

Efficacy of the compound of formula (I) on other measures of tremor severity is assessed by TETRAS performance subscale score and TETRAS performance individual items at Baseline, on Day 21 (Part A), and Day 28 (Part B).

Safety and tolerability of the compound of formula (I) is assessed through an integrated analysis of the following endpoints: patient and clinician-reported adverse events, vital signs, clinical laboratory results, electrocardiogram (ECG), and Columbia-Suicide Severity Rating Scale (C-SSRS) at Baseline, on Day 1, Day 7, Day 14, Day 21, and Day 28 (Part B only).

Example 10: Evaluation of Efficacy, Safety, Tolerability and Pharmacokinetics of the Compound of Formula (I) in Essential Tremor A non-randomised, uncontrolled, and open-label trial was conducted to study the efficacy, safety, tolerability, and pharmacokinetics of the compound of formula (I) in adults with essential tremor. Patients were males and females between the ages of 18 and 75 years old and have been diagnosed with essential tremor (e.g., as defined by the Movement Disorders Society, or MDS, Task Force for Tremor as an isolated tremor syndrome of bilateral UL action tremor with at least 3 years' duration). Patients were required to have a combined bilateral score of >10 on the TETRAS UL items as confirmed by site investigator and central video review.

Each patient completed 3 study periods: Screening, Treatment period (14 days), and Safety follow-up. A video of the TETRAS Performance subscale was completed during Screening. It was acceptable for the patient to receive a stable dose of 1 previously prescribed tremor medication throughout the clinical trial.

Patients who had clinical evidence of psychogenic tremor, history of other medical, neurological or psychiatric condition that may explain or cause tremor, prior magnetic resonance-guided focused ultrasound or surgical intervention for essential tremor, botulinum toxin injection for essential tremor in the 6 months prior to Screening are excluded from the studies.

Each patient received 20 mg of the compound of formula (I) (one tablet of formulation 5) orally once a day in the morning (QAM) for 7 days and 40 mg of the compound of formula (I) (two tablets of 20 mg formulation 5) orally once a day in the morning (QAM) for 7 days (total of 14 days consecutively).

Primary efficacy endpoint of the compound of formula (I) was upper limb tremor as assessed by The Essential Tremor Rating Assessment Scale (TETRAS) upper limb item score (Item #4) at Baseline, on Day 7, and on Day 14.

Efficacy of the compound of formula (I) on other measures of tremor severity was assessed by TETRAS performance subscale score, TETRAS performance individual items, and accelerometer at Baseline, on Day 7, and on Day 14.

Efficacy of the compound of formula (I) was also assessed by Clinical Global Impression-Severity (CGI-S), Clinical Global Impression-Improvement (CGI-I), and Patient Global Impression of Change (PGI-C).

Safety and tolerability of the compound of formula (I) were assessed through an integrated analysis of the following endpoints: patient and clinician-reported adverse events (e.g., dizziness or headache), vital signs, clinical laboratory results, electrocardiogram (ECG), and Columbia-Suicide Severity Rating Scale (C-SSRS) at Baseline, on Day 1, Day 7, Day 14, and Day 21. Six participants have completed this study. Preliminary site data from the 6 patients showed stable tremor severity between screening and baseline visits. In addition, tremor reduction was observed for both dose levels which seems to compare favorably to the standard of care agents.

Mean upper limb tremor score on the TETRAS Item 4 was reduced as compared to baseline after administration of 20 mg (formulation 5) for 7 days (Day 7) and further reduction was seen after administering 40 mg (two tablets of 20 mg formulation 5) for an additional 7 days (Day 14). The mean baseline TETRAS-UL score was 12.4 (with a range of 10 to 15, corresponding to moderate disease). At Day 14, the upper limb tremor score was reduced by at least 25% as compared to the baseline. For example, over the 14 days of dosing, a mean reduction of 2.83 points was observed on the TETRAS upper limb score, which corresponds to about a 40% (e.g., 42%) mean reduction in tremor amplitude. Three participants had greater than or equal to a 4-point reduction in the primary endpoint for the study, TETRAS-UL score, which corresponds to a greater than 50% reduction in upper limb tremor amplitude. Notably, after 7 days of washout, the upper limb score increased as compared to that of Day 14 above, suggesting a gradual return to baseline dysfunction.

Mean TETRAS performance score was reduced as compared to baseline after administration of 20 mg (formulation 5) for 7 days (Day 7) and further reduction was seen after administering 40 mg (two tablets of 20 mg formulation 5) for an additional 7 days (Day 14), with a mean reduction at Day 14 of 6.25 points. At Day 14, the TETRAS performance score was reduced by at least 25% as compared to the baseline. Based on the six participants who completed the study, improvement was observed in the full TETRAS-PS, with at least 35% (e.g., 36%) average reduction in symptom severity from baseline to Day 14. Notably, after 7 days of washout, the performance score increased as compared to that of Day 14 above, suggesting a gradual return to baseline dysfunction. Based on the six participants who completed the study, TETRAS upper limb score correlated with TETRAS performance score.

Figure 6:
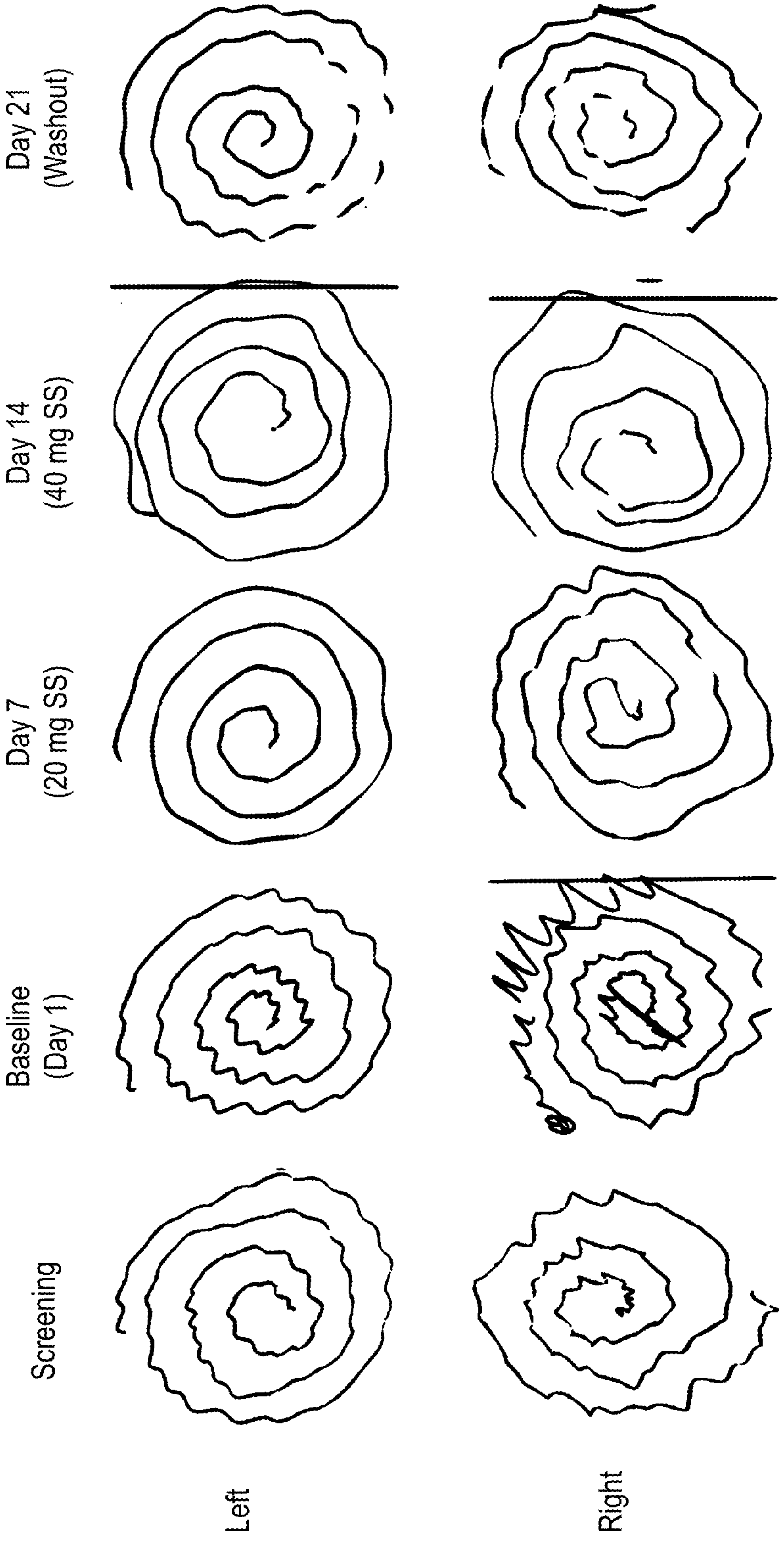
FIG. 6 shows the reduction in tremor in the Archimedes spiral task with administration of the compound of formula (II).

FIG. 6 demonstrates the reduction in tremor in one participant on the Archimedes spiral task with administration of the compound of formula (I) (formulation 5). The Archimedes spiral task is used in the art to identify essential tremor in patients, as described, for example, in Michalec, M et al., "The Spiral Axis as a Clinical Tool to Distinguish Essential Tremor from Dystonia Cases," *Parkinsonism Relat. Disord.* 2014; 20(5):541-544. As shown in FIG. 6, the patient demonstrated a visible reduction in essential tremor between, for example, the Baseline (Day 1) spirals and the Day 7 and Day 14 spirals.

Figure 15:
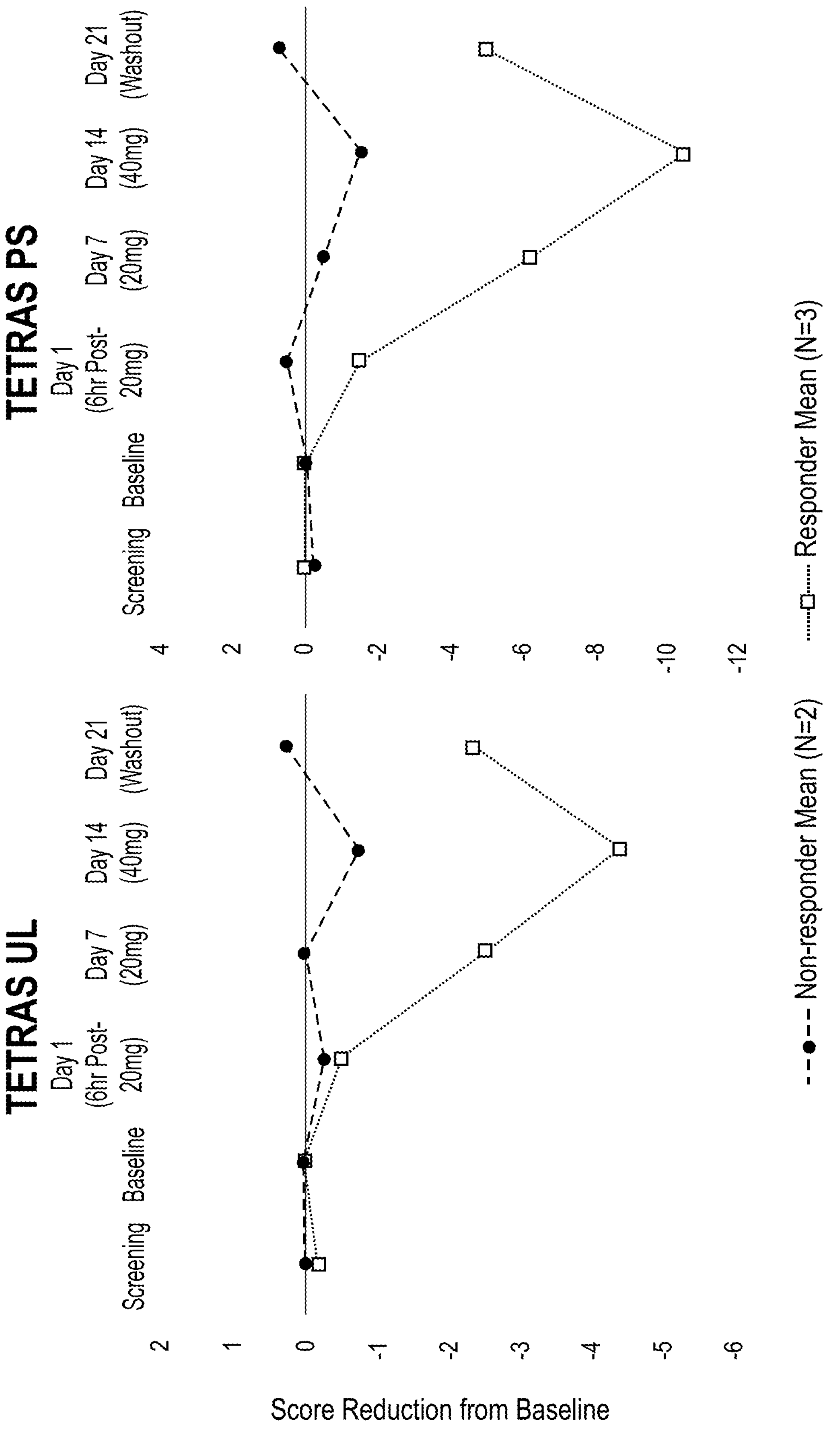
FIG. 15 shows preliminary site data (TETRAS UL and TETRAS PS) from the essential tremor open-label study.

FIG. 15 shows the TETRAS UL and TETRAS PS, data for the five patients who have completed the study. As shown in FIG. 15, both the mean TETRAS UL and the mean TETRAS PS scores reduced between the Baseline score and the scores at Day 7 and Day 14.

Compound of formula (I) (formulation 5) has been safe and well tolerated. There were no SAEs and no severe AEs. The majority of AEs were mild, transient, and resolved without intervention. All five participants that were enrolled completed the full dosing schedule. There were no clinically significant ECG or laboratory abnormalities. There were no changes in the C-SSRS.

The emerging data suggests that the compound of formula (I) is well tolerated and can reduce upper limb tremor amplitude and improve activities of daily living (ADLs), such as writing skills. Physician rating scales, an accelerometer based tremor assessment tool, and patient symptom rating scales have all consistently demonstrated a reduction in symptoms with administration of the compound of formula (I) (formulation 5). In addition, participant anecdotes suggest that once lost abilities, like carrying a tray with food or drinks, can be regained after taking the compound of formula (I) (formulation 5).

Example 11: Evaluation of Safety, Tolerability, Pharmacokinetics and Pharmacodynamics of the Compound of Formula (I) in a within-Participant Escalating Dose Paradigm A trial was conducted to study the safety, tolerability, pharmacokinetics and pharmacodynamics of the compound of formula (I) in healthy participants. Each participant completed 3 study periods: Screening, Treatment period (12 or 31 days), and Safety follow-up.

Participants were healthy males and females between the ages of 18 and 55 years old. Participants who have ongoing or history of any psychiatric, medical or surgical condition that might jeopardize the participant's safety or interfere with the absorption, distribution, metabolism or excretion of the study drug were excluded from the studies.

In Part A, an open label trial was conducted. Patients received 5 mg of the compound of formula (I) (formulation 4) daily for 4 days (Day 1 to Day 4), followed by 10 mg (2×5 mg formulation 4) daily for 4 days (Day 5 to Day 8) and 20 mg (formulation 5) daily for 4 days (Day 9 to Day 12).

In Part B, a randomized controlled trial was conducted. Patients received 20 mg of the compound of formula (I) (formulation 5) or matching placebo daily for 3 days (Day 1 to Day 3), 40 mg daily for 3 days (Day 4 to Day 6), 60 mg daily for 7 days (Day 7 to Day 13), 80 mg daily for 7 days (Day 14 to Day 20), 100 mg daily for 7 days (Day 21 to Day 27), and 120 mg daily for 4 days (Day 28 to Day 31). Patients were allowed to receive the compound of formula (I) daily at each of 60 mg, 80 mg, and 100 mg dose levels for an extended period of up to 2 days.

Activities performed in Part A during the trial are outlined in Table 22.

In Part A, pharmacodynamic effects of the compound of formula (I) as assessed by the changes in quantitative electroencephalography (qEEG) were evaluated at Baseline on Day 1, Day 4, Day 5, Day 8, Day 9, Day 12, and Day 13.

In Part A, pharmacokinetics of the compound of formula (I) was evaluated by performing liquid chromatography/mass spectrometry (LC/MS) quantification of levels of the compound in plasma. Blood samples for pharmacokinetic analysis were collected at pre-determined time points: D1, D5, and D9: pre-dose (within 60 mins prior to dosing) and 0.25, 0.5, 0.75, 1, 1.5, 2, 2.5, 3, 4, 6, 8, 12 hours post-dose; D2 to D4, D6 to D8, and D10 to D12: pre-dose (within 60 mins prior to dosing); and D13: prior to discharge (at approximately the same time the pre-dose samples were collected). Sample collection windows were as follows: ±2 mins for <1 hour post-dose; ±5 mins for 1 to 3-hours post-dose; ±10 mins for 4 to 12-hours post-dose.

Phamacokinetic parameters determined for the compound of formula (I) include, but are not limited to, the area under the plasma concentration-time curve ($AUC_t$), $AUC_{inf}$, $AUC_{tau}$, maximum (peak) plasma drug concentration ($C_{max}$), time to reach maximum (peak) plasma drug concentration ($t_{max}$), terminal elimination half-life ($t_{1/2}$), apparent plasma clearance after oral administration (Cl/F), and apparent volume of distribution based on terminal phase (Vd/F).

In Part A, safety and tolerability of the compound of formula (I) as assessed through an integrated analysis of the following endpoints: patient and clinician-reported adverse events, physical exams, vital signs, clinical laboratory results, electrocardiogram (ECG), electroencephalogram (EEG) and Columbia-Suicide Severity Rating Scale (C-SSRS), were evaluated at Baseline and at multiple times between Day 1 to Day 13, as shown below in Table 22. Patients were discharged on D13 after all study assessments were completed and scheduled for Safety Follow-up on Day 17 (±1 day) via telephone call.

TABLE 22

Schedule of Activities for Part A

| | Trial Period | | | | | | | | | | | | | | | |
|---|---|---|---|---|---|---|---|---|---|---|---|---|---|---|---|---|
| | Screening | Intervention Visit Day | | | | | | | | | | | | | | Safety Follow-up |
| | D −28 to D −2 | Baseline/ D −1 | D 1 | D 2 | D 3 | D 4 | D 5 | D 6 | D 7 | D 8 | D 9 | D 10 | D 11 | D 12 | D 13 | D 17 (±1 d) or End of Trial |
| TRIAL ENTRY AND GENERAL ASSESSMENTS | | | | | | | | | | | | | | | | |
| Informed Consent | X | | | | | | | | | | | | | | | |
| Inc/Exc Criteria | X | X | | | | | | | | | | | | | | |
| Medical History | X | | | | | | | | | | | | | | | |
| Demographic Data | X | | | | | | | | | | | | | | | |
| Body Weight/ Height/BMI | X | | | | | | | | | | | | | | | |
| Drug/ Alcohol/ Nicotine Screen | X | X | | | | | | | | | | | | | | |
| Viral Serology Screen [a] | X | | | | | | | | | | | | | | | |
| Inpatient Stay/ Telephone Call | | A | X | X | X | X | X | X | X | X | X | X | X | X | D | TC |
| SAFETY ASSESSMENTS | | | | | | | | | | | | | | | | |
| Physical Examination | X | X | | | | X | | | | X | | | | | X [b] | |
| Clinical Laboratory Evaluations [c] | X | X | | | | | | X | | | | | | | X | |
| Pregnancy Test [d] | X | X | | | | | | | | | | | | | X | |
| Exploratory Urine Biomarkers [e] | | | X | | | | | | | | | | | | X | |
| Vital Signs [f] | X | X | X | X | X | X | X | X | X | X | X | X | X | X | X | |
| 12-lead ECG [g] | X | X | | | | X | | | | X | | | | | X | |
| C-SSRS (Baseline/ Screening) | X | | | | | | | | | | | | | | | |
| C-SSRS (Since Last Visit) [h] | | X | | | | | X | | | | X | | | | X | |
| AE Monitoring and Recording [i] | | | | | | | | X | | | | | | | | |
| Concomitant Meds/Procedures [i] | | | | | | | | X | | | | | | | | |

TABLE 22-continued

Schedule of Activities for Part A

| | Trial Period | | | | | | | | | | | | | | |
|---|---|---|---|---|---|---|---|---|---|---|---|---|---|---|---|
| | Screening | Intervention Visit Day | | | | | | | | | | | | | Safety Follow-up |
| | D −28 to D −2 | Baseline/ D −1 | D 1 | D 2 | D 3 | D 4 | D 5 | D 6 | D 7 | D 8 | D 9 | D 10 | D 11 | D 12 | D 13 | D 17 (±1 d) or End of Trial |
| PHARMACOKINETICS | | | | | | | | | | | | | | | | |
| Blood Collection for Study Drug Concentration | | | X | X | X | X | X | X | X | X | X | X | X | X | X | |
| PHARMACODYNAMICS | | | | | | | | | | | | | | | | |
| EEG including PSG[k] | | X | | | | X | | | | X | | | | X | | |
| qEEG | | X | | | | X | X | | | X | X | | | X | X | |
| STUDY DRUG | | | | | | | | | | | | | | | | |
| Study Drug Administration[m] | | | X | X | X | X | X | X | X | X | X | X | X | X | | |

A = admission; AE = adverse event; BMI = body mass index; C-SSRS = Columbia-Suicide Severity Rating Scale; D = discharge; ECG = electrocardiogram; EEG = electroencephalogram; PSG = polysomnogram; qEEG = quantitative electroencephalogram; TC = telephone call.

[a] Hepatitis B, C, and HIV.

[b] Symptom-directed physical examination.

[c] CBC, clinical chemistry, coagulation (Screening only), urinalysis, and urine albumin. Collected pre-dose on dosing days.

[d] If applicable, serum hCG at Screening and urine hCG at D −1 and D 13.

[e] Urine creatinine and KIM-1. Collected pre-dose on D 1.

[f] Including oral temperature, respiratory rate, supine blood pressure, and pulse rate will be obtained as follows: Screening; D −1; D 1, D 5 and D 9: pre-dose (within 60 mins prior to dosing) and 0.25, 1, 2, 3, and 4 hrs post-dose (±15 mins); D 2 through D 4, D 6 through D 8, and D 10 through D 12: 2 hours post-dose (±15 mins); D 13: prior to discharge.

[g] Triplicate measurements at Screening only. Baseline: anytime; During the intervention period: 2 hours after dosing (±15 mins).

[h] During the intervention period C-SSRS to be conducted pre-dose.

[i] Throughout the trial from time of signing informed consent until end of trial.

[k] 24-hour EEGs including PSG. D −1 (Baseline): after confirmation of eligibility until 1 hour prior to dosing on D 1; D 4 and D 8: 2 hours prior to dosing until 2 hours prior to dosing on the following day; D 12: 2 hours prior to dosing until approximately 22 hours after dosing.

Note:

If vital signs assessments are scheduled at the same nominal timepoint as other assessments, the following order are followed: PK sample, vital signs, ECG, and qEEG, and the vital signs assessments are obtained as close to the scheduled timepoint as possible.

Activities performed in Part B during the trial are outlined in Table 23.

In Part B, safety and tolerability of the compound of formula (I) as assessed through an integrated analysis of the following endpoints: patient and clinician-reported adverse events, physical exams, vital signs, clinical laboratory results, ECG, EEG and C-SSRS, were evaluated at Baseline and on Day 1 to Day 33 at pre-determined time points, as shown below in Table 23. Patients were discharged on D33 after all study assessments were completed and scheduled for Safety Follow-up on Day 36 (±1 day) via telephone call. Pharmacokinetics of the compound of formula (I) was evaluated by performing LC/MS quantification of levels of the compound in plasma and urine. Blood samples for pharmacokinetic analysis were collected at pre-determined time points: D1, D4, D7, D14, D21, and D28: pre-dose (within 60 mins prior to dosing) and 0.25, 0.5, 0.75, 1, 1.5, 2, 2.5, 3, 4, 6, 8, 12 hours post-dose; D2, D3, D5, D6, D8 to D13, D15 to D20, D22 to D27, and D29 to D31: pre-dose (within 60 mins prior to dosing); D32: at approximately the same time as the D31 sample was obtained; and D33: prior to discharge (approximately at the same time the pre-dose samples were collected). Sample collection windows were as follows: ±2 mins for <1 hour post-dose; ±5 mins for 1 to 3-hours post-dose; ±10 mins for 4 to 12-hours post-dose. Urine samples for pharmacokinetic analysis were collected at pre-determined time points: D1: pre-dose only; and D3, D6, D10, D17, D24, and D31: 0 to 6 hours, 6 to 12 hours, 12 to 24 hours, and urine volume recorded. Phamacokinetic parameters determined for the compound of formula (I) include, but are not limited to, $AUC_t$, $AUC_{inf}$, $AUC_{tau}$, $C_{max}$, $t_{max}$, $t_{1/2}$, CL/F and Vd/F.

TABLE 23

Schedule of Activities for Part B

| | Trial Period | | | | | | | | | | | | | |
|---|---|---|---|---|---|---|---|---|---|---|---|---|---|---|
| | Screening | Intervention Visit Day | | | | | | | | | | | | |
| | D −28 to D −2 | D −1 | D 1 | D 2- D 6 | D 7 | D 8- D 9 | D 10 | D 11 | D 12- D 13 | D 14 | D 15- D 16 | D 17 | D 18 | D 19- D 20 |
| TRIAL ENTRY AND GENERAL ASSESSMENTS | | | | | | | | | | | | | | |
| Informed Consent | X | | | | | | | | | | | | | |
| Inc/Exc Criteria | X | X | | | | | | | | | | | | |
| Medical History | X | | | | | | | | | | | | | |
| Demographic Data | X | | | | | | | | | | | | | |
| Body Weight/ Height/BMI | X | | | | | | | | | | | | | |
| Drug/Alcohol/ Nicotine Screen | X | X | | | | | | | | | | | | |
| Viral Serology Screen [a] | X | | | | | | | | | | | | | |
| Inpatient Stay/ Telephone Call | | A | X | X | X | X | X | X | X | X | X | X | X | X |
| SAFETY ASSESSMENTS | | | | | | | | | | | | | | |
| Physical Examination | X | X | | | X | | X | | | X | | X | | |
| Clinical Laboratory Evaluations [c] | X | X | | | X | | X | | | X | | X | | |
| Pregnancy Test [d] | X | X | | | | | | | | | | | | |
| Exploratory Urine Biomarkers [e] | | | X | | | | X | | | | | X | | |
| Vital Signs [f] | X | X | X | X | X | X | X | X | X | X | X | X | X | X |
| 12-lead ECG [g] | X | X | | | X | | X | | | X | | X | | |
| Cardiac Telemetry [h] | | | | | | | | | X | | | | | |
| C-SSRS (Baseline/ Screening) | X | | | | | | | | | | | | | |
| C-SSRS (Since Last Visit) [i] | | X | | | X | | | | | X | | | | |
| AE Monitoring and Recording [j] | | | | | | | X | | | | | | | |
| Concomitant Meds/Procedures [j] | | | | | | | X | | | | | | | |
| PHARMACOKINETICS | | | | | | | | | | | | | | |
| Blood Collection for Study Drug Concentration and Metabolites | | | X | X | X | X | X | X | X | X | X | X | X | X |
| Urine Collection for Study Drug Concentration and Metabolites | | | X | X | X | | X | X | | | | X | X | |
| PHARMACODYNAMICS | | | | | | | | | | | | | | |
| EEG including PSG [m] | | X | | | | X | | | | | X | | | |
| qEEG [n] | | X | | | | X | X | | | | X | X | | |
| STUDY DRUG | | | | | | | | | | | | | | |
| Study Drug Administration [o] | | | X | X | X | X | X | X | X | X | X | X | X | X |

TABLE 23-continued

Schedule of Activities for Part B

| | Trial Period | | | | | | | | | | |
|---|---|---|---|---|---|---|---|---|---|---|---|
| | Intervention Visit Day | | | | | | | | | | Safety Follow - UP |
| | D 21 | D 22- D 23 | D 24 | D 25 | D 26- D 27 | D 28 | D 29- D 30 | D 31 | D 32 | D 33 or Discharge | D 36 (±1) or End of Trial |
| TRIAL ENTRY AND GENERAL ASSESSMENTS | | | | | | | | | | | |
| Informed Consent | | | | | | | | | | | |
| Inc/Exc Criteria | | | | | | | | | | | |
| Medical History | | | | | | | | | | | |
| Demographic Data | | | | | | | | | | | |
| Body Weight/ Height/BMI | | | | | | | | | | | |
| Drug/Alcohol/ Nicotine Screen | | | | | | | | | | | |
| Viral Serology Screen [a] | | | | | | | | | | | |
| Inpatient Stay/ Telephone Call | X | X | X | X | X | X | X | X | X | D | TC |
| SAFETY ASSESSMENTS | | | | | | | | | | | |
| Physical Examination | X | | X | | | X | | X | | X [b] | |
| Clinical Laboratory Evaluations [c] | X | | X | | | X | | X | | | |
| Pregnancy Test [d] | | | | | | | | | | X | |
| Exploratory Urine Biomarkers [e] | | | X | | | | | X | | | |
| Vital Signs [f] | X | X | X | X | X | X | X | X | X | X | |
| 12-lead ECG [g] | X | | X | | | X | | X | | | |
| Cardiac Telemetry [h] | | | | | | X | | | | | |
| C-SSRS (Baseline/ Screening) | | | | | | | | | | | |
| C-SSRS (Since Last Visit) [i] | X | | | | | X | | | | X | |
| AE Monitoring and Recording [j] | | | | | | | X | | | | |
| Concomitant Meds/Procedures [j] | | | | | | | X | | | | |
| PHARMACOKINETICS | | | | | | | | | | | |
| Blood Collection for Study Drug Concentration and Metabolites | X | X | X | X | X | X | X | X | X | X | |
| Urine Collection for Study Drug Concentration and Metabolites | | | X | X | | | | X | X | | |

TABLE 23-continued

Schedule of Activities for Part B

| | | | | | | | | |
|---|---|---|---|---|---|---|---|---|
| PHARMACODYNAMICS | | | | | | | | |
| EEG including PSG [m] | | X | | | | | X | |
| qEEG [n] | | X | X | | | | X | X |
| STUDY DRUG | | | | | | | | |
| Study Drug Administration [o] | X | X | X | X | X | X | X | X |

A = admission; AE = adverse event; BMI = body mass index; C-SSRS = Columbia-Suicide Severity Rating Scale; D = discharge; ECG = electrocardiogram; EEG = electroencephalogram; PSG = polysomnogram; qEEG = quantitative electroencephalogram; TC = telephone call.

[a] Hepatitis B, C, and HIV.

[b] Symptom-directed physical examination.

[c] Clinical laboratories include CBC, clinical chemistry, coagulation (Screening only), urinalysis and urine albumin. Collected pre-dose on dosing days.

[d] If applicable, serum hCG at Screening and urine hCG at D −1 and D 33 or discharge.

[e] Urine creatinine and KIM-1. Obtained pre-dose on D 1. Collected pre-dose on dosing days.

[f] Including oral temperature, respiratory rate, supine blood pressure, and pulse rate are obtained as follows: Screening; D −1; D 1, D 4, D 7, D 14, D 21, and D 28: pre-dose (within 60 mins prior to dosing), and 0.25, 1, 2, 3, 4, 6, 8, and 12 hrs post-dose (±15 mins); D 2, D 3, D 5, D 6, D 8 through D 13, D 15 through D 20, D 22 through D 27, and D 26 through 31: 2 hours post-dose (±15 mins); D 32: in the morning; D 33: prior to discharge.

[g] Triplicate measurements at Screening only; Baseline: anytime; During the intervention period: 2 hours after dosing (±15 mins).

[h] Start on Day 6 in the morning pre-dose and continue through Day 33.

[i] During the intervention period C-SSRS to be conducted pre-dose.

[j] Throughout the trial from time of signing informed consent until end of trial.

[m] 24-hour EEGs including PSG. D −1 (Baseline): after confirmation of eligibility until 1 hour prior to dosing on D 1; D 10, D 17, D 24, and D 31: 2 hours prior to dosing until 2 hours prior to dosing on the following day or until approximately 22 hours after dosing on D 32.

[n] D −1 (Baseline): 12:00 noon (±3 hours); D 10, D 17, D 24, and D 31: 4 hours after dosing (±15 mins); D 11, D 18, and D 25: prior to dosing; D 32: at approximately the same time as on D 25. Each qEEG collection period consists of 5 minutes eyes open followed by 5 minutes eyes closed.

Note:

If vital signs assessments are scheduled at the same nominal timepoint as other assessments, the following order should be followed: PK sample, vital signs, ECG, and qEEG, and the vital signs assessments are obtained as close to the scheduled timepoint as possible.

After administration of a single 5 mg dose of the compound of formula (I) to healthy volunteers, plasma concentrations of the compound of formula (I) were quantifiable by 0.50 hours after administration of the compound. After repeat administration of a titration regimen comprised of 4 days of 5 mg (Days 1-4), 4 days of 10 mg (Days 5-8) and 4 days of 20 mg (Days 9-12) of the modified release tablet formulation of the compound of formula (I), detectable predose concentrations of the free base of the compound of formula (I) were observed. Plasma concentrations plateaued after reaching $C_{max}$ and then began to decline over the dose interval. The compound of formula (I) remained quantifiable for the duration of the 24 hour sampling period after administration of a single 5 mg tablet (formulation 4), 2×5 mg tablets (formulation 4) on Day 5 (10 mg) and 1×20 mg tablet (formulation 5) (20 mg) on Day 9. Dose-normalization of concentrations following repeated administration of the modified release tablet formulation of the compound of formula (I) resulted in comparable dose-normalized exposure between 2×5 mg tablets (formulation 4) and a 1×20 mg tablet (formulation 5), demonstrating interchangeability of the 5 mg tablets (formulation 4) and the 20 mg tablets (formulation 5).

TABLE 24

Geometric Mean Values (Geometric CV %) After a Single Oral Dose of 5 mg Tablet Formulation 4 (Day 1), An Oral Dose of 2 × 5 mg Tablet Formulation 4 (Day 5) and An Oral Dose of 20 mg Tablet Formulation 5 (Day 9) Following Repeated Administration

| Parameter | 5 mg (Day 1) [5 mg MR formulation 4 Tablet × 1] (N = 8) | 10 mg (Day 5) [5 mg MR formulation 4 Tablet × 2] (N = 8) | 20 mg (Day 9) [20 mg MR formulation 5 Tablet × 1] (N = 8) |
|---|---|---|---|
| $t_{lag}$ (h)[1] | 0.50 (0.25-0.75) | 0.00 (0.00-0.00) | 0.00 (0.00-0.00) |
| $t_{max}$ (h)[1] | 12.00 (2.0-12.0) | 2.00 (1.5-12.0) | 1.50 (2.5-8.0) |
| $C_{max}$ (ng/mL) | 9.90 (23.3) | 26.7 (25.5) | 50.7 (22.5) |
| $AUC_{24}$ (ng*h/mL) | 179 (22.2) | 445 (22.0) | 829 (11.2) |

$AUC_{24}$ = area under the plasma concentration-time curve from time of dosing to 24 hours after dosing, $C_{max}$ = maximum (peak) plasma drug concentration. CV % = percent coefficient of variation, MR = modified-release, $t_{lag}$ = lag time, $t_{max}$ = time of maximum (peak) plasma drug concentration.

[1] Median (range).

Figure 13:
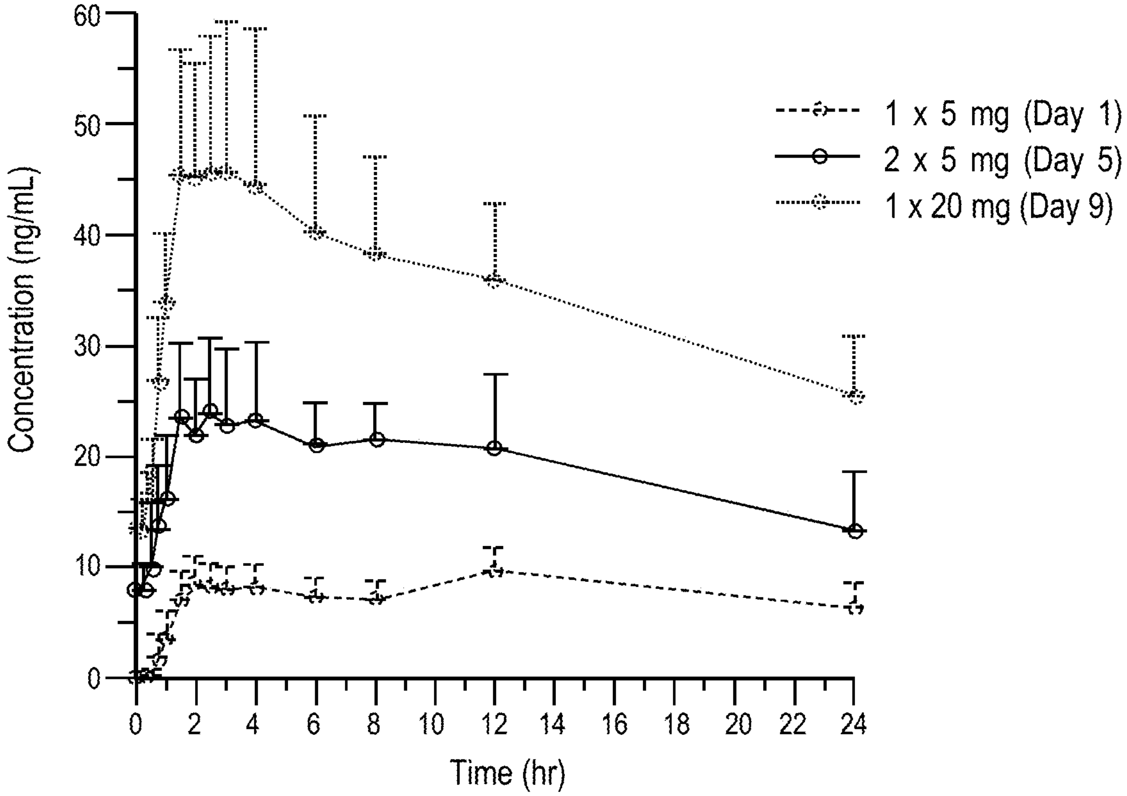
FIG. 13 shows mean (±SD) concentrations after a single oral dose of 5 mg tablet formulation 4 (Day 1), an oral dose of 10 mg (2×5 mg tablet formulation 4) (Day 5) and an oral dose of 20 mg tablet formulation 3 (Day 9) following repeated administration.

FIG. 13 shows mean (±SD) concentrations after a single oral dose of 5 mg tablet formulation 4 (Day 1), an oral dose of 10 mg (2×5 mg tablet formulation 4) (Day 5) and an oral dose of 20 mg tablet formulation 3 (Day 9) following repeated administration.

Figure 14:
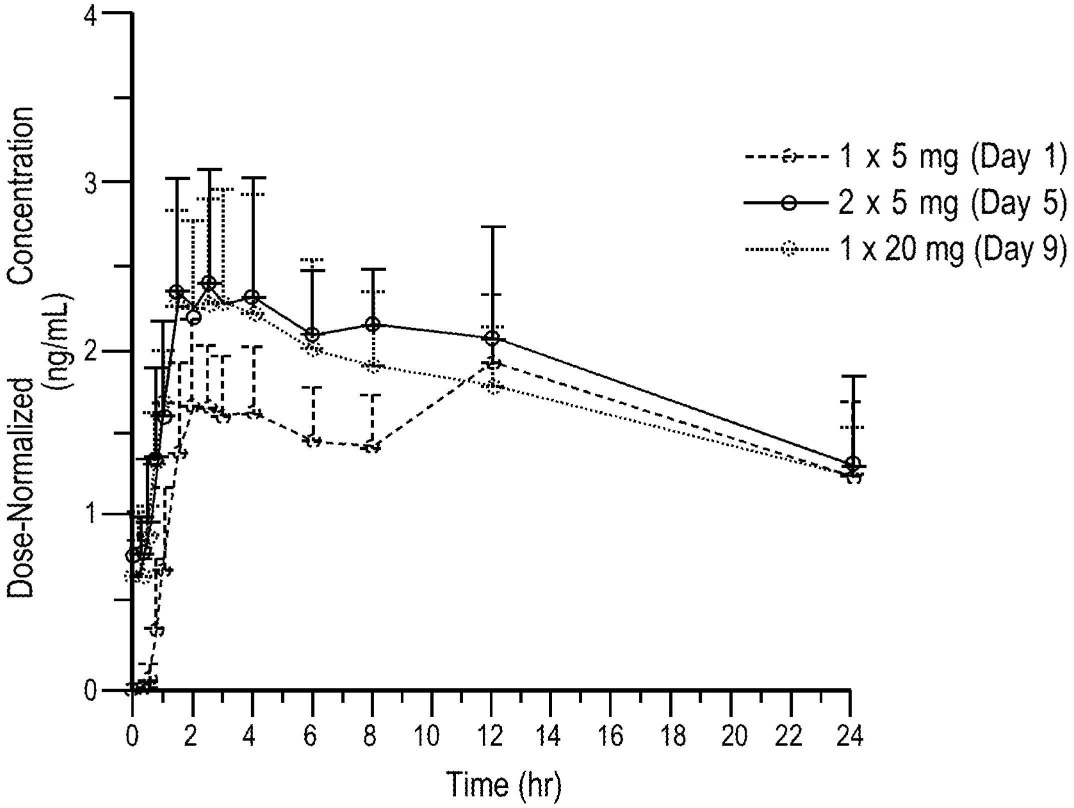
FIG. 14 shows mean (±SD) dose-normalized concentrations after a single oral dose of 5 mg tablet formulation 4 (Day 1), an oral dose of 10 mg (2×5 mg tablet formulation 4) (Day 5) and an oral dose of 20 mg tablet formulation 5 (Day 9) following repeated administration.

FIG. 14 shows mean (±SD) dose-normalized concentrations after a single oral dose of 5 mg tablet formulation 4 (Day 1), an oral dose of 10 mg (2×5 mg tablet formulation 4) (Day 5) and an oral dose of 20 mg tablet formulation 5 (Day 9) following repeated administration.

In Part A of the study, the 5 mg tablet formulation was assessed in a within-participant escalating dose paradigm from 5 mg to 20 mg per day. In Part B, doses between 20 and 120 mg per day were assessed in a within-participants dose escalating titration design. Dosing of Part A and Part B of the study has been completed. By incorporating a titrated dosing schedule, it was surprisingly found that the compound of formula (I) was well-tolerated at dose levels up to and including 120 mg per day, more than double the amount of a dose that was not tolerated when administered without titration (see Example 4). Furthermore, by using a titrated dosing schedule, it was also surprisingly found that pharmacokinetic values, like $C_{max}$ and $AUC_{24}$, could be increased at least about 2-3 fold above the pharmacokinetic values obtained with a lower dosage that was not tolerated when administered without titration (see Example 4). There have been no SAEs and no severe AEs. The majority of AEs were mild, transient, and resolved without intervention. There were no treatment related ECG or EEG abnormalities. To date safety laboratory values have generally been within normal limits and there have been no dose dependent excursions from the normal range. As the highest dose tested was well tolerated in the titration scheme, no maximum tolerated dosage was identified, suggesting that even higher dosages and/or pharmacokinetic parameters can be achieved and safely tolerated.

TABLE 25

Pharmacokinetic data from Part B dose escalation study

| Dose of Formulation B | Day of study | $C_{max}$ ng/mL (CV %) | Median $t_{max}$ hr (range) | $AUC_{\tau}^{a}$ ng · h/mL (CV %) |
|---|---|---|---|---|
| 20 mg | 1 | 42 (39.9) | 3.26 (1.5-12.0) | 657 (36.3) |
| 40 mg | $4^{b}$ | 106 (33.0) | 2.00 (1.5-12.0) | 1622 (33.4) |
| 60 mg | $7^{b}$ | 175 (27.1) | 2.00 (1.5-12.0) | 2667 (12.5) |
| 80 mg | $14^{b}$ | 239 (29.7) | 2.00 (1.5-12.0) | 3257 (22.4) |
| 100 mg | $21^{b}$ | 307 (25.8) | 1.53 (1.5-4.0) | 3762 (16.3) |
| 120 mg | $28^{b}$ | 379 (17.7) | 1.50 (1.5-2.5) | 4637 (14.9) |

$AUC_{\tau}$ = Area under the plasma concentration-time curve during a dosage interval;
$C_{max}$ = Maximum (peak) plasma drug concentration;
$t_{max}$ = Time to reach maximum (peak) plasma concentration following drug administration
[a]Interval is 24 hours for single dose studies ($AUC_{24}$)
[b]This study day represents the first day of dosing for this dose level Eight participants each completed Part A and Part B. Participants reported no severe or serious adverse events, and no clinically adverse changes in safety laboratory tests, vital signs, ECGs, or EEGs were observed. A summary of treatment-emergent adverse events is provided below in Table 26 (Part A) and Table 27 (Part B).

TABLE 26

Treatment-Emergent Adverse Events Occurring in 2 or More Participants for Escalating Dosages 5-20 mg (Part A)

| MedDRA Preferred Term | 5 mg (N = 8) n (%) | 10 mg (N = 8) n (%) | 20 mg (N = 8) n(%) | Overall (N = 8) n (%) |
|---|---|---|---|---|
| Participants with at least one TEAE | 5 (62.5%) | 5 (62.5%) | 3 (37.5%) | 7 (87.5%) |
| General Disorders and Administration Site Conditions | 3 (37.5%) | 3 (37.5%) | 1 (12.5%) | 4 (50.0% |
| Medical device site dermatitis | 1 (12.5%) | 2 (25.0%) | 0 | 3 (37.5%) |
| Vessel puncture site thrombosis | 1 (12.5%) | 1 (12.5%) | 0 | 2 (25.0%) |
| Eye disorders | 2 (25.0%) | 2 (25.0%) | 0 | 3 (37.5%) |
| Dry eye | 1 (12.5%) | 2 (25.0%) | 0 | 3 (37.5%) |
| Nervous System Disorders | 2 (25.0%) | 0 | 1 (12.5%) | 3 (37.5%) |
| Headache | 2 (25.0%) | 0 | 1 (12.5%) | 3 (37.5%) |
| Lethargy | 1 (12.5%) | 0 | 1 (12.5% | 2 (25.0%) |

MedDRA = Medical Dictionary for Regulatory Activities;
TEAE = treatment-emergent adverse even

TABLE 27

| Treatment-Emergent Adverse Events Occurring in 2 or More Participants for Escalating Dosages 20-120 mg (Part B) | | | | | | | | |
|---|---|---|---|---|---|---|---|---|
| MedDRA Preferred Term | Placebo (N = 4) n (%) | 20 mg (N = 12) n (%) | 40 mg (N = 11) n (%) | 60 mg (N = 11) n (%) | 80 mg (N = 9) n (%) | 100 mg (N = 8) n (%) | 120 mg (N = 8) n (%) | Overall (N = 12) n (%) |
| Participants with at least one TEAE | 3 (75.0%) | 5 (41.7%) | 3 (27.3%) | 5 (45.5%) | 2 (22.2%) | 6 (75.0%) | 2 (25.0%) | 12 (100%) |
| General Disorders and Administration Site Conditions | 2 (50.0%) | 2 (16.7%) | 1 (9.1%) | 2 (18.2%) | 0 | 1 (12.5%) | 2 (25.0%) | 6 (50.0%) |
| Medical device site dermatitis | 2 (50.0%) | 1 (8.3%) | 0 | 1 (9.1%) | 0 | 1 (12.5%) | 1 (12.5%) | 3 (25.0%) |
| Chest discomfort | 0 | 1 (8.3%) | 1 (9.1%) | 0 | 0 | 0 | 0 | 2 (16.7%) |
| Intoxicated sensation | 0 | 2 (16.7%) | 0 | 0 | 0 | 0 | 1 (12.5%) | 2 (16.7%) |
| Nervous System Disorders | 2 (50.0% | 2 (16.7%) | 2 (18.2%) | 2 (18.2%) | 1 (11.1%) | 1 (12.5%) | 0 | 5 (41.7%) |
| Dizziness | 0 | 0 | 2 (18.2%) | 0 | 1 (11.1%) | 0 | 0 | 3 (25.0%) |
| Headache | 2 (50.0%) | 1 | 0 | 1 (9.1%) | 0 | 0 | 0 | 2 (16.7%) |
| Cardiac Disorders | 0 | 2 (16.7%) | 0 | 1 (9.1%) | 0 | 1 (12.5%) | 0 | 4 (33.3%) |
| Palpitations | 0 | 2 (16.7%) | 0 | 0 | 0 | 0 | 0 | 2 (16.7%) |

MedDRA = Medical Dictionary for Regulatory Activities;
TEAE = treatment-emergent adverse even As shown above, at the highest dose of 120 mg, there were few AEs, including 1 event of intoxicated sensation and 1 event of medical device site dermatitis. No treatment-related ECG or EEG abnormalities were observed. Safety laboratory values were generally within normal limits with no dose-dependent excursions from the normal range. There were no treatment-emergent abnormalities in kidney function or in exploratory kidney biomarkers (KIM-1), and no treatment-emergent changes in the C-SSRS were observed.

Overall, the data indicate that dosing of up to 120 mg with titration is well-tolerated and is not associated with AEs seen in earlier studies of administration of a compound of formula (II) without titration, such as nausea and vomiting observed with single-dose administration of 60 mg tablets discussed above, or administration of a 40 mg immediate release formulation of a compound of formula (II).

Example 12—Food Effects

The effect of a high-fat, high-calorie meal on the pharmacokinetics of a compound of formula (II) was evaluated in an open-label, sequential fashion following a single 20 mg dose of formulation 5 in participants who had previously received a 20 mg dose of formulation 5 under fasted conditions.

Co-administration of formulation 5 with a high-fat, high-calorie meal resulted in a modest increase in AUC (14% to 15%), and a 49% increase in $C_{max}$ compared to the fasted state, as shown below in Table 28. Relative to the fasted state, the $t_{max}$ of formula (II) was delayed from 4.0 hours to 5.0 hours when co-administered with a high-fat, high-calorie meal.

TABLE 28

| Assessment of Co-administration of a High-Fat/High-Calorie Meal on Formula (II) Exposure Following a Single 20 mg Oral Dose | | | | |
|---|---|---|---|---|
| Parameter | Fasted Geometric Mean (Adjusted) | Fed Geometric Mean (Adjusted) | Ratio | 90% CI |
| $C_{max}$ | 43.6 | 64.7 | 1.49 | 1.26, 1.75 |
| $AUC_{last}$ (ng · h/mL) | 905 | 1040 | 1.14 | 1.03, 1.27 |
| $AUC_{\infty}$ (ng · h/mL) | 942 | 1080 | 1.15 | 1.01, 1.30 |

$AUC_{last}$ = Area under the plasma concentration-time curve from time zero to time of last measurable concentration
$AUC_{\infty}$ = ArEa under the plasma concentration-time curve from time zero to infinity;
$C_{max}$ = Maximum (peak) plasma drug concentration

Example 13—Pharmacodynamics and EEG Sleep Studies

Figure 12:
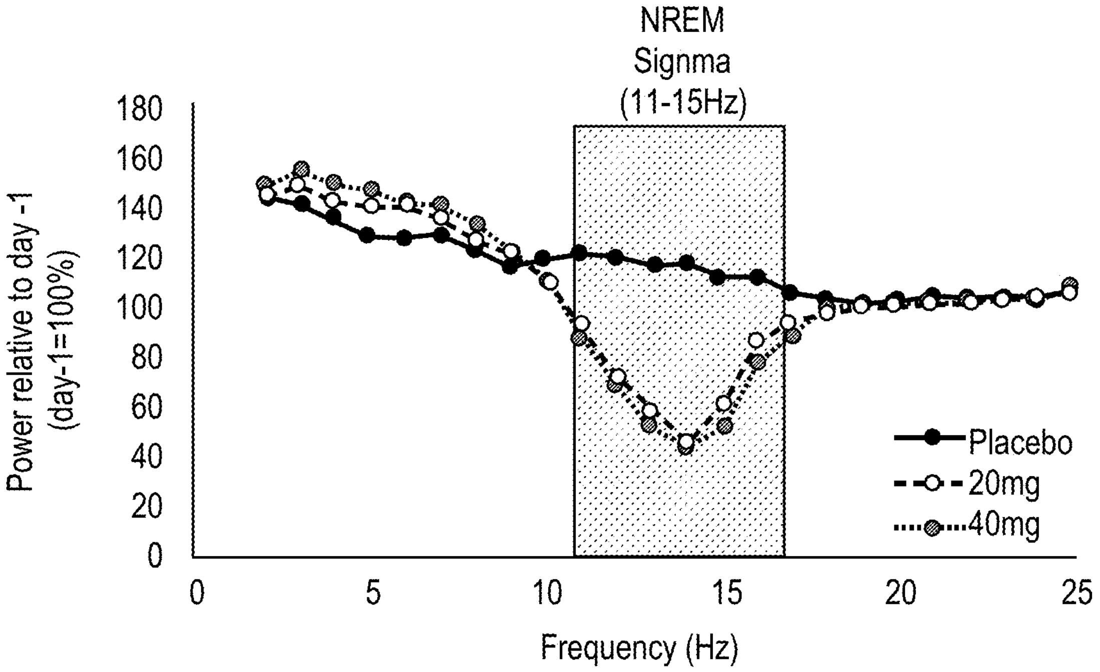
FIG. 12 shows Phase 1 Sleep EEG in healthy volunteers (NREM sigma).
Figure 17:
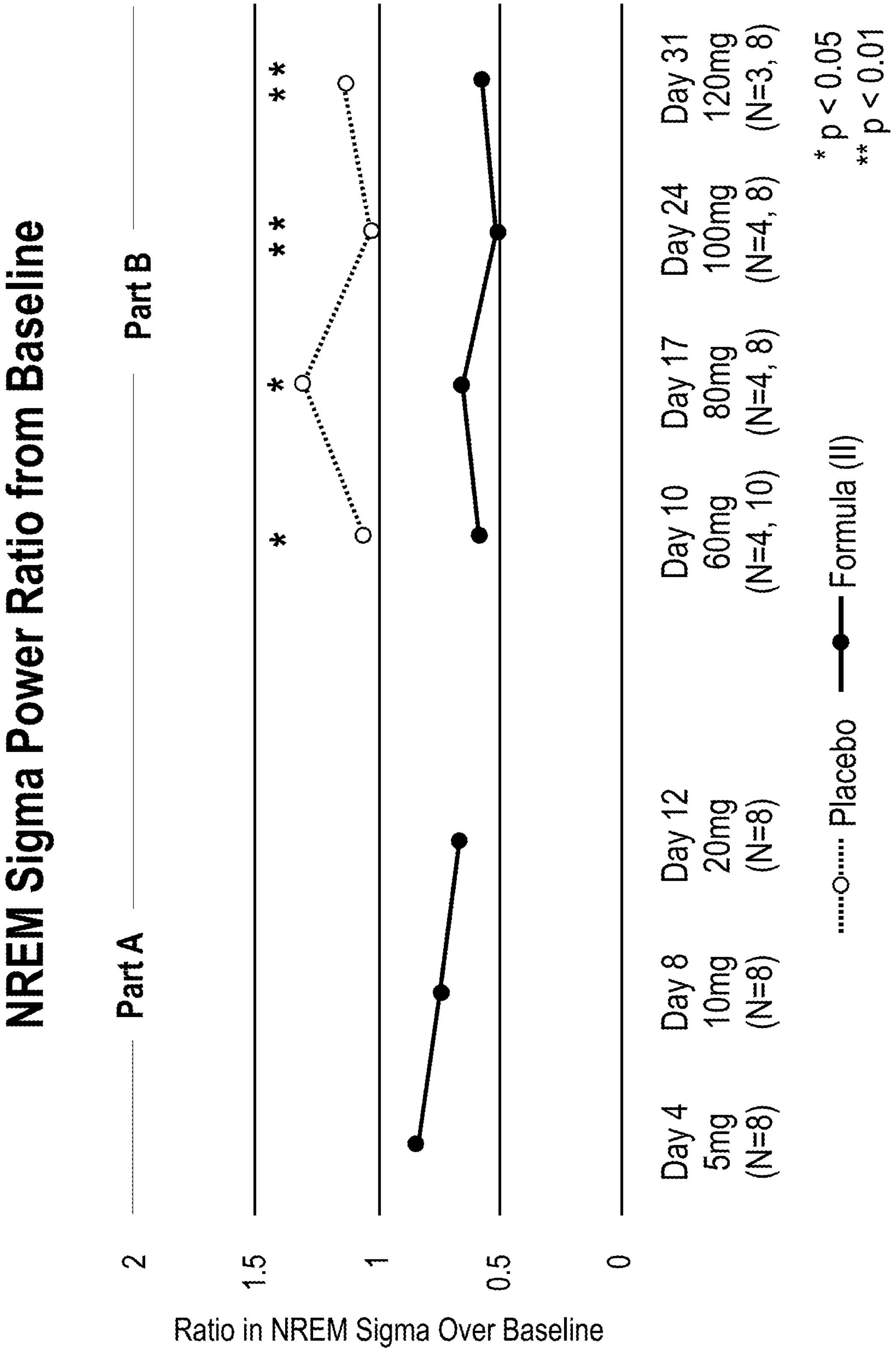
FIG. 17 shows the NREM sigma power ratio from a baseline for escalating dosages of administration of a compound of formula (II), as described in Example 13.

As shown in FIG. 12, administration of both a 20 mg tablet of a compound of formula (II) and a 40 mg tablet of a compound of formula (II) resulted in a decrease in the NREM sigma band as compared to a placebo control. The effects of multiple doses of a wider dose range (Part A: 5, 10, 20 mg; Part B: 60, 80, 100, 120 mg) on sigma band EEG power during NREM sleep were also evaluated as part of the protocol described in Example 11, above. 24-hour EEG/PSG recordings were performed the day before dosing (baseline day) and after dosing on Days 4, 8, and 12 (for Part A) or Days 10, 17, 24, and 31 (for Part B). Part B also included placebo-treated participants for statistical comparisons. A clear dose-dependent decrease from baseline in sigma band EEG power during NREM sleep across each of the dose ranges tested was observed until the decrease plateaued after Day 17, as shown in FIG. 17 and reported in Table 29, below. Statistical analysis of data from Part B resulted in significant differences in sigma band EEG power (i.e., a decrease until a plateau corresponding to administration at 80 mg), relative to placebo-treated subjects at each dose level.

TABLE 29

| NREM Sigma Power Ratio from Baseline | | | | | | | |
|---|---|---|---|---|---|---|---|
| | Placebo (N = 4) | | Formula (II) (N = 10) | | Formula (II) v. Placebo | | |
| Time | LS Means | Ratio | LS Means | Ratio | Difference (95% CI) | Difference Ratio (95% CI) | p-value |
| Day 10 | 0.055 | 1.056 | −0.542 | 0.581 | −0.597 (−1.0421, −0.1518 | 0.550 (0.3527, 0.8592) | 0.0132 |
| Day 17 | 0.260 | 1.297 | −0.437 | 0.646 | −0.697 (−1.3596, −0.0352) | 0.498 (0.2568, 0.9654) | 0.0407 |
| Day 24 | 0.031 | 1.032 | −0.698 | 0.498 | −0.729 (−1.0941, −0.3639) | 0.482 (0.3349, 0.6950) | 0.0011 |
| Day 31 | 0.123 | 1.131 | −0.556 | 0.574 | −0.679 (−1.1581, −0.1997) | 0.507 (0.3141, 0.8190) | 0.0098 |

A further effect on gamma band EEG power was observed at higher doses. For Part B of the study described in Example 11 above, there was a dose-related reduction in gamma power, beginning at 60 mg and continuing through to 120 mg. It appears a maximal effect in gamma reduction was not achieved.

The pharmacokinetic/pharmacodynamic (PKPD) effects of administration a compound of formula (II) on EEG were also evaluated. The recording of the NREM sigma absolute power was reported as a single summary value of a single night of sleep following each dose on pre-specified days (baseline and Days 4, 8 and 12 for Example 11, Part A and Days 10, 17, 24, and 31 for Part B, as set forth in Tables 22 and 23, above. Each NREM sigma absolute power value was paired with a model predicted average plasma concentration ($C_{ave}$) that corresponded to the 24-hour EEG recording period on the respective study day. For example, if the period of EEG recording for an individual was from 6 am on Day 4 to 6 am on Day 5, then the corresponding $C_{ave}$ was calculated as the average of the individual's model-predicted concentrations (sampled every 30 minutes) from that same time period. The resulting PKPD data were analyzed in a mixed-effects modelling framework using NONlinear Mixed Effects Modeling (NONMEM) software. The change from baseline NREM sigma absolute power was specified as the outcome and the primary explanatory variable was the $C_{ave}$ of a compound of formula (II).

The eyes open (EO) and eyes closed (EC) gamma absolute power for each individual was also estimated at specific time points across the study days. These data were analyzed in a conventional population PKPD modeling framework that linked model predicted compound concentrations at a timepoint to the corresponding EO or EC gamma absolute power at that timepoint.

The population PK model was used to generate $C_{ave}$ for NREM sigma absolute power and concentrations for EO and EC gamma absolute power. For NREM sigma absolute power, the $C_{ave}$ was computed for the final day of each dose level over the EEG collection interval. For EO and EC gamma absolute power, concentrations at 4 hours post-dose and 23.75 hours post-dose were generated on the final day of each dose level. The final population PKPD models for NREM sigma absolute power and EO and EC gamma absolute power were then used to generate corresponding EEG responses.

Figure 18:
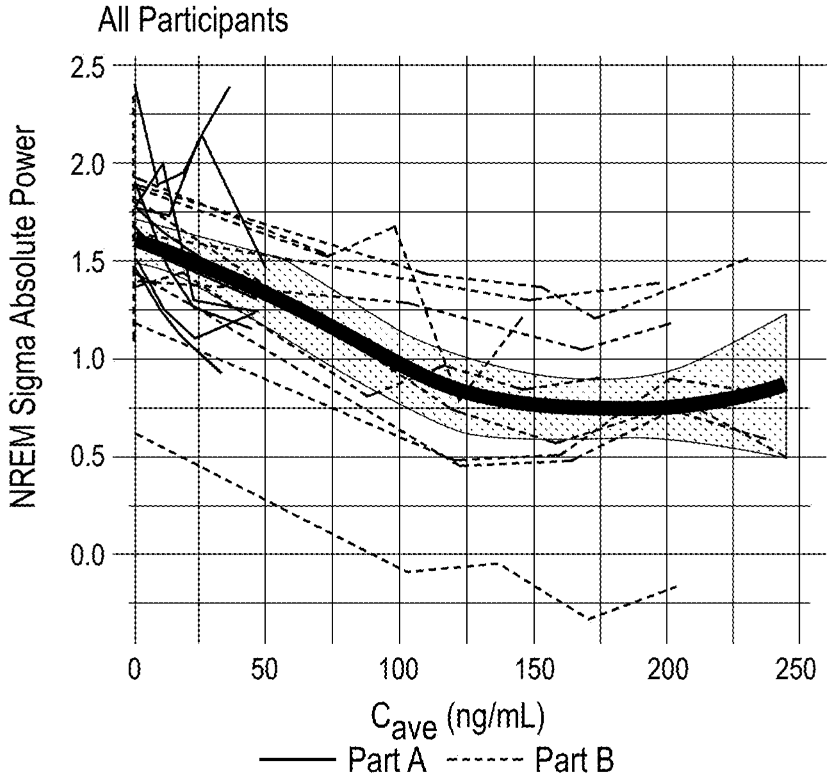
FIG. 18 shows the NREM sigma absolute power versus the average concentration ($C_{ave}$), as described in Example 13, wherein the thick black line represents a non-parametric smoother, and the shaded region represents the 95% confidence interval for the smoother. Individual trajectories are represented by solid thin lines for Part A and dotted thin lines for Part B.

For NREM sigma absolute power, maximum reduction in signal appeared to occur after being titrated up to a $C_{ave}$ of greater than about 180 ng/mL. See FIG. 18, showing the NREM sigma absolute power over average concentration, wherein individual trajectories are represented by solid thin lines for Part A and dotted thin lines for Part B, as described in Example 11.

Figure 19:
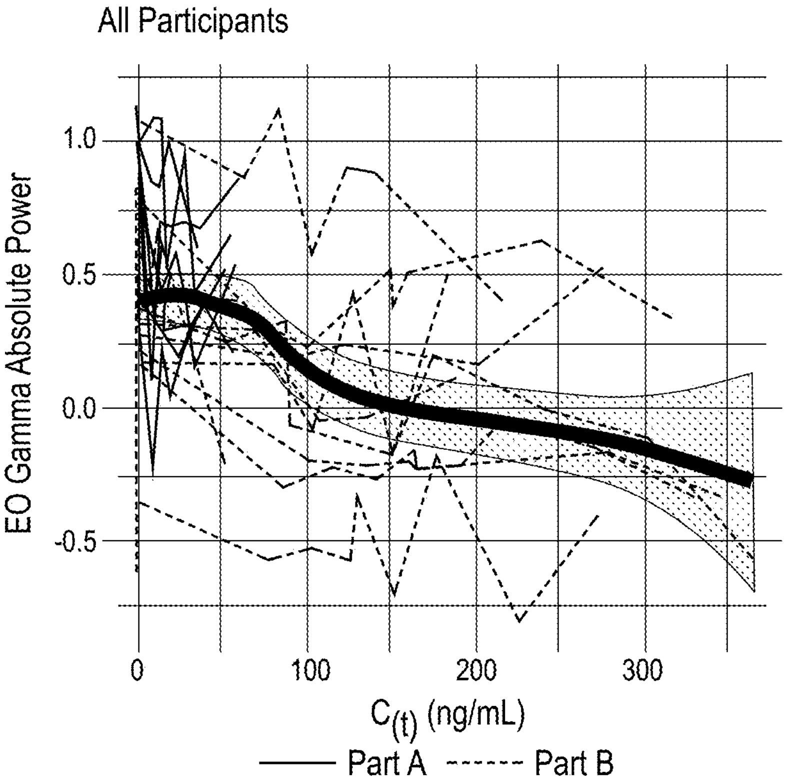
FIG. 19 shows the eyes open (EO) gamma absolute power versus the concentration at time of measurement ($C_{(t)}$), as described in Example 13, wherein the thick black line represents a non-parametric smoother, and the shaded region represents the 95% confidence interval for the smoother. Individual trajectories are represented by solid thin lines for Part A and dotted thin lines for Part B.

For EO gamma absolute power, maximum reduction in signal appeared to occur after being titrated up to $C_{(t)}$ of >300 ng/mL (titrated up to 120 mg). The simulations suggested that reductions in signal were greatest after the final dose of 120 mg. See FIG. 19, showing the EO gamma absolute power over concentration, wherein individual trajectories are represented by solid thin lines for Part A and dotted thin lines for Part B, as described in Example 11.

Figure 20:
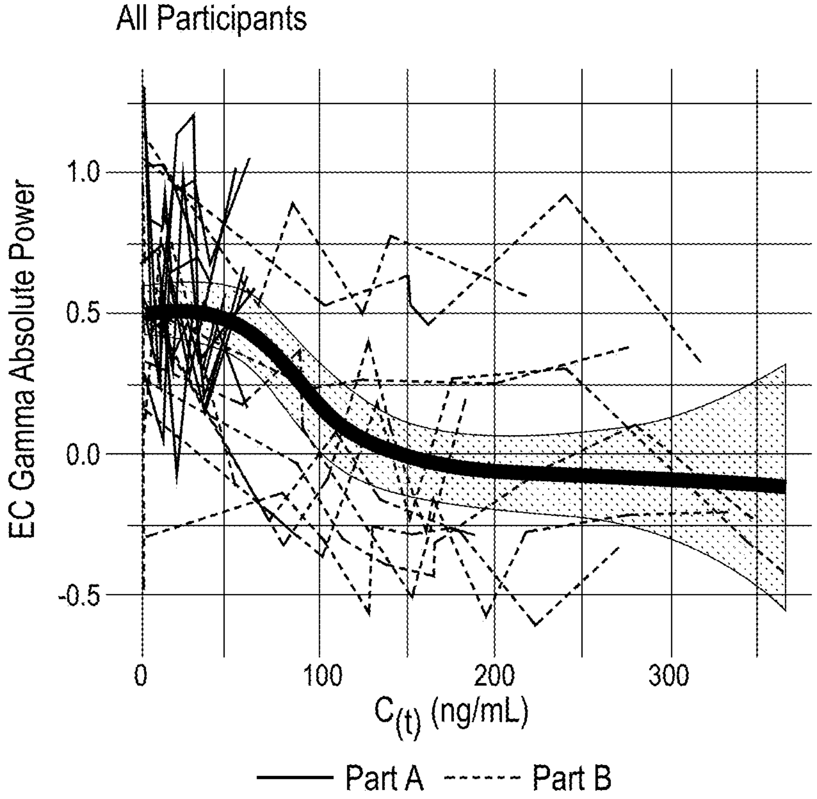
FIG. 20 shows the eyes closed (EC) gamma absolute power versus the concentration at time of measurement ($C_{(t)}$), as described in Example 13, wherein the thick black line represents a non-parametric smoother, and the shaded region represents the 95% confidence interval for the smoother. Individual trajectories are represented by solid thin lines for Part A and dotted thin lines for Part B.

For EC gamma absolute power, maximum reduction in signal appeared to occur after being titrated up to 120 mg, which corresponds to $C_{(t)}$ of >300 ng/mL (titrated up to 120 mg). As with EO gamma absolute power, the simulations suggested that reductions in signal were greatest after the final dose of 120 mg. See FIG. 20, showing the EC gamma absolute power over concentration, wherein individual trajectories are represented by solid thin lines for Part A and dotted thin lines for Part B, as described in Example 11.

Example 14— Evaluation of Safety, Tolerability, Pharmacokinetics and Pharmacodynamics of Dose-Titration of the Compound of Formula (I) in a within-Participant Escalating Dose Paradigm This single-center, multi-part, Phase 1, randomized, double-blind, placebo-controlled clinical trial will assess the safety, tolerability, and pharmacokinetics of titrating a compound of formula (I) up to 120 mg in healthy male and female participants aged 18 to 54 years and in participants aged 55 to 75 years. Specific endpoints will include incidence and severity of AEs, changes in vital sign measurements, changes in clinical laboratory results, changes in ECG parameters, and incidence of C-SSRS measured suicidal ideation or behavior. With respect to pharmacokinetic endpoints, plasma concentration over time will be measured, as well as $AUC_t$, $AUC_{tau}$, $C_{max}$, and $t_{max}$. Additionally, the geometric mean ratio between age groups for $C_{max}$ and $AUC_{tau}$ will be measured. The screening period for both Parts A and B will be up to 29 days (Day −29 to Day −1) with the Baseline Visit on Day −1. Screening assessments will include medical history, demographics, vital signs, physical examination (including height and weight), drug screen, viral serological tests, clinical laboratory tests, ECG, and C-SSRS evaluations. All study drug administration in both Parts A and B will occur in the fasted state; no food or drink, except water, will be allowed for at least 10 hours prior to dosing.

In Part A of this study, titration regimens to reach a dosage of 120 mg in less than 28 days, such as 14 days or less, 12 days or less, 10 days or less, or 7 days or less, will be explored. Specifically, in one aspect, an initial daily dose of 20 mg or matching placebo will be administered daily for 3 days (Day 1 to Day 3), followed by 40 mg daily for 3 days (Day 4 to Day 6), 80 mg daily for 3 days (Day 7 to Day 9), and 120 mg daily for 5 days (Day 10 to Day 14). For all cohorts, the titration regimen including dose levels studied will be fixed prior to the start of dosing in each respective cohort with the maximum dose level of 120 mg and each dose level increment not to exceed 60 mg, such as not to exceed 40 mg.

In Part B of this study, the same titration regimen(s) described in Part A of this Example as well as in Part B of Example 11 above will be explored in older, healthy participants aged 55 to 75 years. Specifically, in one aspect, an initial daily dose of 20 mg or matching placebo will be administered daily for 3 days (Day 1 to Day 3), followed by 40 mg daily for 3 days (Day 4 to Day 6), 60 mg daily for 7 days (Day 7 to Day 13), 80 mg daily for 7 days (Day 14 to 20), 100 mg daily for 7 days (Day 21 to Day 27), and 120 mg daily for 4 days (Day 28 to Day 31). Patients will be allowed to receive the compound of formula (I) daily at each of 60 mg, 80 mg, and 100 mg dose levels for an extended period of up to 2 days.

Example 15—Determination of Formula (II) Voltage Dependence of Calcium Channel Inhibition The voltage dependence of calcium channel isoforms was determined by comparing the activity of resting (Tonic Block) and half-inactivated (Voltage Dependent Block) voltages across various concentrations of Formula (II). First, HEK-293 cells containing $hCa_v3.1$, $hCa_v3.2$, or $hCa_v3.3$ calcium channel isoforms were prepared by seeding at $2\times10^6$ cells per flask in culture for 2 days; the cells were then harvested at about $6\times10^6$ cells. Harvested cells were washed once in DPBS for approximately 30 minutes, and 1 mL of 1× (0.05%) Trypsin-EDTA was added, swirled, and allowed to sit on the cells for approximately 4 minutes. 10 mL of warmed DMEM high glucose media supplemented with 10% fetal bovine serum, 2 mM sodium pyruvate, 10 mM HEPES, and 400 μg/mL G418 was added, and the cells were triturated until a single cell suspension was added. Cells were placed in a 250 mL centrifuge tube with 30 mL warmed media and gently rocked at 28° C. for approximately 1 hour. Cell aliquots of 5 mLs ($1\times10^6$ cells) were then centrifuged at 100× for 2 minutes, and supernatant was removed. Next, 100 μl of external recording solution was added to the remaining cell pellet and triturated 20 times to achieve a single cell suspension.

Formula (II) (420.35 g/mol provided as a powder) was prepared in DMSO stock, and the potency of current inhibition ($IC_{50}$) was determined. Immediately prior to assay, Formula (II) was diluted with DMSO to 300× the designated final concentration. All studies were performed using the Molecular Devices PatchXpress automated patch clamp platform at room temperature.

To determine the $hCa_v3.1$, $hCa_v3.2$, and $hCa_v3.3$ peak current from a resting, closed state (tonic block), currents were evokes by depolarizing pulses to −25 mV (10 ms) from −120 mV (a non-inactivated holding potential) at a frequency of 0.1 Hz. Peak current was defined as the peak inward current during Epoch 1 with no leak subtraction applied. Current stability was monitored, and the potency of each compound was determined using concentration response curves. Compounds were tested to a maximum concentration that produced either >85% block or solubility concerns (e.g., compound precipitation).

Pharmacology was measured during Epoch 1. Percent inhibition was calculated as: 100*((([Step 2+Step 5]/2)−Step 3)/(Step 2+Step 5/2)), wherein Step 2 is the peak current measured at baseline, Step 5 is the current measured during the wash period, and Step 3 is the peak current measured during application of the compound. The average of the final 3 consecutive currents in each experimental procedure was used for all calculations. The concentration response curve was fit with a Hill equation to derive $IC_{50}$, slope, minimum response, and maximum response fitting parameters.

To calculate the $hCa_v3.1$, $hCa_v3.2$, and $hCa_v3.3$ peak current from a half-inactivated state (voltage dependent block), currents were first evoked by depolarizing pulses to −25 mV (10 ms) from a non-inactivating holding potential (−120 mV) at a frequency of 0.1 Hz. After current amplitude became stable, the mid-point average of steady state inactivation was determined for each cell using a series of 9,900 ms conditioning steps to increasingly depolarize voltages (ranging from $V_{hold}$ (−120 mV) to −40 mV) preceding a test pulse to −25 mV (10 ms) to establish the magnitude of inactivation. The holding command potential was then set to the voltage that produced approximately 50% inactivation ($V_{0.5}$) using PatchXpress scripts. From this $V_{0.5}$ potential, a voltage step to −25 mV (10 ms) was used to evoque peak current. The voltage was stepped to −120 mv (50 ms) to evoque tail currents and monitor cell integrity.

The effect of the compound on peak current amplitude was monitored using the voltage protocol described above and washed out after reaching steady state as determined by PatchXpress stability scripts. Washout was performed at the original holding potential of −120 mV to facilitate reversal of state-dependent interactions. Washout current for the calculation of inhibition was determined by resetting the holding potential to the previously determined half-inactivation potential ($V_{0.5}$) and measuring peak current from this holding potential. Pharmacology was measured during Epoch 1, and percent inhibition was calculated as discussed above for tonic block.

Formula (II) was found to produce a concentration dependent inhibition of peak calcium current expressed by $hCa_v3.1$, $hCa_v3.2$, and $hCa_v3.3$ channels. The extent of tonic block and voltage dependent block was similar across all channels, consistent with a comparable potency for each isoform. The compound of formula (II) was between 2- and 4-fold more potent on voltage dependent block compared to tonic block, demonstrating a voltage dependence for the inhibitions of all $hCa_v3$ isoforms. The results are shown below in Table 30 (tonic block) and Table 31 (voltage dependent block).

TABLE 30

| Formula (II) Inhibition of hCav3.x for Tonic Block | | | | | | |
|---|---|---|---|---|---|---|
| | hCa$_v$3.1 | | hCa$_v$3.2 | | hCa$_v$ 3.3 | |
| Conc (μm) | Mean (n) | SD | Mean (n) | SD | Mean (n) | SD |
| 0.09 | 8.8 (7) | 6.5 | 12.6 (4) | 16.8 | 3.8 (7) | 14.5 |
| 0.27 | 29.4 (11) | 7.2 | 37.1 (6) | 9.3 | 23.0 (11) | 9.2 |
| 0.91 | 50.2 (9) | 10.6 | 55.1 (13) | 11.1 | 54.5 (5) | 5.5 |
| 2.74 | 67.5 (10) | 11.7 | 76.2 | 11.6 | 77.1 (6) | 6.3 |
| 9.13 | 76.6 (9) | 11.4 | 89.7 | 2.3 | 92.1 (5) | 1.6 |
| 27.40 | 89.5 (4) | 6.7 | 96.9 | 0.9 | 94.6 (5) | 4.0 |
| 91.33 | — | — | 98.2 | 2.7 | — | — |

TABLE 31

| Formula (II) Inhibition of hCav3.x for Voltage Dependent Block | | | | | | |
|---|---|---|---|---|---|---|
| | hCa$_v$3.1 | | hCa$_v$3.2 | | hCa$_v$ 3.3 | |
| Conc (μm) | Mean (n) | SD | Mean (n) | SD | Mean (n) | SD |
| 0.03 | 13.9 (12) | 8.9 | 16.6 (11) | | 12.9 (8) | 8.9 |
| 0.09 | 29.7 (14) | 8.6 | 31.2 (7) | | 26.9 (17) | 16.1 |
| 0.27 | 55.2 15) | 11.1 | 48.4 (9) | | 58.7 (19) | 10.8 |
| 0.91 | 73.8 (9) | 7.1 | 78.8 (12) | | 76.9 (20) | 10.6 |
| 2.74 | 84.6 (9) | 8.3 | 91.6 (13) | | 89.4 (20) | 6.6 |
| 9.13 | 86.0 (7) | 6.0 | — | — | 92.9 (4) | 5.3 |

The compound of formula (II) demonstrated concentration and voltage dependent inhibition of peak currents produced by hCav3.1, hCav3.2, and hCav3.3 channels. Potency for voltage dependent block ranged from 172 nM to 341 nM and was between 2- and 4-fold more potent than the measured tonic (resting) block. Specifically, the tonic block/voltage dependent block (TB/VDB) ratio for 3.8, 2.0, and 4.0 for hCa$_v$3.1, hCa$_v$3.2, and hCa$_v$3.3, respectively.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The invention claimed is:

1. A method of treating a subject suffering from essential tremor, the method comprising administering to said subject a titrated dose of a compound of formula (I):

(I)

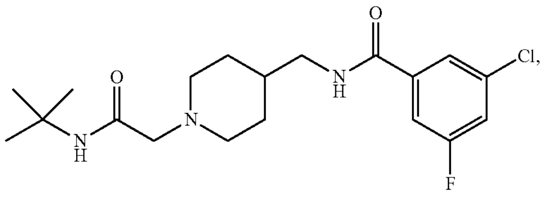

or a pharmaceutically acceptable salt thereof, wherein administering the titrated dose of the compound of formula (I), or a pharmaceutically acceptable salt thereof, comprises:

(a) administering to said subject a first dose of the compound of formula (I), or a pharmaceutically acceptable salt thereof, of about 5 mg to about 40 mg per day for a first period of time;

(b) administering to said subject one or more increased doses of the compound of formula (I), or a pharmaceutically acceptable salt thereof, wherein the one or more increased doses are increased relative to the first dose, to arrive at a maximum titrated dose of about 20 mg to about 120 mg per day; and (c) administering the maximum titrated dose of the compound of formula (I), or a pharmaceutically acceptable salt thereof, to the subject.

2. The method of claim 1, wherein the first period of time is 3 days.

3. The method of claim 1, wherein in step (b), the one or more increased doses of the compound of formula (I), or a pharmaceutically acceptable salt thereof, are administered to the subject for a period of time ranging from 3 days to 7 days.

4. The method of claim 1, wherein in the first period of time, the compound of formula (I), or a pharmaceutically acceptable salt thereof, is administered at a dose of about 20 mg to about 40 mg per day.

5. The method of claim 1, wherein step (b) comprises:

(i) increasing the first dose to a second dose and administering the second dose of the compound of formula (I), or a pharmaceutically acceptable salt thereof, to the subject for a second period of time, wherein the second dose is about 40 mg to about 80 mg per day; or (ii) increasing the first dose to a second dose and administering the second dose of the compound of formula (I), or a pharmaceutically acceptable salt thereof, to the subject for a second period of time, wherein the second dose is about 40 mg to about 60 mg per day; and increasing the second dose to a third dose and administering the third dose of the compound of formula (I), or a pharmaceutically acceptable salt thereof, to the subject for a third period of time, wherein the third dose is about 80 mg to about 100 mg per day.

6. The method of claim 5, wherein (ii) further comprises increasing the third dose to a fourth dose and administering the fourth dose of the compound of formula (I), or a pharmaceutically acceptable salt thereof, to the subject for a fourth period of time, wherein the fourth dose is about 120 mg per day; or wherein in (ii) the third dose is about 80 mg per day.

7. The method of claim 1, wherein the the compound of formula (I), or a pharmaceutically acceptable salt thereof, is administered at a first dose of about 20 mg per day, and wherein step (b) comprises increasing the first dose to a second dose of about 40 mg per day and administering the second dose of the compound of formula (I), or a pharmaceutically acceptable salt thereof, to the subject for a second period of time.

8. The method of claim 7, wherein the compound of formula (I), or a pharmaceutically acceptable salt thereof, is administered at a second dose of about 40 mg per day, and wherein step (b) further comprises:

increasing the second dose to a third dose of about 60 mg per day and administering the third dose of the compound for formula (I), or a pharmaceutically acceptable salt thereof, to the subject for a third period of time.

9. The method of claim 1, wherein the pharmaceutically acceptable salt of the compound of formula (I) is a hydrochloride salt of formula (II):

(II)

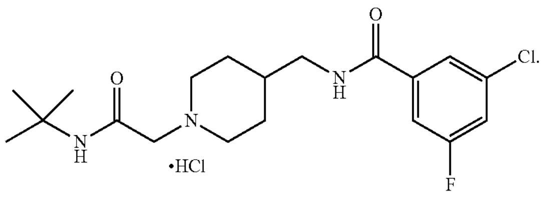

10. The method of claim 1, wherein the compound of formula (I), or a pharmaceutically acceptable salt thereof, is in a modified release dosage formulation comprising at least one modified release polymer.

11. The method of claim 10, wherein about 80% of the compound of formula (I), or a pharmaceutically acceptable salt thereof, is released within 7 hours upon administration to the subject.

12. The method of claim 10, wherein the modified release polymer is hydroxypropyl methylcellulose, ethylcellulose, or a polyacrylate polymer.

13. The method of claim 12, wherein the modified release polymer is hydroxypropyl methylcellulose.

14. The method of claim 1, wherein the method results in an EEG sigma frequency band reduction during NREM sleep in the subject.

15. The method of claim 14, wherein a ratio of the EEG sigma frequency band reduction to an EEG sigma frequency band baseline during NREM sleep in the subject ranges from about 0.4 to about 0.7.

16. The method of claim 1, wherein the first period of time is 3 days to 9 days.

17. The method of claim 16, wherein the first period of time is 7 days.

18. The method of claim 1, wherein the second period of time is 3 days to 9 days.

19. The method of claim 18, wherein the second period of time is 7 days.

20. The method of claim 1, wherein administering the titrated dose of the compound of formula (I), or a pharmaceutically acceptable salt thereof, comprises:

(a) administering to the subject a first dose of the compound of formula (I), or a pharmaceutically acceptable salt thereof, of about 20 mg to about 40 mg per day for a first period of time;

(b) administering to the subject a second dose of the compound of formula (I), or a pharmaceutically acceptable salt thereof, of about 40 mg to about 80 mg per day for a second period of time; and (c) administering to the subject a third dose of the compound of formula (I), or a pharmaceutically acceptable salt thereof, of about 60 mg to about 120 mg for a third period of time.

21. The method of claim 20, wherein the first dose is about 20 mg per day or 40 mg per day.

22. The method of claim 21, wherein the first dose is about 20 mg per day.

23. The method of claim 20, wherein the second dose is about 40 mg per day, about 60 mg per day or about 80 mg per day.

24. The method of claim 23, wherein the second dose is about 40 mg per day.

25. The method of claim 20, wherein the third dose is about 60 mg per day, about 80 mg per day, about 100 mg per day or about 120 mg per day.

26. The method of claim 25, wherein the third dose is about 60 mg per day.

27. The method of claim 20, wherein the third period of time is 3 days to 9 days.

28. The method of claim 27, wherein the third period of time is 7 days.

29. The method of claim 8, wherein step (b) further comprises increasing the third dose to a fourth dose of about 80 mg per day and administering the fourth dose of the compound of formula (I), or a pharmaceutically acceptable salt thereof, to the subject for a fourth period of time.

30. The method of claim 29, wherein step (b) further comprises increasing the fourth dose to a fifth dose of about 100 mg per day and administering the fifth dose of the compound of formula (I), or a pharmaceutically acceptable salt thereof, to the subject for a fifth period of time, wherein the maximum titrated dose of the compound of formula (I), or a pharmaceutically acceptable salt thereof, is about 120 mg per day.

* * * * *